(12) United States Patent
Ren et al.

(10) Patent No.: US 10,098,889 B2
(45) Date of Patent: Oct. 16, 2018

(54) COMPLEXES AND SALTS OF DIHYDROPYRIMIDINE DERIVATIVES AND THEIR APPLICATION IN PHARMACEUTICALS

(71) Applicant: SUNSHINE LAKE PHARMA CO., LTD., Dongguan, Guangdong (CN)

(72) Inventors: Qingyun Ren, Dongguan (CN); Liang Chen, Dongguan (CN); Xinchang Liu, Dongguan (CN); Jinsheng Liang, Dongguan (CN); Chenliang Wu, Dongguan (CN); Zhifu Zou, Dongguan (CN); Guanghua Yan, Dongguan (CN); Desheng Huangfu, Dongguan (CN); Siegfried Goldmann, Dongguan (CN); Yingjun Zhang, Dongguan (CN)

(73) Assignee: SUNSHINE LAKE PHARMA CO., LTD., Dongguan, Guangdong (CN)

( * ) Notice: Subject to any disclaimer, the term of this patent is extended or adjusted under 35 U.S.C. 154(b) by 0 days.

(21) Appl. No.: 15/539,147

(22) PCT Filed: Feb. 1, 2016

(86) PCT No.: PCT/CN2016/073105
§ 371 (c)(1),
(2) Date: Jun. 23, 2017

(87) PCT Pub. No.: WO2016/124126
PCT Pub. Date: Aug. 11, 2016

(65) Prior Publication Data
US 2018/0263991 A1    Sep. 20, 2018

(30) Foreign Application Priority Data
Feb. 7, 2015   (CN) .......................... 2015 1 0068258

(51) Int. Cl.
*C07D 417/14*    (2006.01)
*A61K 31/5377*    (2006.01)
*A61P 35/00*    (2006.01)
*A61P 31/20*    (2006.01)
*A61P 1/16*    (2006.01)

(52) U.S. Cl.
CPC ............ *A61K 31/5377* (2013.01); *A61P 1/16* (2018.01); *A61P 31/20* (2018.01); *A61P 35/00* (2018.01); *C07D 417/14* (2013.01)

(58) Field of Classification Search
CPC .......................... C07D 417/14; A61K 31/5377
USPC ........................................ 544/122; 514/235.8
See application file for complete search history.

(56) References Cited

U.S. PATENT DOCUMENTS

| 5,250,531 | A  | 10/1993 | Cooper |
| 6,057,332 | A  | 5/2000 | Michne et al. |
| 6,218,538 | B1 | 4/2001 | Downs et al. |
| 6,436,943 | B1 | 8/2002 | Stoltefuss et al. |
| 6,503,913 | B1 | 1/2003 | Goldmann et al. |
| 6,696,451 | B1 | 2/2004 | Stoltefuss et al. |
| 7,074,784 | B2 | 7/2006 | Goldmann |
| 7,157,461 | B2 | 1/2007 | Murugesan et al. |
| 8,106,196 | B2 | 1/2012 | Li et al. |
| 8,168,642 | B2 | 5/2012 | Li et al. |
| 8,329,902 | B2 | 12/2012 | Li et al. |
| RE44,987  | E  | 7/2014 | Goldmann et al. |
| 8,802,669 | B2 | 8/2014 | Li et al. |
| 9,233,933 | B2 | 1/2016 | Vandyck et al. |
| 9,233,978 | B2 | 1/2016 | Guo et al. |
| 9,266,904 | B2 | 2/2016 | Guo et al. |
| 2013/0267517 | A1 | 10/2013 | Guo et al. |
| 2015/0031687 | A1 | 1/2015 | Guo et al. |
| 2015/0152096 | A1 | 6/2015 | Zhang et al. |
| 2015/0218182 | A1 | 8/2015 | Zlotnick et al. |
| 2015/0292045 | A1 | 10/2015 | Levrero et al. |

FOREIGN PATENT DOCUMENTS

| CN | 101744823 B | 6/2010 |
| CN | 103664897 A | 3/2014 |
| CN | 103664899 A | 3/2014 |
| CN | 103664925 A | 3/2014 |
| CN | 104650069 A2 | 5/2015 |
| CN | 104650070 A | 5/2015 |
| EP | 0202654 A2 | 11/1986 |
| WO | WO2000058302 A1 | 10/2000 |
| WO | WO2001068639 A1 | 9/2001 |
| WO | WO2001068641 A1 | 9/2001 |
| WO | WO2001068642 A1 | 9/2001 |
| WO | WO2001068647 A1 | 9/2001 |
| WO | WO2008154818 A1 | 12/2008 |
| WO | WO2008154819 A1 | 12/2008 |
| WO | WO2008154820 A1 | 12/2008 |
| WO | WO2010069147 A1 | 6/2010 |
| WO | WO 2014/037480 * | 3/2014 |
| WO | WO 2014153459 A2 | 9/2014 |
| WO | WO2015074546 A1 | 5/2015 |
| WO | WO2015180631 A1 | 12/2015 |
| WO | WO2016012470 A1 | 1/2016 |
| WO | WO2016202721 A1 | 12/2016 |

OTHER PUBLICATIONS

Liu, Rong, ed., "Water-Insoluble Drug Formulation," CRC Press, 2008, Chapter 15, pp. 417-435.*

(Continued)

*Primary Examiner* — Deepak R Rao
(74) *Attorney, Agent, or Firm* — Kam Wah Law

(57) ABSTRACT

This invention relates to L-tartaric acid complexes, acid addition salts, base addition salts of the compound named (S)-4-(((R)-6-(2-chloro-4-fluorophenyl)-5-(methoxycarbonyl)-2-(thiazol-2-yl)-3,6-dihydropyrimidin-4-yl)methyl)morpholine-3-carboxylic acid or tautomer thereof and pharmaceutical compositions thereof, and further relates to use of the compounds or the pharmaceutical compositions in the manufacture of a medicament, especially for use in preventing, managing, treating or lessening a HBV infection. The complex, acid addition salt or base addition salt of the present invention is crystalline form, substantially crystalline form, polymorphism, amorphism, hydrate or solvate.

23 Claims, 30 Drawing Sheets

(56) References Cited

OTHER PUBLICATIONS

Bastin et al., "Salt Selection and Optimisation Procedures for Pharmaceutical New Chemical Entities," Organic Process Research and Development, 2000, vol. 4, pp. 427-435.*
Morris et al., "An Integrated Approach to the Selection of Optimal Salt form for a New Drug Candidate," International Journal of Pharmaceuticals, 105 (1994), pp. 209-217.*
Adeyeye, Moji, ed., "Preformulation in Solid Dosage Form Development," Informa Healthcare, 2008, Chaper 2,3, pp. 63-80.*
Gould, International Journal of Therapeutics 33, 201 (1986).*
Serajuddin, "Salt Formation to Improve Drug Solvability," Advanced Drug Delivery Reviews, vol. 59, 2007, pp. 603-615.*
Swarbrick et al., eds., Encylopedia of Pharmaceutical Technology 13 (Marcel Decker, NY 1996), pp. 453-499.*
Douglas, Jr., Introduction to Viral Diseases, Cecil Textbook of Medicine, 20th Edition, vol. 2, pp. 1739-1747, 1996.*
Bosseray et al., PubMed Abstract (Pathol Biol (Paris) 50(8):483-92), 2002.*
Goff, PubMed Abstract (J Gene Med. 3(6):517-28), 2001.*
Razonable et al., PubMed Abstract (Herpes 10(3):60-5), 2003.*
ISR, dated May 6, 2016.
Written Opinion, dated May 6, 2016.

* cited by examiner

COMPLEXES AND SALTS OF DIHYDROPYRIMIDINE DERIVATIVES AND THEIR APPLICATION IN PHARMACEUTICALS

CROSS-REFERENCE TO RELATED APPLICATIONS

This is a U.S. national stage application of the International Patent Application No. PCT/CN2016/073105, filed Feb. 1, 2016, which claims priorities to Chinese Patent Application No. 201510068258.X, filed Feb. 7, 2015, both of which are incorporated herein by reference in their entirety.

FIELD

The present invention belongs to the field of medicine. This invention relates to L-tartaric acid complexes, acid addition salts, base addition salts of the compound named (S)-4-(((R)-6-(2-chloro-4-fluorophenyl)-5-(methoxycarbonyl)-2-(thiazol-2-yl)-3,6-dihydropyrimidin-4-yl)methyl) morpholine-3-carboxylic acid (I) or tautomer (Ia) thereof and pharmaceutical compositions thereof, and further relates to use of the salts or the pharmaceutical compositions in the manufacture of a medicament, especially for use in preventing, managing, treating or lessening an HBV infection. The complexes, acid addition salts or base addition salts of the present invention are crystal form, substantially crystalline, polymorphism, amorphism, hydrate or solvate.

BACKGROUND

Hepatitis B virus belongs to the family of hepadnaviridae. It can cause acutely and/or persistently and progressively chronic diseases. Many other clinical manifestations in the pathological morphology can be also caused by HBV—in particular chronic hepatitis, cirrhosis and hepatocellular carcinoma. Additionally, coinfection with hepatitis D virus may have adverse effects on the progress of the disease.

The conventional medicaments approved to be used for treating chronic hepatitis are interferon and lamivudine. However, the interferon has a moderate activity and a great adverse side reaction. Although lamivudine has good activity, its resistance develops rapidly during the treatment and relapse effects often appear after the treatment has stopped. The $IC_{50}$ value of lamivudine (3-TC) is 300 nM (Science, 2003, 299, 893-896).

Deres, et al., have reported heteroaryl-substituted dihydropyrimidine (HAP) compounds including Bay41-4109 and Bay39-5493, and these compounds play a role in blocking HBV replication by preventing the proper formation of viral core particles (nucleocapsids). It has been demonstrated that Bay41-4109 has a better drug metabolic properties in clinical study (Science, 2003, 299, 893-896). The study of these compounds' mechanism indicated that through reacting with 113-143 amino acid residues of a core protein, heteroaryl-substituted dihydropyrimidine compounds have changed the angle between dimers which can form nucleocapsids, and thus led to forming unstably expanded nucleocapsids, which accelerate the degradation of the core protein (Biochem. Pharmacol, 2003, 66, 2273-2279).

Patent application WO2014029193 and CN201310373003.5 have disclosed a number of dihydropyrimidine (HAP) compounds having the effect of blocking replication of HBV virus, wherein the compounds of formula (IIa) and (IIb) have better activity:

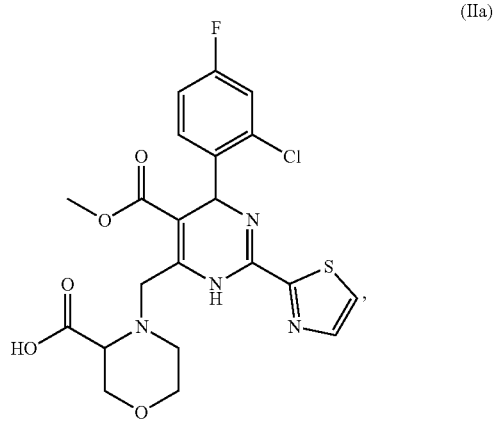

(IIa)

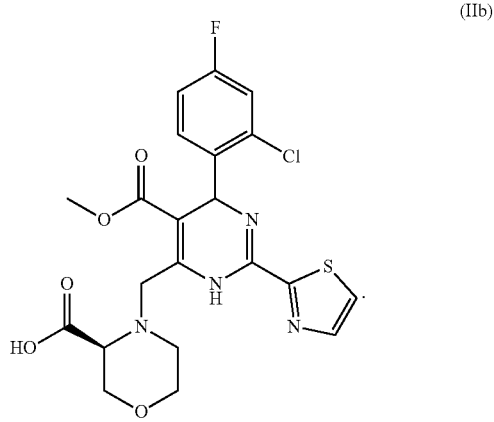

(IIb)

In the present invention, the compound of formula (I) named (S)-4-(((R)-6-(2-chloro-4-fluorophenyl)-5-(methoxycarbonyl)-2-(thiazol-2-yl)-3,6-dihydropyrimidin-4-yl)methyl)morpholine-3-carboxylic acid was isolated from the compound of formula (IIb).

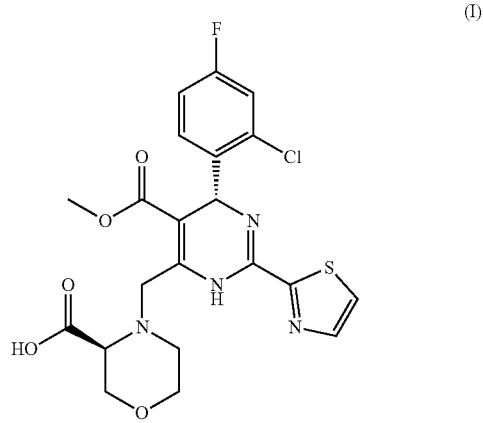 [SMILES: COC(=O)C1=C(CN2CCOC[C@H]2C(=O)O)NC(c2nccs2)=N[C@H]1c1ccc(F)cc1Cl]

(I)

During the preparation process of the compound named (S)-4-(((R)-6-(2-chloro-4-fluorophenyl)-5-(methoxycarbonyl)-2-(thiazol-2-yl)-3,6-dihydropyrimidin-4-yl)methyl) morpholine-3-carboxylic acid, it is found that the compound, as a foamy solid, has poor flowability and certain hygroscopicity so that it is disadvantageous for keeping and weighing, which involves a number of inconveniences.

Therefore, in order to find a solid form with better drugability, the applicant developed compound (I) into various acid addition salts and base addition salts through a number of experimental study and found that salified compound has significantly improved purity, physical behavior facilitating formulation, small hygroscopicity facilitating keeping and weighing, and improved solubility. Surprisingly, the applicant also obtained a complex formed from compound (I) and L-tartaric acid during the experiments. The complex has not only a simple preparation process facilitating scale-up processes but also physical behaviors facilitating formulation, high purity and good solubility. Furthermore, the complex has superior stability to keep the purity unchanged substantially under high temperature, high humidity and illumination conditions, which lead to superior drugability.

SUMMARY OF THE INVENTION

This invention relates to complexes, acid addition salts, base addition salts of the compound named (S)-4-(((R)-6-(2-chloro-4-fluorophenyl)-5-(methoxycarbonyl)-2-(thiazol-2-yl)-3,6-dihydropyrimidin-4-yl)methyl)morpholine-3-carboxylic acid (I) or tautomer (Ia) thereof and pharmaceutical compositions thereof, and further relates to use of the salts or the pharmaceutical compositions in the manufacture of a medicament, especially for use in preventing, managing, treating or lessening an HBV infection. The complexes, acid addition salts or base addition salts of the present invention are crystalline form, substantially crystalline form, polymorphism, amorphism, hydrate or solvate.

In one aspect, the present invention relates to a complex formed from L-tartaric acid and a compound of formula (I) or (Ia):

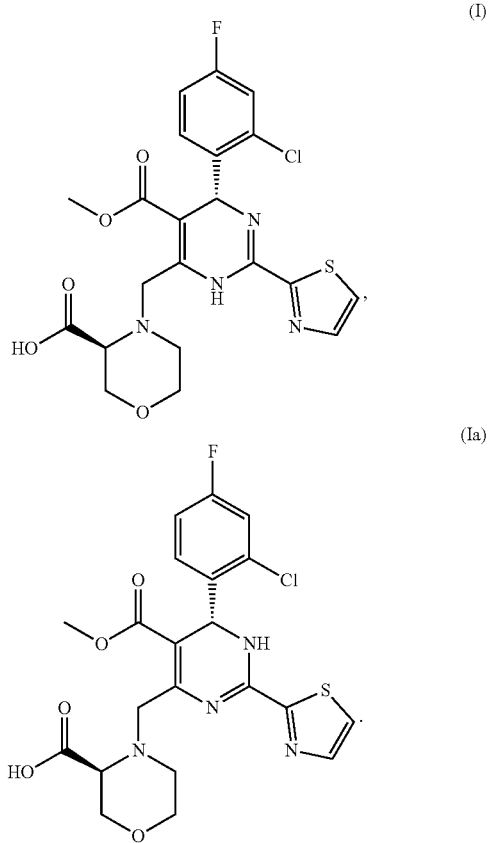

In some embodiments, the complex disclosed herein is L-tartaric acid complex having crystalline form I(A), a mole ratio of the compound of formula (I) or (Ia) to L-tartarate is 1:1 in the L-tartaric acid complex having crystalline form I(A), and wherein the crystalline form I(A) of L-tartaric acid complex has the following characteristics:

(1) The crystalline form I(A) of L-tartaric acid complex exhibits the following characteristic X-ray powder diffraction peaks expressed in degrees $2\theta$ at $17.82\pm0.2°$, $19.51\pm0.2°$, $21.61\pm0.2°$, $22.56\pm0.2°$, $23.36\pm0.2°$, $23.54\pm0.2°$, $23.79\pm0.2°$ and $31.07\pm0.2°$; or (2) The crystalline form I(A) of L-tartaric acid complex has the following unit cell parameters:

Unit cell specification: a=11.7649(3) Å, b=9.75352(19) Å, c=12.3294(2) Å, α=90°, β=102.581(2)°, γ=90°;

Space group: monoclinic, $P2_1$;

Unit cell volume: 1380.83(5) $Å^3$;

Asymmetric unit number Z in the unit cell: 2; and

Density: 1.551 $g/cm^3$.

In some embodiments, the complex disclosed herein is L-tartaric acid complex having crystalline form I(A), and wherein the crystalline form I(A) exhibits the following characteristic X-ray powder diffraction peaks expressed in degrees $2\theta$ at $9.29\pm0.2°$, $17.82\pm0.2°$, $19.51\pm0.2°$, $20.80\pm0.2°$, $21.61\pm0.2°$, $22.56\pm0.2°$, $23.36\pm0.2°$, $23.54\pm0.2°$, $23.79\pm0.2°$ and $31.07\pm0.2°$.

In some embodiments, the complex disclosed herein is L-tartaric acid complex having crystalline form I(A), and wherein the crystalline form I(A) exhibits the following characteristic X-ray powder diffraction peaks expressed in degrees $2\theta$ at $7.30°\pm0.2°$, $7.31°\pm0.2°$, $7.61°\pm0.2°$, $9.29°\pm0.2°$, $11.60°\pm0.2°$, $14.69°\pm0.2°$, $15.33°\pm0.2°$, $17.22°\pm0.2°$, $17.82°\pm0.2°$, $18.08°\pm0.2°$, $18.42°\pm0.2°$, $19.51°\pm0.2°$, $20.51°\pm0.2°$, $20.80°\pm0.2°$, $21.61°\pm0.2°$, $22.56°\pm0.2°$, $23.05°\pm0.2°$, $23.36°\pm0.2°$, $23.54°\pm0.2°$, $23.79°\pm0.2°$, $24.39°\pm0.2°$, $24.81°\pm0.2°$, $25.78°\pm0.2°$, $26.07°\pm0.2°$, $27.34°\pm0.2°$, $28.25°\pm0.2°$, $28.87°\pm0.2°$, $29.72°\pm0.2°$, $30.22°\pm0.2°$, $31.07°\pm0.2°$, $31.55°\pm0.2°$, $32.25°\pm0.2°$, $32.85°\pm0.2°$, $33.24°\pm0.2°$, $34.24°\pm0.2°$, $35.03°\pm0.2°$, $35.22°\pm0.2°$, $36.03°\pm0.2°$, $36.88°\pm0.2°$, $37.33°\pm0.2°$, $37.86°\pm0.2°$ and $38.36°\pm0.2°$.

In some embodiments, the complex disclosed herein is L-tartaric acid complex having crystalline form I(A), and wherein the crystalline form I(A) has a differential scanning calorimetry thermogram comprising an endothermic peak at 186.94° C.±3° C.; and/or a Raman spectrogram comprising the following absorption peaks at 51, 71, 115, 144, 158, 180, 196, 234, 303, 427, 688, 746, 767, 818, 837, 905, 1001, 1062, 1075, 1128, 1137, 1165, 1179, 1193, 1230, 1269, 1289, 1324, 1337, 1346, 1357, 1401, 1438, 1453, 1477, 1517, 1541, 1607 and 1679 $cm^{-1}$, and the error margin of the absorption peaks is ±2 $cm^{-1}$.

In some embodiments, the complex disclosed herein is L-tartaric acid complex having crystalline form I(A), and wherein the crystalline form I(A) has a differential scanning calorimetry thermogram comprising an endothermic peak at 193.78° C.±3° C.; and/or a Raman spectrogram comprising the following absorption peaks at 51, 71, 115, 144, 158, 180, 196, 234, 303, 427, 688, 746, 767, 818, 837, 905, 1001, 1062, 1075, 1128, 1137, 1165, 1179, 1193, 1230, 1269, 1289, 1324, 1337, 1346, 1357, 1401, 1438, 1453, 1477, 1517, 1541, 1607 and 1679 $cm^{-1}$, and the error margin of the absorption peaks is ±2 $cm^{-1}$.

In some embodiments, the complex disclosed herein is L-tartaric acid complex having crystalline form I(A), and wherein the crystalline form I(A) has at least one of following features:

(1) an X-ray powder diffraction (XRPD) pattern substantially the same as shown in FIG. 1; or (2) a differential scanning calorimetry thermogram substantially the same as shown in FIG. 2 or FIG. 3; or (3) a Raman spectrogram substantially the same as shown in FIG. 4.

In one aspect, the present invention relates to a salt of the compound of formula (I) or (Ia):

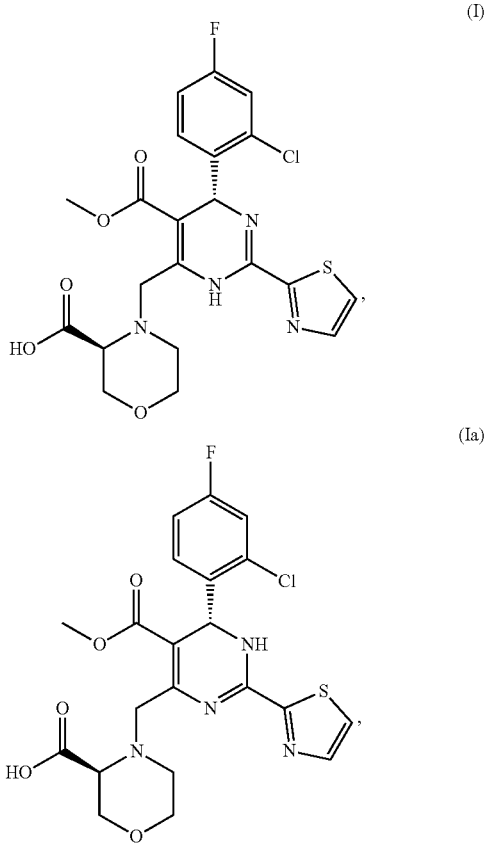

wherein the salt is a pharmaceutically acceptable acid addition salt.

In some embodiments, the salt disclosed herein is an inorganic acid salt or organic acid salt, wherein the inorganic acid salt is hydrochloride, sulfate, hydrosulfate, nitrate, hydrobromide, hydriodate, carbonate, hydrocarbonate, sulphite, hydrosulphite, pyrosulfate, monohydric phosphate, dihydric phosphate, perchlorate, persulfate, hemisulphate, bisulphate, thiocyanate, phosphate, pyrophosphate, metaphosphate, or a combination thereof; and wherein the organic acid salt is formate, acetate, propionate, butyrate, benzoate, malonate, succinate, pyruvate, mesylate, esilate, propanesulfonate, citrate, 4-nitrobenzoate, benzene sulfonate, tosilate, malate, propiolate, 2-tetrolate, 2-hydroxy-ethanesulfonate, vinyl acetate, tartrate, L-tartrate, fumarate, isethionate, maleate, lactate, lactobionate, pamoate, salicylate, mutate, gluceptate, mandelate, 1,2-ethanedisulfonate, 2-naphthalene sulfonate, oxalate, trifluoroacetate, metal triflate, adipate, suberate, sebacate, butyne-1,4-dicarboxylate, hexyne-1,6-dicarboxylate, glycollate, alginate, ascorbate, erythorbate, aspartate, L-aspartate, glutamate, L-glutamate, 2-phenoxybenzoate, 4'-hydroxybenzophenone-2-carboxylate, acetoacetate, 2-hydroxy-ethanesulfonate, benzene sulfonate, borate, chlorobenzoate, camphorate, itaconate, camphorsulfonate, (−)-camphorsulfonate, toluate, dinitrobenzoate, sulfamate, lactobionate, galacturonate, cyclopentylpropionate, dodecylsulfate, acrylate, cypionate, glycerophosphate, methoxybenzoate, digluconate, gluconate, enantate, caproate, 2-hydroxy-ethanesulfonate, pivalate, glucuronate, laurate, phthalate, phenylacetate, lauryl sulfate, 2-acetoxybenzoate, nicotinate, cinnamate, oleate, palmitate, pamoate, pectate, phthalate, glutarate, hydroxymaleate, hydroxybenzoate, phenylacetate, 3-hydroxy-2-naphthoate, 3-phenylproponate, isobutyrate, pivalate, picrate, stearate, 2,2-dichloroacetate, acylation amino acid salt, alginate, 4-acetamidobenzenesulfonate, decanoate, cholate, caprylate, pelargonate, cyclamate, phthalate, cysteine hydrochloride, sorbate, pamoate, galactarate, glycine hydrochloride, naphthalenedisulfonate, xylene sulfonate, cystamine dihydrochloride, undecanoate, polyvinyl sulfonate, sulfosalicylate, phenylbutyrate, 4-hydroxybutyrate, polyvinylsulfate, 1-naphthalenesulfonate, 2-naphthalenesulfonate, valerate, or a combination thereof.

In some embodiments, the salt disclosed herein is hydrochloride having crystalline form I(B), and wherein the crystalline form I(B) exhibits the following characteristic X-ray powder diffraction peaks expressed in degrees 2θ at 15.73±0.2°, 17.21±0.2°, 20.44±0.2°, 22.04±0.2°, 23.44±0.2°, 28.39±0.2°, 30.86±0.2° and 33.61±0.2°.

In some embodiments, the salt disclosed herein is hydrochloride having crystalline form II, and wherein the crystalline form II exhibits the following characteristic X-ray powder diffraction peaks expressed in degrees 2θ at 11.90±0.2°, 21.04±0.2°, 21.96±0.2°, 23.30±0.2°, 24.60±0.2°, 27.20±0.2°, 28.75±0.2° and 39.21±0.2°.

In some embodiments, the salt disclosed herein is hydrochloride having crystalline form I(B), and wherein the crystalline form I(B) exhibits the following characteristic X-ray powder diffraction peaks expressed in degrees 2θ at 15.73°±0.2°, 17.21°±0.2°, 20.44°±0.2°, 22.04°±0.2°, 23.44°±0.2°, 24.73°±0.2°, 28.39°±0.2°, 30.86°±0.2°, 31.73°±0.2°, 32.78°±0.2°, 33.61°±0.2°, 35.63°±0.2°, 37.16°±0.2° and 38.13°±0.2°.

In some embodiments, the salt disclosed herein is hydrochloride having crystalline form II, and wherein the crystalline form II exhibits the following characteristic X-ray powder diffraction peaks expressed in degrees 2θ at 11.90±0.2°, 18.53±0.2°, 21.04±0.2°, 21.96±0.2°, 23.30±0.2°, 24.60±0.2°, 27.20±0.2°, 28.75±0.2°, 33.62±0.2° and 39.21±0.2°.

In some embodiments, the salt disclosed herein is hydrochloride having crystalline form II, and wherein the crystalline form II exhibits the following characteristic X-ray powder diffraction peaks expressed in degrees 2θ at 6.39±0.2°, 11.20±0.2°, 11.90±0.2°, 12.68±0.2°, 13.68±0.2°, 15.06±0.2°, 15.65±0.2°, 16.27±0.2°, 18.53±0.2°, 19.00±0.2°, 20.21±0.2°, 21.04±0.2°, 21.61±0.2°, 21.96±0.2°, 22.24±0.2°, 23.30±0.2°, 24.00±0.2°, 24.60±0.2°, 25.50±0.2°, 26.48±0.2°, 27.20±0.2°, 28.32±0.2°, 28.75±0.2°, 29.51±0.2°, 30.31±0.2°, 31.39±0.2°, 31.87±0.2°, 32.40±0.2°, 33.62±0.2°, 34.53±0.2°, 35.12±0.2°, 35.80±0.2°, 36.28±0.2°, 36.76±0.2°, 37.48±0.2°, 37.74±0.2°, 38.44±0.2° and 39.21±0.2°; and/or has a differential scanning calorimetry thermogram thereof comprising an endothermic peak at 156.08° C.±3° C.

In some embodiments, the salt disclosed herein is hydrochloride having crystalline form I(B) having an X-ray powder diffraction (XRPD) pattern substantially the same as shown in FIG. 5; or wherein the salt is hydrochloride having crystalline form II having an X-ray powder diffraction (XRPD) pattern substantially the same as shown in FIG. 6, and/or a differential scanning calorimetry thermogram substantially the same as shown in FIG. 7.

In some embodiments, the salt disclosed herein is hydrobromide having crystalline form I(C), and wherein the crystalline form I(C) exhibits the following characteristic X-ray powder diffraction peaks expressed in degrees 2θ at 20.69±0.2°, 21.61±0.2°, 23.18±0.2°, 24.20±0.2°, 27.09±0.2°, 28.05±0.2°, 28.59±0.2° and 33.13±0.2°.

In some embodiments, the salt disclosed herein is hydrobromide having crystalline form I(C), and wherein the crystalline form I(C) exhibits the following characteristic X-ray powder diffraction peaks expressed in degrees 2θ at 14.87±0.2°, 20.69±0.2°, 21.61±0.2°, 23.18±0.2°, 24.20±0.2°, 25.38±0.2°, 27.09±0.2°, 28.05±0.2°, 28.59±0.2° and 33.13±0.2°.

In some embodiments, the salt disclosed herein is hydrobromide having crystalline form I(C), and wherein the crystalline form I(C) exhibits the following characteristic X-ray powder diffraction peaks expressed in degrees 2θ at 6.29±0.2°, 10.04±0.2°, 10.99±0.2°, 11.83±0.2°, 14.87±0.2°, 15.44±0.2°, 16.05±0.2°, 18.41±0.2°, 18.79±0.2°, 19.12±0.2°, 20.06±0.2°, 20.69±0.2°, 21.30±0.2°, 21.61±0.2°, 22.02±0.2°, 22.93±0.2°, 23.18±0.2°, 23.67±0.2°, 24.20±0.2°, 25.38±0.2°, 26.14±0.2°, 26.73±0.2°, 27.09±0.2°, 27.83±0.2°, 28.05±0.2°, 28.59±0.2°, 29.06±0.2°, 29.92±0.2°, 31.05±0.2°, 31.63±0.2°, 32.29±0.2°, 32.76±0.2°, 33.13±0.2°, 33.63±0.2°, 34.10±0.2°, 34.55±0.2°, 35.42±0.2°, 35.99±0.2°, 36.36±0.2°, 37.02±0.2°, 37.93±0.2°, 38.49±0.2°, 38.72±0.2° and 39.10±0.2°; and/or has a differential scanning calorimetry thermogram thereof comprising an endothermic peak at 158.95° C.±3° C.

In some embodiments, the salt disclosed herein is hydrobromide having crystalline form I(C) having an X-ray powder diffraction (XRPD) pattern substantially the same as shown in FIG. 8; and/or a differential scanning calorimetry thermogram substantially the same as shown in FIG. 9.

In some embodiments, the salt disclosed herein is mesylate having crystalline form I(E), and wherein the crystalline form I(E) exhibits the following characteristic X-ray powder diffraction peaks expressed in degrees 2θ at 5.58°±0.2°, 10.730±0.2°, 17.100±0.2°, 17.96°±0.2° and 23.98°±0.2°.

In some embodiments, the salt disclosed herein is mesylate having crystalline form II, a mole ratio of the compound of formula (I) or (Ia) to mesylate is 3:1 in mesylate having crystalline form II, and wherein the crystalline form II exhibits the following characteristic X-ray powder diffraction peaks expressed in degrees 2θ at 8.28°±0.2°, 19.70°±0.2°, 20.00°±0.2°, 24.78°±0.2° and 25.66°±0.2°.

In some embodiments, the salt disclosed herein is mesylate having crystalline form I(E), and wherein the crystalline form I(E) exhibits the following characteristic X-ray powder diffraction peaks expressed in degrees 2θ at 5.58°±0.2°, 10.73°±0.2°, 17.10°±0.2°, 17.96°±0.2°, 19.20°±0.2°, 22.20°±0.2°, 22.50°±0.2°, 23.98°±0.2°, 24.24°±0.2° and 26.87°±0.2°.

In some embodiments, the salt disclosed herein is mesylate having crystalline form II, and wherein the crystalline form II exhibits the following characteristic X-ray powder diffraction peaks expressed in degrees 2θ at 8.28°±0.2°, 9.11°±0.2°, 11.36°±0.2°, 17.07°±0.2°, 17.67°±0.2°, 19.70°±0.2°, 20.00°±0.2°, 24.78°±0.2°, 25.66°±0.2° and 26.10°±0.2°.

In some embodiments, the salt disclosed herein is mesylate having crystalline form I(E), and wherein the crystalline form I(E) exhibits the following characteristic X-ray diffraction peaks expressed in degrees 2θ at 5.58°±0.2°, 9.59°±0.2°, 10.73°±0.2°, 11.13°±0.2°, 14.43°±0.2°, 14.71°±0.2°, 16.62°±0.2°, 17.10°±0.2°, 17.96°±0.2°, 18.59°±0.2°, 19.20°±0.2°, 19.77°±0.2°, 20.12°±0.2°, 20.33±0.2°, 20.95°±0.2, 21.56°±0.2, 22.2°±0.2, 22.5°±0.2, 23.54°±0.2°, 23.98°±0.2°, 24.24°±0.2°, 24.51°±0.2°, 24.83°±0.2°, 25.50°±0.2°, 26.32°±0.2°, 26.87°±0.2°, 27.70°±0.2°, 28.10°±0.2°, 28.36°±0.2°, 28.89°±0.2°, 29.490° 0.2°, 30.02°±0.2°, 30.58°±0.2°, 31.22°±0.2°, 31.65°±0.2°, 32.02°±0.2°, 32.43°±0.2, 32.94°±0.2°, 33.52°±0.2°, 34.50°±0.2°, 34.88°±0.2°, 35.59°±0.2°, 36.00°±0.2°, 36.46°±0.2°, 36.92°±0.2°, 37.71°±0.2° and 38.88°±0.2°, and/or has a differential scanning calorimetry thermogram comprising an endothermic peak at 155.48° C.±3° C.

In some embodiments, the salt disclosed herein is mesylate having crystalline form II, and wherein the crystalline form II exhibits the following characteristic X-ray powder diffraction peaks expressed in degrees 2θ at 7.81°±0.2°, 8.28°±0.2°, 9.11°±0.2°, 9.85°±0.2°, 11.36°±0.2°, 12.56°±0.2°, 14.37°±0.2°, 14.72°±0.2°, 15.33°±0.2°, 16.48°±0.2°, 17.07°±0.2°, 17.67°±0.2°, 18.51°±0.2°, 19.70°±0.2°, 20.00°±0.2°, 20.17°±0.2°, 21.17°±0.2°, 21.60°±0.2°, 21.97°±0.2°, 22.47°±0.2°, 22.80°±0.2°, 23.22°±0.2°, 24.10°±0.2°, 24.78°±0.2°, 25.66°±0.2°, 26.10°±0.2°, 26.44°±0.2°, 27.05°±0.2°, 27.48°±0.2°, 28.21°±0.2°, 28.79°±0.2°, 29.60°±0.2°, 30.46°±0.2°, 31.22°±0.2°, 32.89°±0.2°, 33.37°±0.2°, 33.61°±0.2°, 34.39°±0.2°, 35.09°±0.2°, 36.32°±0.2°, 36.94°±0.2°, 37.59°±0.2° and 38.41°±0.2°, and/or has a differential scanning calorimetry thermogram comprising an endothermic peak at 128.26° C.±3° C.

In some embodiments, the salt disclosed herein is mesylate having crystalline form I(E) having an X-ray powder diffraction (XRPD) pattern substantially the same as shown in FIG. 26; and/or a differential scanning calorimetry thermogram substantially the same as shown in FIG. 27.

In some embodiments, the salt disclosed herein is mesylate having crystalline form II having an X-ray powder diffraction (XRPD) pattern substantially the same as shown in FIG. 28; and/or a differential scanning calorimetry thermogram substantially the same as shown in FIG. 29.

In some embodiments, the salt disclosed herein is amorphous hydrochloride having an X-ray powder diffraction (XRPD) pattern substantially the same as shown in FIG. 10; or the salt disclosed herein is amorphous benzene sulfonate having an X-ray powder diffraction (XRPD) pattern substantially the same as shown in FIG. 11; or the salt disclosed herein is amorphous benzene tosilate having an X-ray powder diffraction (XRPD) pattern substantially the same as shown in FIG. 12; or the salt disclosed herein is amorphous oxalate having an X-ray powder diffraction (XRPD) pattern substantially the same as shown in FIG. 13; or the salt disclosed herein is amorphous benzene citrate having an X-ray powder diffraction (XRPD) pattern substantially the same as shown in FIG. 14; or the salt disclosed herein is amorphous maleate having an X-ray powder diffraction (XRPD) pattern substantially the same as shown in FIG. 15; or the salt disclosed herein is amorphous hydrobromide having an X-ray powder diffraction (XRPD) pattern substantially the same as shown in FIG. 16; or the salt disclosed herein is amorphous sulfate having an X-ray powder diffraction (XRPD) pattern substantially the same as shown in FIG. 17; or the salt disclosed herein is amorphous nitrate having an X-ray powder diffraction (XRPD) pattern substantially the same as shown in FIG. 18; or the salt disclosed herein is amorphous L-tartarate having an X-ray powder diffraction (XRPD) pattern substantially the same as shown in FIG. 19; or the salt disclosed herein is amorphous salicylate having an X-ray powder diffraction (XRPD) pattern substantially the same as shown in FIG. 20.

In another aspect, the present invention relates to a salt of the compound of formula (I) or (Ia):

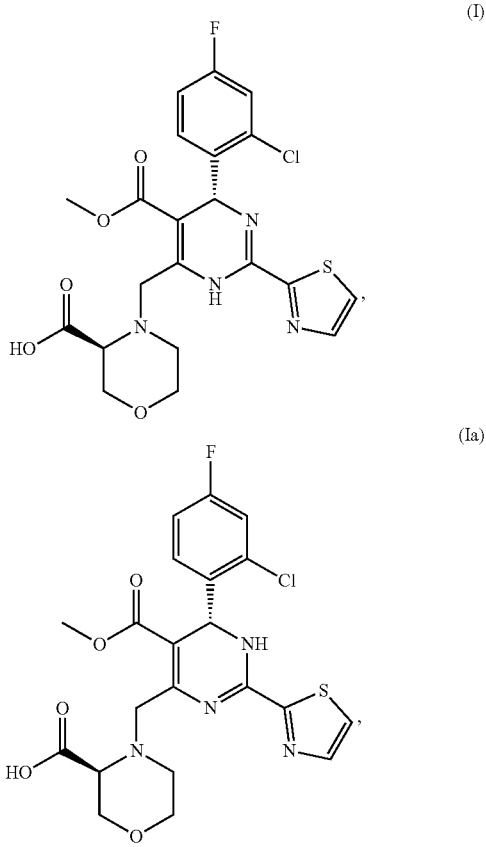

Wherein the salt is a pharmaceutically acceptable base addition salt.

In some embodiments, the salt disclosed herein is a lithium salt, sodium salt, potassium salt, calcium salt, magnesium salt, aluminium salt, iron salt, zinc salt, ammonium salt, or a combination thereof; or the salt disclosed herein is formed by the compound of formula (I) or formula (Ia) with methylamine, dimethylamine, trimethylamine, ethylamine, diethylamine, triethylamine, isopropylamine, 2-ethylaminoethanol, pyridine, methylpyridine, ethanolamine, diethanolamine, ammonium, tetramethyl ammonium, tetraethylammonium, triethanolamine, piperidine, piperazine, morpholine, lysine, arginine, L-arginine, histidine, L-histidine, N-methylglucamine, dimethylglucamine, ethylglucamine, dicyclohexylamine, 1,6-hexamethylenediamine, glucamine, sarcosine, serinol, tris(hydroxymethyl)aminomethane, aminopropanediol, 1-amino-2,3,4-butanetriol, L-lysine, ornithine, or a combination thereof.

In some embodiments, the salt disclosed herein is a calcium salt having crystalline form I(D), and wherein the crystalline form I(D) exhibits the following characteristic X-ray powder diffraction peaks expressed in degrees 2θ at 9.14±0.2°, 13.13±0.2°, 17.31±0.2°, 18.33±0.2°, 19.07±0.2°, 23.02±0.2°, 23.88±0.2° and 27.71±0.2°.

In some embodiments, the salt disclosed herein is a calcium salt having crystalline form I(D), and wherein the crystalline form I(D) exhibits the following characteristic X-ray powder diffraction peaks expressed in degrees 2θ at 4.54±0.2°, 9.14±0.2°, 13.13±0.2°, 17.31±0.2°, 18.33±0.2°, 19.07±0.2°, 23.02±0.2°, 23.88±0.2°, 27.71±0.2° and 31.75±0.2°.

In some embodiments, the salt disclosed herein is a calcium salt having crystalline form I(D), and wherein the crystalline form I(D) exhibits the following characteristic X-ray powder diffraction peaks expressed in degrees 2θ at 4.540° 0.2°, 9.14°±0.2°, 11.09°±0.2°, 11.79°±0.2°, 13.13°±0.2°, 13.75°±0.2°, 14.29°±0.2°, 16.43°±0.2°, 16.78°±0.2°, 17.31°±0.2°, 18.33°±0.2°, 19.07°±0.2°, 20.45°±0.2°, 20.81°±0.2°, 22.01°±0.2°, 23.02°±0.2°, 23.88°±0.2°, 24.87°±0.2°, 25.48°±0.2°, 26.43°±0.2°, 27.71°±0.2°, 28.80°±0.2°, 30.87°±0.2°, 31.75°±0.2°, 32.48°±0.2°, 33.55°±0.2°, 35.04°±0.2°, 36.18°±0.2°, 36.76°±0.2°, 38.73°±0.2° and 39.16°±0.2°, and/or has a Raman spectrogram thereof comprising the following absorption peaks at 52, 82, 107, 139, 194, 235, 254, 301, 355, 390, 425, 440, 497, 551, 600, 622, 656, 690, 720, 749, 773, 802, 824, 852, 900, 953, 1009, 1069, 1093, 1113, 1167, 1211, 1242, 1309, 1336, 1369, 1426, 1494 and 1597 cm$^{-1}$, and the error margin of the absorption peaks is ±2 cm$^{-1}$.

In some embodiments, the salt disclosed herein is a calcium salt having crystalline form I(D), and wherein the crystalline form I(D) has an X-ray powder diffraction (XRPD) pattern substantially the same as shown in FIG. 21; or/and a Raman spectrogram substantially the same as shown in FIG. 22.

In some embodiments, the salt disclosed herein is an amorphous sodium salt having an X-ray powder diffraction (XRPD) pattern substantially the same as shown in FIG. 23; or the salt is an amorphous calcium salt having an X-ray powder diffraction (XRPD) pattern substantially the same as shown in FIG. 24; or the salt is an amorphous L-lysine salt having an X-ray powder diffraction (XRPD) pattern substantially the same as shown in FIG. 25.

In another aspect, provided herein is a method for preparing complexes of L-tartaric acid and the compound of formula (I) or (Ia), acid addition salts or base addition salts of the compound of formula (I) or (Ia), wherein the method disclosed herein comprises the following steps of: (1) dissolving the compound of formula (I) or (Ia) in an first organic solvent, (2) adding counter-ion solution to the mixture under a controlled temperature to give a precipitate or, (3) adding an second organic solvent to precipitate a solid, (4) collecting the precipitated solid, (5) drying. Furthermore, each of the first organic solvent and the second organic solvent is independently water, methanol, ethanol, n-propanol, isopropanol, n-butanol, tert-butanol, ether, isopropyl ether, petroleum ether, isopropyl acetate, n-propyl acetate, methyl tertiary butyl ether (MTBE), n-heptane, an ethanol-water mixture at a volume ratio from 10:90 to 90:10, acetone, tetrahydrofuran, acetonitrile, methyl ethyl ketone, dichloromethane, ethyl acetate, ethylene glycol, N,N-dimethylformamide or a combination thereof. Further more, the controlled temperature during the reaction is from 20° C. to 80° C.; In some embodiments the controlled temperature during the reaction is from 20° C. to 70° C.; In some other embodiments the controlled temperature during the reaction is −20° C., −15° C., −10° C., 0° C., 10° C., 15° C., 20° C., 25° C., 30° C., 35° C., 40° C., 45° C., 50° C., 55° C., 60° C., 65° C., 70° C., 75° C., 80° C., etc.

In another aspect, provided herein is a pharmaceutical composition comprising a complex, acid addition salt or base addition salt of the compound having formula (I) or (Ia) disclosed herein or a combination thereof, and a pharmaceutically acceptable carrier, excipient, diluent, adjuvant or a combination thereof.

In another aspect, provided herein is use of the complex, acid addition salt or base addition salt of the compound having formula (I) or (Ia) disclosed herein or the pharmaceutical composition in the manufacture of a medicament for preventing, managing, treating or lessening a viral disease or an HBV disease. The use comprises administration of a therapeutically effective dose of the complex, acid addition salt or base addition salt or the composition thereof disclosed herein to a patient.

In some embodiments of the use disclosed herein, wherein the viral disease or the HBV disease is hepatitis B infection or a disease caused by hepatitis B infection. In some other embodiments of the use disclosed herein, wherein the disease caused by hepatitis B infection is cirrhosis or hepatocellular carcinoma.

In another aspect, provided herein is a method for preventing, managing, treating or lessening a viral disease or an HBV disease in a patient. The method comprises administering to the patient with a therapeutically effective amount of the acid addition salt or base addition salt or the composition thereof disclosed herein to a patient.

In some embodiments, the viral disease or HBV disease is hepatitis B infection or a disease caused by hepatitis B infection.

In some embodiments, the disease caused by hepatitis B infection is cirrhosis or hepatocellular carcinoma.

In still another aspect, the acid addition salt or base addition salt of the compound having formula (I) or (Ia) disclosed herein or the pharmaceutical composition is for use in preventing, managing, treating or lessening a viral disease or an HBV disease.

In some embodiments, the viral disease or HBV disease is hepatitis B infection or a disease caused by hepatitis B infection.

In some embodiments, the disease caused by hepatitis B infection is cirrhosis or hepatocellular carcinoma.

Unless defined otherwise, all technical and scientific terms used herein have the same meaning as is commonly understood by one skilled in the art to which this invention belongs. All patents and publications referred to herein are incorporated by reference in their entirety. Although one skilled in the art can use any of the methods and materials similar or identical to those described herein, which could be used in practice or testing of the present invention, but the present invention is described in preferred methods, equipment and materials.

As described herein, "room temperature" refers to a temperature from about 10° C. to about 40° C. In some embodiments, "room temperature" refers to a temperature from about 20° C. to about 30° C.; In some other embodiments, "room temperature" refers to a temperature from about 25° C. to about 30° C.; In yet other embodiments, "room temperature" refers to 10° C., 15° C., 20° C., 25° C., 30° C., 35° C., 40° C., etc.

The term as used herein, "pharmaceutically acceptable" means a substance is acceptable from the standpoint of toxicology for pharmaceutical applications and does not adversely interact with active ingredients.

"Pharmaceutically acceptable salts" refers to within the scope of sound medical judgment, the salt which is suitable for use in contact with humans and lower animals tissue without excessive toxicity, irritation, allergic reactions, etc. and have quite a reasonable benefit/risk ratio. They are well known in the art. For example, Berge et al., describe pharmaceutically acceptable salts in detail in J. Pharmacol Sci, 66 (1997), 1-19, which is incorporated herein by reference.

The term as used herein, "polycrystalline form" or "polymorphism" is defined as the possibility that there are at least two different crystalline arrangements for the same chemical molecule.

The term as used herein, "polymorphs", "crystalmodification", "crystal form", "crystalline modification", "polymorphic form" and "crystalline form" are understood as synonymous, which are solid crystal forms of complexes, acid addition salts or base addition salts thereof, comprise but are not limited to, single component or multiple component crystals, and/or polymorphs, solvates, hydrates, clathrates, eutectics, salts, solvates of salts, hytrates of salts of compounds.

The term as used herein, "pharmaceutical acceptable acid addition salt" refers to an addition salt formed by the compound of formula (I) or formula (Ia) with an inorganic acid or an organic acid. Suitable inorganic acid salts include, but are not limited to, hydrochloride, sulfate, hydrosulfate, nitrate, hydrobromide, hydriodate, carbonate, hydrocarbonate, sulphite, hydrosulphite, pyrosulfate, monohydric phosphate, dihydric phosphate, perchlorate, persulfate, hemisulphate, bisulfate, thiocyanate, phosphate, pyrophosphate, metaphosphate; suitable organic acid salts include, but are not limited to, formate, acetate, propionate, butyrate, benzoate, malonate, succinate, pyruvate, mesylate, esilate, propanesulfonate, citrate, 4-nitrobenzoate, benzene sulfonate, tosilate, malate, propiolate, 2-tetrolate, 2-hydroxy-ethanesulfonate, vinyl acetate, tartrate, L-tartrate, fumarate, isethionate, maleate, lactate, lactobionate, pamoate, salicylate, mutate, gluceptate, mandelate, 1,2-ethanedisulfonate, 2-naphthalenesulfonate, oxalate, trifluoroacetates, metal triflate, adipate, suberate, sebacate, butyne-1,4-dicarboxylate, hexyne-1,6-dicarboxylate, glycollate, alginate, ascorbate, erythorbate, aspartate, L-aspartate, glutamate, L-glutamate, 2-phenoxybenzoate, 4'-hydroxybenzophenone-2-carboxylate, acetoacetate, 2-hydroxy-ethanesulfonate, benzene sulfonate, borate, chlorobenzoate, camphorate, itaconate, camphorsulfonate, (−)-camphorsulfonate, toluate, dinitrobenzoate, sulfamate, lactobionate, galacturonate, cyclopentylpropionate, dodecylsulfate, acrylate, cypionate, glycerophosphate, methoxybenzoate, digluconate, gluconate, enantate, caproate, 2-hydroxy-ethanesulfonate, pivalate, glucuronate, laurate, phthalate, phenylacetate, lauryl sulfate, 2-acetoxybenzoate, nicotinate, cinnamate, oleate, palmitate, pamoate, pectate, phthalate, glutarate, hydroxymaleate, hydroxybenzoate, phenylacetate, 3-hydroxy-2-naphthoate, 3-phenylpropionate, isobutyrate, pivalate, picrate, pivalate, stearate, 2,2-dichloroacetate, acylation amino acid salt, alginate, 4-acetamidobenzenesulfonate, decanoate, cholate, caprylate, pelargonate, cyclamate, phthalate, cysteine hydrochloride, sorbate, pamoate, galactarate, glycine hydrochloride, naphthalenedisulfonate, xylene sulfonate, cystamine dihydrochloride, undecanoate, polyvinyl sulfonate, sulfosalicylate, phenylbutyrate, 4-hydroxybutyrate, polyvinylsulfate, 1-naphthalenesulfonate, 2-naphthalenesulfonate and valerate.

The term as used herein, "pharmaceutical acceptable base addition salt" refers to an addition salt formed by the compound of formula (I) or formula (Ia) with a base. Suitable base addition salts include, but are not limited to, a lithium salt, a sodium salt, a potassium salt, a calcium salt, a magnesium salt, a aluminium salt, a iron salt, a ferrous salt, a manganese salt, a manganous salt, a cupric salt, a zinc salt and an ammonium salt; or, the base addition salt is formed by the compound of formula (I) or formula (Ia) with a base selected from methylamine, dimethylamine, trimethylamine, ethylamine, diethylamine, triethylamine, isopropylamine, 2-ethylaminoethanol, pyridine, methylpyridine, ethanolamine, diethanolamine, ammonium, tetramethyl ammonium, tetraethylammonium, triethanolamine, piperidine, piperazine, morpholine, lysine, arginine, L-arginine, histidine, L-histidine, N-methylglucamine, dimethylglucamine, ethylglucamine, dicyclohexylamine, 1,6-hexamethylenediamine, glucamine, betaine, caffeine, choline, 2-diethylaminoethanol, 2-dimethylaminoethanol, aminoethanol, N-ethylmorpholine, glucosamine, isopropylamine, methylglucamine, polyamine resin, procaine, theobromine, tripropylamine, trometamol, glycine, sarcosine, serinol, tris(hydroxymethyl)aminomethane, aminopropanediol, 1-amino-2,3,4-butanetriol, L-lysine and ornithine.

The term "crystalline form" refers to a solid having a highly regular chemical structure, includes, but is not limited to, a single component or multiple component crystal, and/or a polymorph, a solvate, a hydrate, a clathrate, a co-crystal, a salt, a solvate of salts, a hydrate of salts. Crystalline forms of a substance can be obtained by a number of methods, as known in the art. Such methods include, but are not limited to, melt crystallization, melt cooling, solvent crystallization, crystallization in confined spaces, such as in nanopores or capillaries, crystallization on surfaces or templates, such as on polymers, crystallization in the presence of additives, e.g. co-crystal counter-molecules, desolvation, dehydration, rapid evaporation, rapid cooling, slow cooling, vapor diffusion, sublimation, reaction crystallization, anti-solvent addition, grinding and solvent-drop grinding, etc.

"Amorphism" or "amorphous form" refers to substance forming by particle (such as molecule, atom, ion) arranged in no periodic in three-dimensional space, which is characterized by a diffused X-ray powder diffraction pattern with no sharp peaks. Amorphism is a special physical form of solid substance, the ordered structural characteristics in a part of amorphous substance imply there are innumerable links between amorphous substance and crystal substance. Amorphous substance can be obtained through many methods as known in the art. These methods include, but are not limited to, rapid freezing method, anti-solvent flocculence method, ball-milling method, spray drying method, freeze-drying method, wet granulating method and solid dispersion technique, and the like.

The term "solvent", as used herein, refers to a substance (typically a liquid), that is capable of completely or partially dissolving another substance (typically a solid). Solvents used herein conclude, but are limited to: water, acetic acid, ethyl ether, isopropyl ether, petroleum ether, isopropyl acetate, n-propyl acetate, methyl tert-butyl ether and heptane, an ethanol-water mixture at a volume ratio from 10:90 to 90:10, acetone, acetonitrile, benzene, chloroform, carbon tetrachloride, dichloromethane, dimethyl sulfoxide, 1,4-dioxane, ethanol, ethyl acetate, n-butanol, tert-butanol, N,N-dimethyl acetamide, N,N-dimethyl formamide, formamide, formic acid, hexane, iso-propanol, methanol, methyl ethyl ketone, 1-methyl-2-pyrrolidone, mesitylene, nitromethane, polyethylene glycol, n-propanol, 2-acetone, pyridine, tetrahydrofuran, methyl ethyl ketone, toluene, xylene, mixtures thereof, and the like.

The term "anti-solvent" refers to a fluid which promotes precipitation from the solvent of the product (or a precursor for the product). The anti-solvent may comprise a cold gas, or a fluid promoting the precipitation via a chemical reaction, or a fluid which decreases the solubility of the product in the solvent; it may be the same liquid as the solvent but at a different temperature or it may be a different liquid from the solvent.

The term "solvate," as used herein, means there is a solvent on the surface, in the lattice or on the surface and in the lattice, the solvent may be water, acetic acid, n-propyl acetate, acetone, acetonitrile, benzene, chloroform, tetrachloromethane, dichloromethane, dimethyl sulfoxide, 1,4-dioxane, ethanol, ethyl acetate, butanol, tert-butanol, N,N-dimethylacetamide, N,N-dimethylformamide, formamide, formic acid, heptane, hexane, isopropanol, methanol, methylethylketone, methylpyrrolidone, mesitylene, nitromethane, polyethylene glycol, propanol, 2-acetone, pyridine, tetrahydrofuran, toluene, xylene, mixtures thereof, and the like. A specific example of a solvate is a hydrate, wherein the solvent on the surface, in the lattice or on the surface and in the lattice, is water. Hydrates may or may not have solvents other than water on the surface, in the lattice or on the surface and in the lattice of a substance.

Crystalline form or amorphism can be identified through multiple technological means, such as X-ray powder diffraction (XRPD), infrared spectroscopy (IR), melting point method, differential scanning calorimetry (DSC), thermogravimetry analysis (TGA), nuclear magnetic resonance method, Raman spectroscopy, X-ray single crystal diffraction, solution calorimetry, scanning electron microscope (SEM), quantitative analysis, solubility, dissolution velocity, etc.

The complex, acid addition salt or base addition salt disclosed herein or the crystalline form thereof may comprises a solvent. In some cases, a solvent contained in complexes, acid addition salts, base addition salts or the crystalline form thereof assists in the internal stability, and common solvents include water, ethanol, methanol, isopropanol, n-propyl acetate, tetrahydrofuran, acetone, isopropyl ether, ether, isopropyl acetate, n-heptane, ethyl acetate, and the like. Complexes, acid addition salts, base addition salts or the crystalline form thereof containing a certain amount of water or other solvents, which have any feature of the complex, the acid addition salt, the base addition salt or the crystalline form thereof disclosed herein, are intended to be considered within the scope of the invention.

Some information such as change in crystalline form, crystallinity, crystal structure state, etc., can be obtained through detection of X-ray powder diffraction (XRPD) which is a common method used for identifying crystalline form. The peak position of XRPD pattern mainly depends on the crystal structure, which is relatively insensitive to experimental details, and the relative peak height depends on many factors related to sample preparation and the geometry of the instrument. Thus, in some embodiments, the crystalline form disclosed herein is characterized by an X-ray powder diffraction pattern having some peaks in certain positions, which is substantially the same as the XRPD pattern provided in appended figures of the present invention. Meanwhile, the measurement of 2θ in XRPD pattern could have some experimental errors, for example the measurements of 2θ in XRPD pattern could be slightly different because of different instruments and different samples. Therefore, the value of 2θ is not absolute. According to the state of the instrument for the experiment disclosed herein, the error margin in 2θ of the diffraction peak is ±0.2°.

Differential scanning calorimetry (DSC) is a technology used for measuring the energy difference between a sample and a inert reference compound (usually α-$Al_2O_3$) as a function of temperature, which is performed through constant heating or cooling under program control. The melting peak height of DSC thermogram depends on many factors related to sample preparation and the geometry of the instrument, and the peak position is relatively insensitive to experimental details. Thus, in some embodiments, the crystalline form disclosed herein is characterized by a DSC thermogram having some peaks in certain positions, which is substantially the same as the DSC thermogram provided in appended figures of the present invention. Meanwhile, a DSC thermogram could have some experimental errors, for example the peak position and the peak value in the DSC thermogram could be slightly different because of different instruments and different samples. Therefore, the peak position and the peak value in the DSC thermogram are not absolute. According to the state of the instrument for the experiment disclosed herein. The error margin in the melting peaks is ±3° C.

Glass transition refers to a transition of amorphous substances between elastomeric state and glassy state, which is an inherent property of the substance; the corresponding transition temperature is glass transition temperature (Tg), which is an important physical property of amorphous substances. Glass transition is a phenomenon related to the molecular motion. Therefore, glass transition temperature (Tg) mainly depends on the structure of a substance, and relatively insensitive to experimental details. According to the state of the instrument for the experiment disclosed herein. The error margin in the melting peaks is ±3° C.

Differential scanning calorimetry (DSC) also is used for detection and analysis whether there is crystal transformation or mixed grain phenomenon in crystalline form.

Solids having same chemical composition usually form polymorphs, or called variant, having different crystal structures under different thermodynamic conditions, this phenomenon is called polymorphism or polyphase. When conditions of temperature and pressure change, there will be a change between variants, which is called crystal transition. The property of crystalline forms changed largely such as mechanics, electrics, magnetics because of crystal transition. The crystal transition process could be observed in differential scanning calorimetry (DSC) thermogram when the transition temperature within a measurable range, which is characterized by the DSC thermogram having a exothermic peak reflecting this transformation and two or more endothermic peaks which respectively are characteristic endothermic peaks of different crystalline forms before and after the transformation.

Thermogravimetric analysis (TGA) is a technology for determining the quantitive change of a substance as a function of temperature under program control, which suitable for detecting the process of the solvent loss in the crystal or sublimation and dissociation of the sample, and the condition of crystal water and crystal solvent contained in crystal may be speculated through analysis of the detection results. The quality change described in TGA curve depends on many factors related to sample preparation and instrument; and the quantitative change detected by TGA could be slightly different because of different instruments and different samples. According to the state of the instrument for the experiment disclosed herein, the error margin of the quality change is ±0.1%.

Raman spectroscopy is a spectrophotometry used for studying vibration mode and rotation mode of molecules and other low frequency mode in one system. Different spatial structures of the same molecule have different Raman activities. Therefore, Raman spectroscopy could be used for determining and identifying crystalline form or amorphism. The peak position of Raman spectroscopy mainly relates to the structure of substances, which is relatively insensitive to experimental details, and the peak intensity depends on factors such as sample preparation and instrument. Thus, in some embodiments, the crystalline form or amorphism disclosed herein is characterized by a Raman spectrogram having characteristic peaks in certain position, which is substantially the same as the Raman spectrogram provided in appended figures of the present invention. Meanwhile, a Raman spectrogram could have some experimental errors, the peak position and the peak value in the Raman spectrogram could be slightly different because of different instruments and different samples. Therefore, the peak position and the peak value in the Raman spectrogram are not absolute. According to the state of the instrument for the experiment disclosed herein, the error margin of the absorption peaks is ±2 $cm^{-1}$.

The bond length and the bond angle of certain chemical bonds in different spatial structures of the same molecule are different, which leads to different energy levels of vibration-rotational transition of the molecule and differences in the main characteristics of the corresponding infrared spectroscopy such as frequency of absorption band, peak shape, peak position, peak intensity, and so on. Thus, in some embodiments, the crystalline form or amorphism disclosed herein is characterized by a Fourier infrared (FT-IR) spectrogram having characteristic peaks in certain position, which is substantially the same as the Fourier infrared spectrogram provided in appended figures of the present invention. Meanwhile, a Fourier infrared spectrogram could have some experimental errors, the peak position and the peak value in the Fourier infrared spectrogram could be slightly different because of different instruments and different samples. Therefore, the peak position and the peak value in the Fourier infrared spectrogram are not absolute. According to the state of the instrument for the experiment disclosed herein, the error margin of the absorption peaks is ±2 $cm^{-1}$.

As used herein, the value of 2θ described in an X-ray powder diffraction pattern is recorded in degree (°).

As used herein, the term "substantially the same as shown in a figure" refers to an X-ray powder diffraction (XRPD) pattern, or a differential scanning calorimetry (DSC) thermogram, or a Raman spectrogram, or a Fourier transform infrared spectrogram has at least 50%, at least 60%, at least 70%, at least 80%, at least 90%, at least 95%, or at least 99% of the peaks shown in the figure.

As used herein, when referring to a spectrum and/or to data presented in a figure, the term "peak" refers to a feature that one skilled in the art would recognize and would not be attributed to background noise.

As used herein, the term "substantially pure" refers to a crystalline form that is substantially free of one or more other crystalline forms, i.e., the crystalline form has a purity of at least about 80%, at least about 85%, at least about 90%, at least about 93%, at least about 95%, at least about 98%, at least about 99%, at least about 99.5%, at least about 99.6%, at least about 99.7%, at least about 99.8%, or at least about 99.9%; or the crystalline form comprises other crystalline forms, and the percentage of the other crystalline forms in total volume or total weight is less than 20%, less than 10%, less than 5%, less than 3%, less than 1%, less than 0.5%, less than 0.1%, or less than 0.01%.

As used herein, the term "substantially free" refers to the percentage of one or more other crystalline forms in total volume or total weight is less than 20%, less than 10%, less than 5%, less than 4%, less than 3%, less than 2%, less than 1%, less than 0.5%, less than 0.1%, or less than 0.01%.

As used herein, the term "relative intensity" refers to the ratio of intensity between other peaks and the strongest peak when the intensity of the strongest peak among all diffraction peaks is 100% in the X-ray powder diffraction (XRPD) pattern.

As used in the context of the present invention, regardless of whether the word "about" is used, which means within 10%, suitably within 5% and particularly within 1% of a given value or range. Alternatively, the term "about" means within an acceptable standard error of the mean for those of ordinary skill in the art. Therefore, whenever a number having a value N is disclosed, any number having the value within N+/−1%, N+/−2%, N+/−3%, N+/−5%, N+/−7%, N+/−8% or N+/−10% is specifically disclosed, wherein "+/−" refers to plus or minus.

Unless otherwise stated, structures depicted herein are also meant to include all isomeric (e.g., enantiomeric, diastereomeric, and geometric (or conformational) forms of the structure: for example, the R and S configurations for each asymmetric center, (Z) and (E) double bond isomers, and (Z) and (E) conformational isomers. Therefore, single stereochemical isomers as well as enantiomeric, diastereomeric, or geometric mixtures of the present compounds are within the scope disclosed herein.

Unless otherwise stated, all tautomeric forms of the compounds disclosed herein are within the scope of the invention. Additionally, unless otherwise stated, structures depicted herein are also meant to include compounds that differ only in the presence of one or more isotopically enriched atoms. Isotopically enriched compounds have the structure of the present invention, but for the fact that one or more atoms are replaced by an atom having an selected atomic mass or mass number. Examples of isotopes that can be incorporated into compounds of the invention include isotopes of hydrogen, carbon, nitrogen, oxygen, phosphorous, sulfur, fluorine and chlorine, such as $^2H$, $^3H$, $^{11}C$, $^{13}C$, $^{14}C$, $^{15}N$, $^{17}O$, $^{18}O$, $^{18}F$, $^{31}P$, $^{32}P$, $^{35}S$, $^{36}Cl$ and $^{125}I$.

In another aspect, the compounds of the invention include isotopically enriched compounds as defined herein, for example, wherein radioisotopes exist, such as $^3H$, $^{14}C$ and $^{18}F$, or wherein non-radioactive isotopes exist, such as compounds of $^2H$ and $^{13}C$. Such isotopically enriched compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. 18F-enriched compounds are particularly desirable for PET or SPECT studies. Isotopically-enriched compounds of Formula (I) or (Ia) can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^2H$ or D) may afford certain therapeutic advantages resulting from greater metabolic stability. For example, increased in vivo half-life or reduced dosage requirements or an improvement in therapeutic index. It is understood that deuterium in this context is regarded as a substituent of a compound of Formula (I) or (Ia). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Pharmaceutically acceptable solvates in accordance with the invention include those wherein the solvent of crystallization may be isotopically substituted, e.g. $D_2O$, $d_6$-acetone, DMSO-$d_6$.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley&Sons, Inc., New York, 1994. The compounds disclosed herein may contain asymmetric or chiral centers, and therefore exist in different stereoisomeric forms. It is intended that all stereoisomeric forms of the compounds disclosed herein, including, but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (±) and (−) are employed to designate the sign of rotation of plane-polarized light by the compound, with (−) or l meaning that the compound is levorotatory. A compound prefixed with (±) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The term "racemic mixture" or "racemate" refers to an equimolar mixture of two enantiomeric species, devoid of optical activity.

As described above, the pharmaceutically acceptable compositions disclosed herein further comprise a pharmaceutically acceptable carrier, an adjuvant, or a excipient, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. As described in the following documents: In Remington: The Science and Practice of Pharmacy, 21st edition, 2005, ed. D. B. Troy, Lippincott Williams& Wilkins, Philadelphia, and Encyclopedia of Pharmaceutical Technology, eds. J. Swarbrick and J. C. Boylan, 1988-1999, Marcel Dekker, New York, both of which are herein incorporated by reference in their entireties, discloses various carriers used in formulating pharmaceutically acceptable compositions and known techniques for the preparation thereof. Except insofar as any conventional adjuvant incompatible with the compounds disclosed herein, such as by producing any undesirable biological effect or otherwise interacting in a deleterious manner with any other components of the pharmaceutically acceptable composition, its use is contemplated to be within the scope of this invention.

Complexes, acid addition salts or base addition salts of the compound disclosed herein or pharmaceutical compositions thereof are suitable for the treatment of acute and chronic viral infections of infectious hepatitis, particularly can inhibit hepatitis B virus (HBV) effectively, and suitable for treating or lessening diseases induced by viruses in a patient, especially acute and chronic persistent HBV infections. Chronic viral diseases induced by HBV can worsen the morbidity and the chronic HBV infection can cause cirrhosis of liver and/or henatocellular canceration in many cases.

Some non-limiting examples of materials which can serve as pharmaceutically acceptable adjuvants include, but are not limited to carriers such as ion exchangers; aluminium; aluminum stearate; lecithin; serum albumins such as human serum albumin; buffer substances such as phosphates; glycine; sorbic acid; potassium sorbate; partial glyceride mixtures of saturated vegetable fatty acids; water; salts or electrolytes such as protamine sulfate, disodium hydrogen phosphate, potassium hydrogen phosphate, sodium chloride and zinc salts; colloidal silica; magnesium trisilicate; polyvinyl pyrrolidone; polyacrylates; waxes; polyethylene-polyoxypropylene-block polymers; wool fat; sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; oils such as peanut oil, cottonseed oil, safflower oil, sesame oil, olive oil, corn oil and soybean oil; glycols such as propylene glycol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; phosphate buffer solutions; as well as other non-toxic compatible lubricants such as sodium lauryl sulfate and magnesium stearate; coloring agents; releasing agents; coating agents; sweetening, flavoring; perfuming agents; preservatives and antioxidants; excipients such as binding agents such as syrup, Arabic gum, sorbitol, tragacanth or polyvinyl pyrrolidone and diluents.

The pharmaceutical composition of complexes, acid addition salts or base addition salts of the compound disclosed herein may be administered in any of the following routes: orally, inhaled by spray, rectally, nasally, locally, vaginally, parenterally such as subcutaneous, intravenous, intramuscular, intraperitoneal, intrathecal, intraventricular, intrasternal, or intracranial injection or infusion, or administered with the aid of an explanted reservoir. Administration routes by orally, intramuscular, intraperitoneal or intravenous injection are preferred.

Complexes, acid acid addition salts or base addition salts of compounds disclosed herein or the pharmaceutical acceptable composition thereof may be administered in a unit dosage form. The dosage form may be in a liquid form, or a solid form. The liquid form includes true solutions, colloids, particulates, suspensions. Other dosage forms include tablets, capsules, dropping pills, aerosols, pills, powders, solutions, suspensions, emulsions, granules, suppositories, freeze-dried powder injection, clathrates, implants, patches, liniments, and the like.

Oral tablets and capsules may comprise excipients, e.g., binders, such as syrup, Arabic gum, sorbitol, tragacanth or polyvinylpyrrolidone; fillers, such as lactose, sucrose, corn starch, calcium phosphate, sorbitol, glycine; lubricants such as magnesium stearate, talc, polyethylene glycol, silica; disintegrating agents, such as potato starch; or acceptable moisturizing agents such as sodium lauryl sulfate. Tablets may be coated by using known methods in pharmaceutics.

Oral solution may be made as a suspension of water and oil, a solution, an emulsion, syrup or an elixir, or made as a dried product to which water or other suitable medium is added before use. This liquid preparation may comprise conventional additives, e.g., suspending agents such sorbitol, cellulose methyl ether, glucose syrup, gel, hydroxyethyl cellulose, carboxymethyl cellulose, aluminum stearate gel, hydrogenated edible greases; emulsifying agents such as lecithin, sorbitan monoleate, Arabic gum; or non-aqueous carriers (possibly including edible oil), such as almond oil, grease such as glycerin, ethylene glycol, or ethanol; antiseptics such as methyl or propyl p-hydroxybenzoate, sorbic acid. If desired, a flavoring agent or a colorant may be added.

Suppositories may comprise a conventional suppository base, such as cocoa butter or other glyceride.

For parenteral administration, the liquid dosage form is usually made from the compound and a sterilized carrier. The preferred carrier is water. According to the difference of selected carrier and drug concentration, the compound can be either dissolved in the carrier or made into a supernatant solution. When being made into a solution for injection, the compound is firstly dissolved in water, and then filtered and sterilized before being packaged into an sealed bottle or an ampoule.

For application topically to the skin, the compound disclosed herein may be made into a suitable form of ointments, lotions or creams, wherein the active ingredient is suspended or dissolved in one or more carrier(s). Wherein carriers used for an ointment preparation include, but are not limited to: mineral oil, liquid vaseline, white vaseline, propylene glycol, polyoxyethylene, polyoxypropylene, emulsified wax and water; carriers used for a lotion and a cream include, but are not limited to: mineral oil, sorbitan monostearate, Tween 60, cetyl ester wax, hexadecylene aromatic alcohol, 2-octyl dodecanol, benzyl alcohol and water.

In general, it has proved to be advantageous in either human medicine or veterinary medicine, the total administrated dose of the active compound disclosed herein is about 0.5 to 500 mg every 24 hours, preferably 1 to 100 mg/kg body weight. If appropriate, the drug is administrated in single dose for multiple times, to achieve the desired effect. The amount of the active compound in a single dose is preferably about 1 to 80 mg, more preferably 1 to 50 mg/kg body weight. Nevertheless, the dose may also be varied according to the kind and the body weight of treatment objects, the nature and the severity of diseases, the type of preparations and the method of administration of drugs, and administration period or time interval.

The pharmaceutical composition provided herein further comprises anti-HBV drugs, and the anti-HBV drug is an HBV polymerase inhibitor, immunomodulator or interferon.

The HBV agent is lamivudine, telbivudine, tenofovir, entecavir, adefovir dipivoxil, alfaferone, alloferon, celmoleukin, clevudine, emtricitabine, famciclovir, feron, hepatect CP, intefen, interferon α-1b, interferon α, interferon α-2α, interferon β-1a, interferon α-2, interleukin-2, mivotilate, nitazoxanide, peginterferon alfa-2a, ribavirin, roferon-A, sizofiran, euforavac, veldona, rintatolimod, phosphazid, heplisav, interferon α-2b, levamisole, or propagermanium, and the like.

In another aspect, provided herein is a use of complexes, acid addition salts or base addition salts or pharmaceutical compositions of compounds disclosed herein in the manufacture of a medicament for preventing, managing, treating or lessening HBV diseases in a patient, comprising administering a pharmaceutically acceptable effective amount to a patient. The HBV disease is a hepatic disease caused by hepatitis B virus infection or hepatitis B infection, including acute hepatitis, chronic hepatitis, cirrhosis and hepatocellular carcinoma. The symptoms of acute hepatitis B virus infection may be asymptomatic or manifested as acute hepatitis symptoms. A patient with chronic virus infection suffers an active disease, which can progress to cirrhosis and liver cancer.

GENERAL SYNTHETIC PROCEDURES

Figure 1:
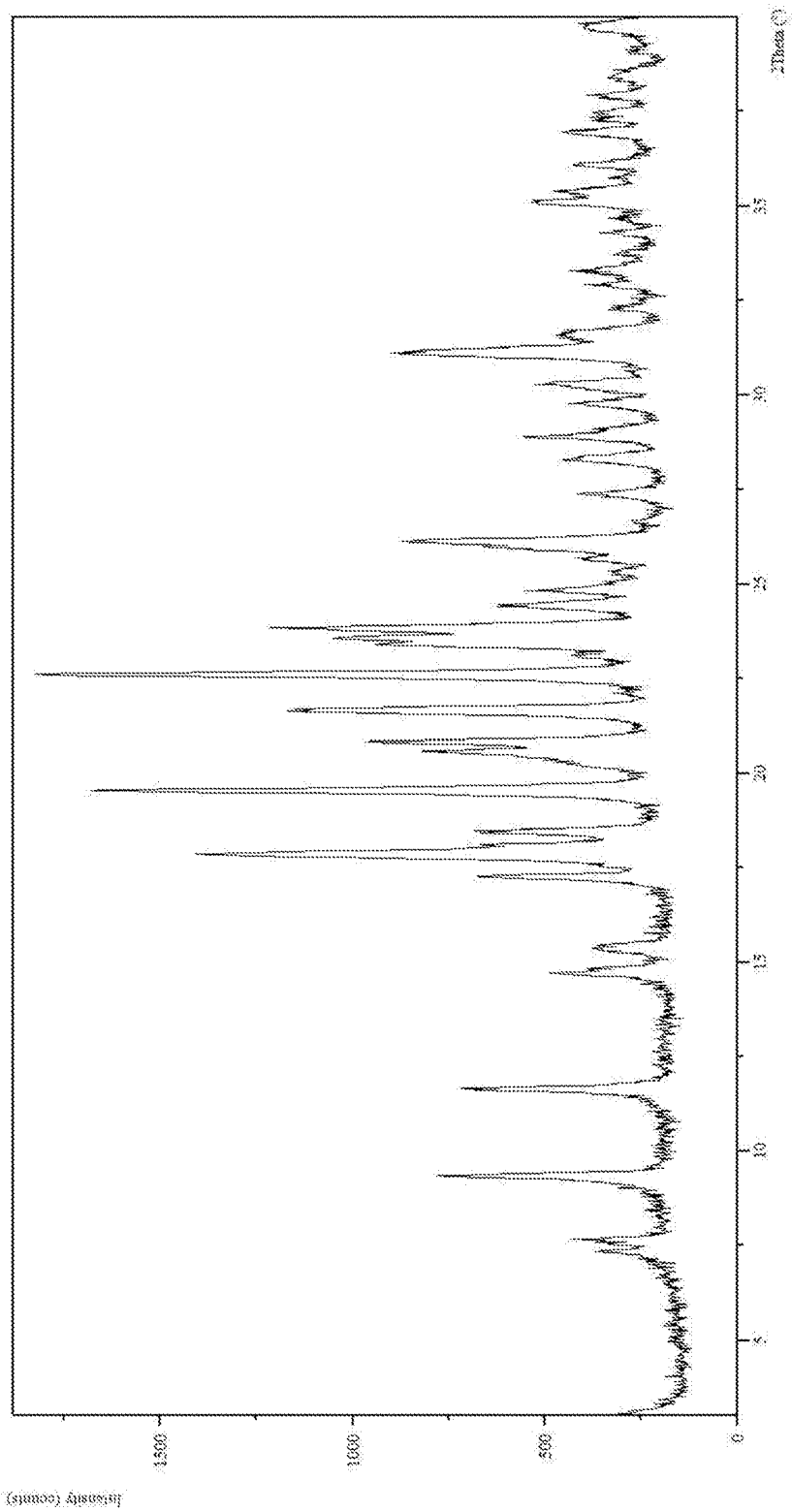
FIG. 1 provides an X-ray powder diffraction (XRPD) pattern of the complex having crystalline form I(A) of L-tartaric acid and the compound of formula (Ia).

In the examples described below, unless otherwise indicated all temperatures are set forth in degrees Celsius (° C.). Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Qingdao Tenglong Reagent Chemical Ltd. and Qingdao Ocean Chemical Factory.

$^1$H NMR spectra were recorded by a Bruker Avance 400 MHz spectrometer or Bruker Avance III HD 600 spectrometer, using CDCl$_3$, DMSO-d$_6$, CD$_3$OD or d$_6$-acetone (reported in ppm) as the solvent, and using TMS (0 ppm) or chloroform (7.25 ppm) as the reference standard. When peak multiplicities are reported, the following abbreviations are used: s (singlet), s, s (singlet, singlet), d (doublet), t (triplet), m (multiplet), br (broadened), dd (doublet of doublets), ddd (doublet of doublet of doublets), dt (doublet of triplets), ddt (doublet of doublet of triplets), td (triplet of doublets) and br.s (broadened singlet). Coupling constants, when given, were reported in Hertz (Hz).

The X ray powder diffraction analysis method disclosed herein is: X-ray powder diffraction diagram was recorded on an Empyrean diffraction using Cu-Kα radiation (45 KV, 40 mA). A thin layer was prepared from powder sample on the single-crystal silicon sample holder, and which was put on a rotary sample stage and analyzed in the range from 3° to 400 with a 0.01680 step size. Data were collected by Data Collector software, and processed by HighScore Plus software, read by Data Viewer software.

The differential Scanning Calorimetry (DSC) analysis method disclosed herein is: Differential scanning calorimetry thermogram was recorded on a TA Q2000 module with a thermoanalysis controller. The data was collected and analyzed by TA Instruments Thermal Solutions software. About 1-5 mg sample was weighed accurately in a special aluminium crucible with a lid, and heated using a linear heating device in 10° C./minute and analysed from room temperature to about 250° C. DSC cabin was purged with dry nitrogen during use.

The thermogravimetric Analysis (TGA) method disclosed herein is: Thermogravimetric curve was recorded on a TA Q500 module with a thermoanalysis controller. The data were collected, and analyzed by TA Instruments Thermal Solutions software. About 110 mg sample was weighed accurately in a special aluminium crucible with a lid, and heated using a linear heating device in 10° C./minute and analysed from room temperature to about 300° C. TGA oven chamber was purged with dry nitrogen during use.

The Raman spectrum analysis method disclosed herein is: Raman spectrogram was recorded on a Thermo DXR confocal laser Raman spectrometer. The data were collected and analyzed by MONIC software. The laser wavelength is 780 nm, the laser energy is 24 Mw, the detection range is from 3500 $cm^{-1}$ to 50 $cm^{-1}$, the scan times is 20 times, the resolution ratio is from 4.7 $cm^{-1}$ to 8.7 $cm^{-1}$.

The Fourier transform infrared spectrum (FT-IR) analysis method disclosed is: Fourier transform infrared spectrogram was recorded on TENSOR27 Germanic Bruker infrared spectrometer. The data were collected and analyzed by OPUS software. KBr disk was prepared, the scan times are 16 times, the wave number range is from 4000 $cm^{-1}$ to 400 $cm^{-1}$, the resolution is from 2 $cm^{-1}$.

Single crystal x-ray diffraction analysis method: Data were collected on an Agilent Technologies Gemini A Ultra serial diffractometer using Cu Kα radiation (λ=1.5418 Å). Indexing and processing of the measured intensity data were carried out with CrysAlis PRO procedure. The structure was solved by direct methods using SHELX-97 (Sheldrick, G. M. SHELXTL-97, Program for Crystal Structure Solution and Refinement; University of Gottingen: Gottingen, Germany, 1997). The derived atomic parameters (coordinates and temperature factors) were refined through full matrix least-squares. The function minimized in the refinements was $\Sigma_w(|F_o|-|F_c|)^2$. R is defined as $\Sigma||F_o|-|F_c||/\Sigma|F_o|$, while $R_w=[\Sigma_w (|F_o-F_c|)^2/\Sigma_w|F_o|_2]^{1/2}$ where w is an appropriate weighting function based on errors in the observed intensities. Difference maps were examined at all stages of refinement. The positions of hydrogens on nitrogen and oxygen were located in Fourier difference electron density maps. All the other hydrogen atoms were placed in calculated positions with fixed isotropic thermal parameters and included in the structure factor calculations in the final stage of full-matrix least-squares refinement. Simulated powder X-ray patterns were generated using Mercury procedure. Single crystal was selected by measuring 0.4×0.38×0.23 mm Single Crystal by single crystal diffraction analysis. The selected crystal was affixed to a thin glass fiber with a small amount of a light baseline, and mounted on a Gemini A Ultra single crystal diffractometer (Agilent Technologies).

The solubility disclosed herein was measured by Aglient 1200 high performance liquid chromatograph VWD detector. The chromatographic column model is Waters Xbridge-C18 (4.6×150 mm, 5 m). The detection wavelength was 250 nm, the flow rate was 1.0 mL/minute, the column temperature was 35° C., the mobile phase was acetonitrile water (v/v=40/60).

Low-resolution mass spectral (MS) data were determined by an Agilent 6320 Series LC-MS spectrometer equipped with a G1312A binary pump and a G1316A TCC (column was operated at 30° C.). G1329A autosampler and G1315B DAD detector were applied in the analysis, and an ESI source was used in the LC-MS spectrometer.

Low-resolution mass spectral (MS) data was determined by an Agilent 6120 Series LC-MS spectrometer equipped with a G1312A binary pump and a G1316A TCC (column was operated at 30° C.). G1329A autosampler and G1315B DAD detector were applied in the analysis, and an ESI source was used in the LC-MS spectrometer.

Both LC-MS spectrometers were equipped with an Agilent Zorbax SB-C18, 2.1×30 mm, 5 m column. Injection volume was decided by the sample concentration. The flow rate was 0.6 mL/minute. The HPLC peaks were recorded by UV-Vis wavelength at 210 nm and 254 nm. The mobile phase was 0.1% formic acid in $CH_3CN$ (phase A) and 0.1% formic acid in ultrapure water (phase B). The gradient elution conditions were showed in Table 1:

TABLE 1

The gradient condition of the mobile phase in Low-resolution mass spectrum analysis

| Time (minute) | A ($CH_3CN$, 0.1% HCOOH) | B ($H_2O$, 0.1% HCOOH) |
|---|---|---|
| 0-3 | 5-100 | 95-0 |
| 3-6 | 100 | 0 |
| 6-6.1 | 100-5 | 0-95 |
| 6.1-8 | 5 | 95 |

Purities of compounds were assessed by Agilent 1100 Series high performance liquid chromatography (HPLC) with UV detection at 210 nm and 254 nm (Zorbax SB-C18, 2.1×30 mm, 4 μm, 10 minutes, 0.6 mL/minute flow rate, 5 to 95% (0.1% formic acid in $CH_3CN$) in (0.1% formic acid in $H_2O$). Column was operated at 40° C.

Purification of compounds by preparative chromatography was implemented by Agilent 1260 Series high performance liquid chromatography (HPLC) with UV detection at 278 nm (Calesil ODS-120, 4.6×250 mm, 120 A, 10 μm), 1.0 mL/minute flow rate, the mobile phase is (10 mM ZnSO4±20 mM L-valine) buffer solution-methanol (V/V=50/50). Column was operated at 30° C.

EXAMPLES

The following examples disclosed herein are presented to further describe the invention. However, these examples should not be used to limit the scope of the invention.

Example 1: Preparation of Amorphous (S)-4-(((R)-6-(2-chloro-4-fluorophenyl)-5-(methoxycarbonyl)-2-(thiazol-2-yl)-3,6-dihydropyrimidin-4-yl)methyl)morpholine-3-carboxylic Acid (I)

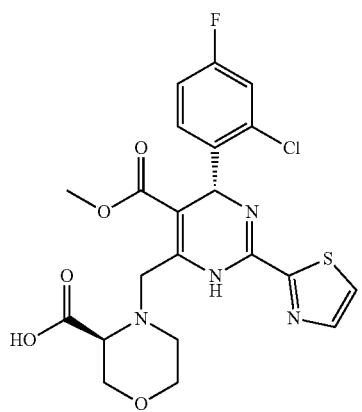

(I)

The compound named (S)-4-(((R)-6-(2-chloro-4-fluorophenyl)-5-(methoxycarbonyl)-2-(thiazol-2-yl)-3,6-dihydropyrimidin-4-yl)methyl)morpholine-3-carboxylic acid was prepared by using the compound named (3S)-4-((6-(2-chloro-4-fluorophenyl)-5-(methoxycarbonyl)-2-(thiazol-2-yl)-3,6-dipyrimidin-4-yl)methyl)morpholine-3-carboxylic acid (10 g, 11.8 mmol) and referring to the process described in Patent WO2014029193 Example 32), which was purified by preparative chromatography to give a yellow foamy solid (3.8 g, productivity: 38%). The compound was characterized by the following spectroscopic data: MS (ESI, pos. ion) m/z: 494.9 [M±H]$^{\pm}$; and $^1$H NMR (400 MHz, DMSO-d$_6$) δ (ppm): 12.52 (br, 1H), 9.86 (s, 1H), 8.03 (d, 1H), 7.94 (d, 1H), 7.43-7.38 (m, 2H), 7.16 (td, 1H), 6.04 (s, 1H), 4.24 (d, 1H), 4.06-3.97 (m, 2H), 3.84 (dd, 1H), 3.73-3.66 (m, 2H), 3.64-3.59 (m, 1H), 3.51 (s, 3H), 3.10-3.06 (m, 1H), 2.43-2.39 (m, 1H).

Example 2: Preparation and Identification of Amorphous (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Tosilate

1. Preparation of Amorphous (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Tosilate To a solution of (S)-4-(((R)-6-(2-chloro-4-fluorophenyl)-5-(methoxycarbonyl)-2-(thiazol-2-yl)-3,6-dihydropyrimidin-4-yl)methyl)morpholine-3-carboxylic acid (100 mg) in isopropyl ether (10 mL) was added a solution of p-toluenesulfonic acid monohydrate (42 mg) in isopropyl acetate (0.5 mL) at 70° C. The resulting mixture was reacted at 70° C. for 15 hours, then cooled down to room temperature and filtered. The filter cake was washed with isopropyl acetate (2.0 mL) and dried in vacuo at 25° C. to give the compound named (S)-4-(((R)-6-(2-chloro-4-fluorophenyl)-5-(methoxycarbonyl)-2-(thiazol-2-yl)-1,6-dihydropyrimidine-4-yl)methyl)morpholine-3-carboxylic acid tosilate as a yellow solid (57 mg, productivity: 42.3%). The compound was characterized by the following spectroscopic data: $^1$H NMR (400 MHz, DMSO-d$_6$) δ (ppm): 8.08 (s, 2H), 7.55-7.41 (m, 4H), 7.21 (d, J=8.0 Hz, 1H), 7.11 (d, J=7.9 Hz, 2H), 6.03 (s, 1H), 4.61 (s, 2H), 4.33 (s, 2H), 4.04 (s, 3H), 3.83 (s, 2H), 3.55 (s, 3H), 2.99 (s, 1H), 2.29 (s, 3H).

Figure 12:
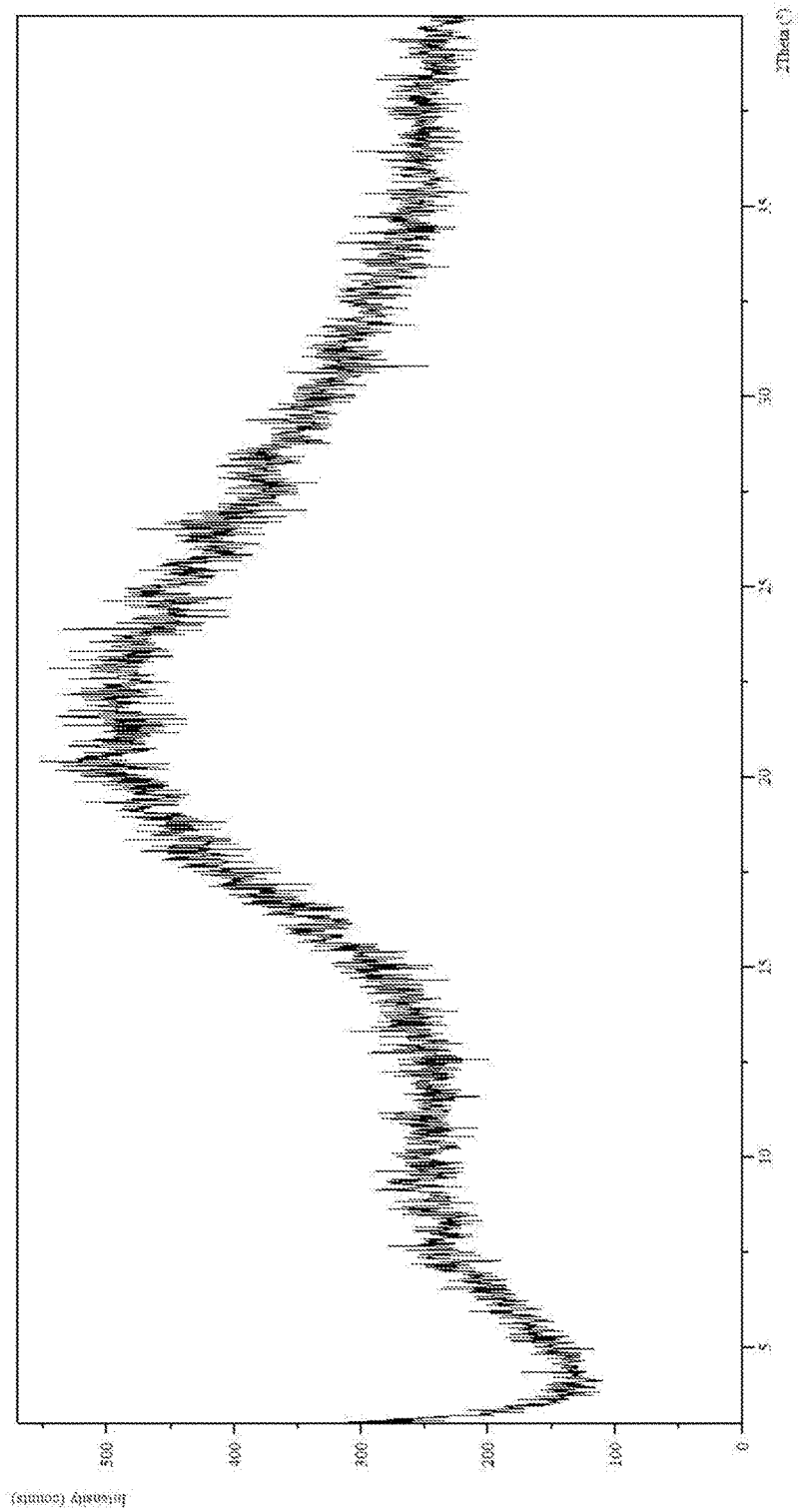
FIG. 12 provides an X-ray powder diffraction (XRPD) pattern of amorphous tosilate of the compound of formula (Ia).

2. Identification of Amorphous (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Tosilate The XRPD pattern was analyzed and identified by using Empyrean X-ray powder diffraction (XRPD) with Cu-Kα radiation, experimental results are shown in FIG. 12.

Example 3: Preparation and Identification of Amorphous (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Salicylate

1. Preparation of Amorphous (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Salicylate

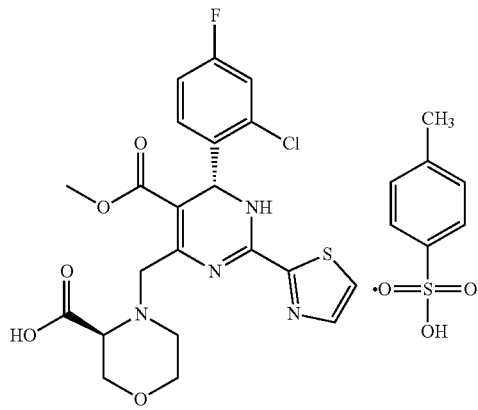

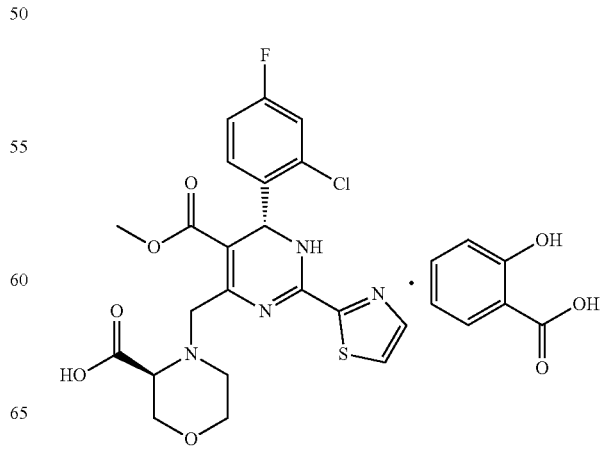

To a solution of (S)-4-(((R)-6-(2-chloro-4-fluorophenyl)-5-(methoxycarbonyl)-2-(thiazol-2-yl)-3,6-dihydropyrimidin-4-yl)methyl)morpholine-3-carboxylic acid (100 mg) in ether (1.5 mL) was added dropwise a solution of salicylic acid (34 mg) in ether (0.5 mL) at room temperature. After the addition, to the mixture was added ether (1.5 mL) and the resulting mixture was warmed and reacted for 22 hours, then the solvent was removed. To the residue was added n-heptane (15 mL). The resulting mixture was stirred for 5 minutes and filtered, and the filter cake was washed with n-heptane (15 mL×2) and dried in vacuo at 25° C. to give the compound named (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic acid salicylate as a yellow solid (75 mg, productivity: 58.6%). The compound was characterized by the following spectroscopic data: $^1$H NMR (400 MHz, DMSO-$d_6$) δ (ppm): 9.86 (s, 1H), 8.02 (d, J=2.8 Hz, 1H), 7.93 (d, J=2.8 Hz, 1H), 7.79 (d, J=7.6 Hz, 1H), 7.50 (t, J=7.5 Hz, 1H), 7.40 (t, J=7.3 Hz, 2H), 7.16 (dd, J=11.5, 5.2 Hz, 1H), 6.92 (dd, J=14.2, 7.7 Hz, 2H), 6.03 (s, 1H), 4.23 (d, J=17.5 Hz, 1H), 4.07-3.93 (m, 2H), 3.87-3.79 (m, 1H), 3.66 (dd, J=23.8, 11.8 Hz, 4H), 3.51 (s, 3H), 3.13-3.03 (m, 1H), 2.56 (s, 1H), 2.41 (d, J=11.8 Hz, 1H).

Figure 20:
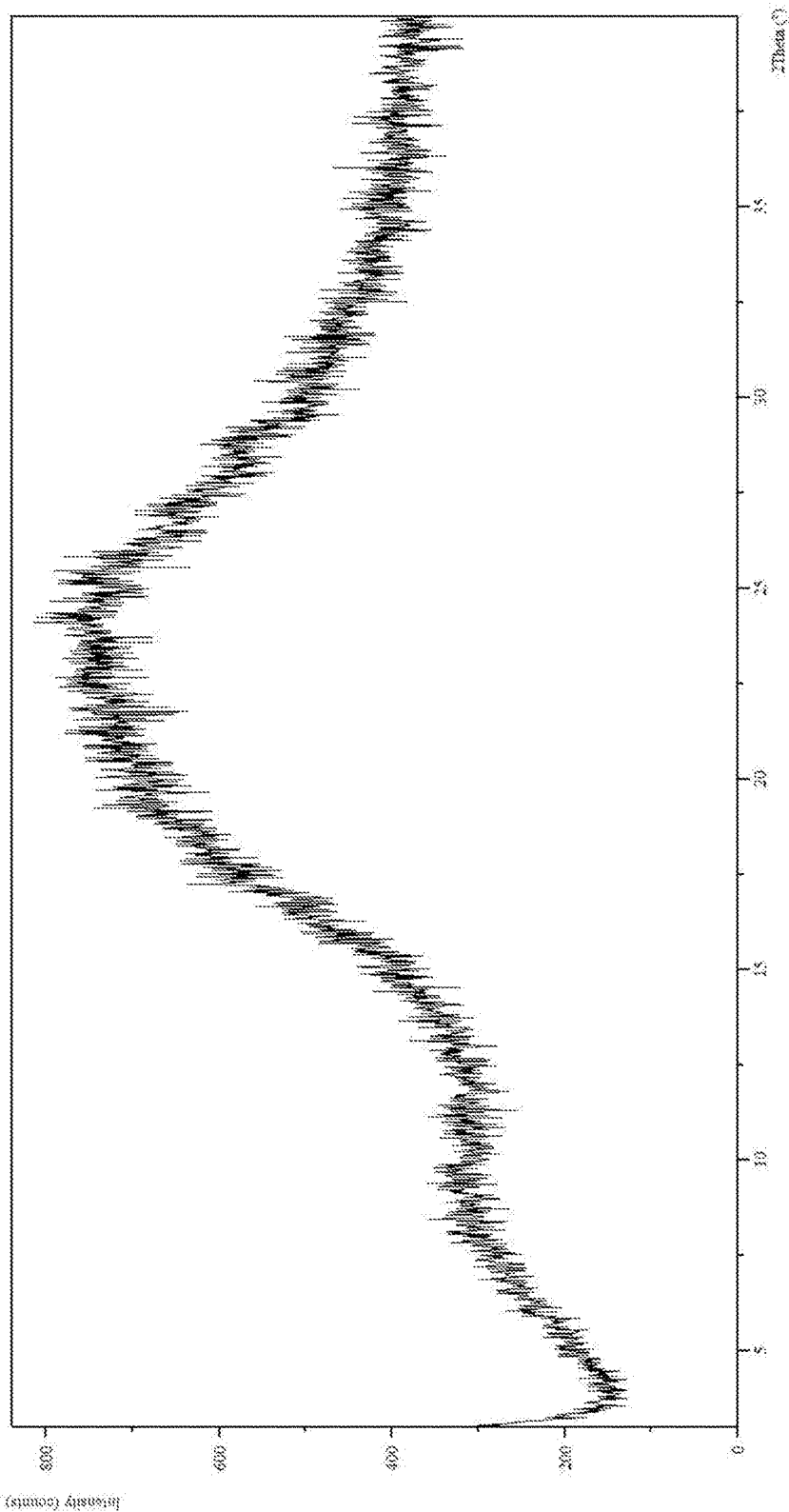
FIG. 20 provides an X-ray powder diffraction (XRPD) pattern of amorphous salicylate of the compound of formula (Ia).

2. Identification of Amorphous (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Salicylate The XRPD pattern was analyzed and identified by using Empyrean X-ray powder diffraction (XRPD) with Cu-Kα radiation, experimental results are shown in FIG. 20.

Example 4: Preparation and Identification of Amorphous (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Benzene Sulfonate 1. Preparation of Amorphous (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Benzene Sulfonate To a solution of (S)-4-(((R)-6-(2-chloro-4-fluorophenyl)-5-(methoxycarbonyl)-2-(thiazol-2-yl)-3,6-dihydropyrimidin-4-yl)methyl)morpholine-3-carboxylic acid (101 mg) in isopropyl ether (10 mL) was added a solution of benzenesulfonic acid (38 mg) in isopropyl acetate (0.5 mL) at 70° C. After the addition, the resulting mixture was warmed and reacted for 15 hours, then cooled down to room temperature and filtered. The filter cake was washed with isopropyl acetate (2.0 mL) and dried in vacuo at 25° C. to give the compound named (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic acid benzene sulfonate as a yellow solid (80 mg, productivity: 60.3%). The compound was characterized by the following spectroscopic data: $^1$H NMR (400 MHz, DMSO-$d_6$) δ (ppm): 8.08 (s, 2H), 7.60 (dd, J=7.2, 1.9 Hz, 2H), 7.47 (dd, J=17.8, 7.6 Hz, 2H), 7.36-7.26 (m, 3H), 7.20 (t, J=8.4 Hz, 1H), 6.03 (s, 1H), 4.65 (s, 2H), 4.36 (s, 2H), 4.05 (s, 2H), 3.85 (s, 3H), 3.55 (s, 3H), 3.05 (s, 1H).

Figure 11:
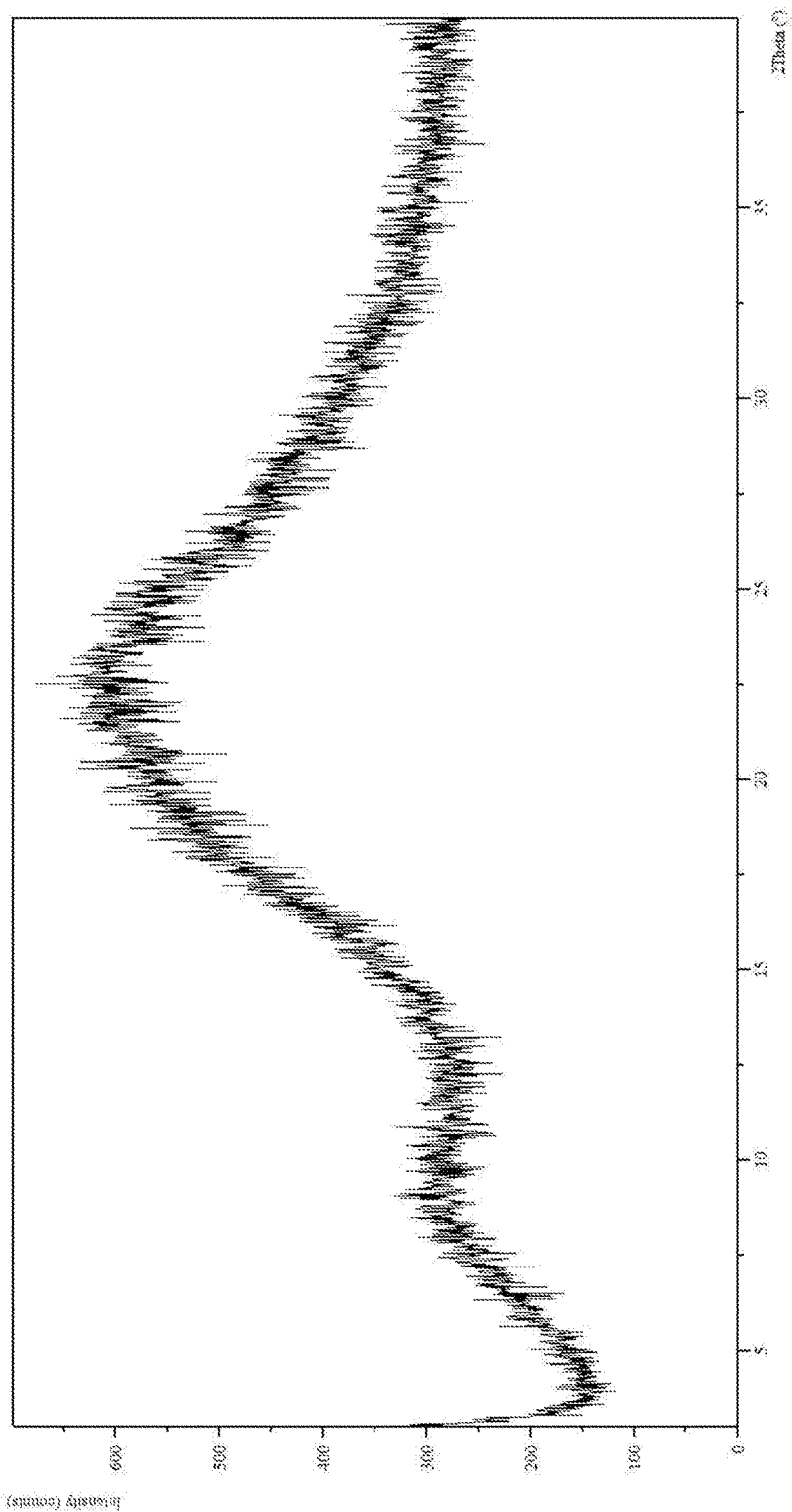
FIG. 11 provides an X-ray powder diffraction (XRPD) pattern of amorphous benzene sulfonate of the compound of formula (Ia).

2. Identification of Amorphous (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Benzene Sulfonate The XRPD pattern was analyzed and identified by using Empyrean X-ray powder diffraction (XRPD) with Cu-Kα radiation, experimental results are shown in FIG. 11.

Example 5: Preparation and Identification of Crystalline Form I(A) of the Complex of (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid and L-tartaric Acid

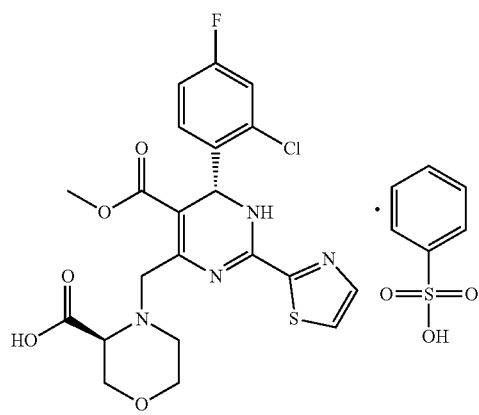

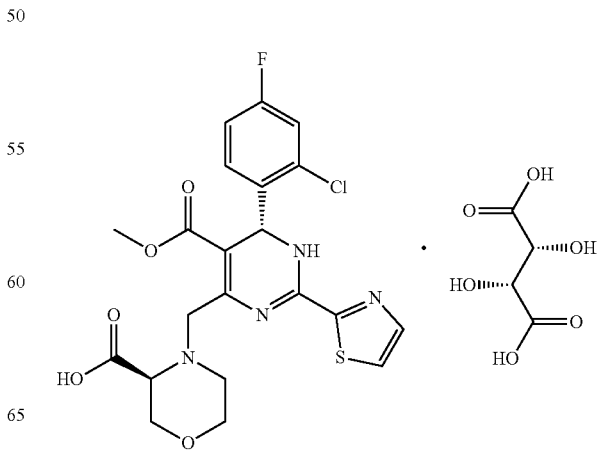

1. Preparation of Crystalline Form I(A) of the Complex of (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid and L-tartaric Acid Preparation Method 1 of L-tartaric Acid Complex Having Crystalline Form I(A):

To a 1 L of four-neck flask were added sequentially (S)-4-(((R)-6-(2-chloro-4-fluorophenyl)-5-(methoxycarbonyl)-2-(thiazol-2-yl)-3,6-dihydropyrimidin-4-yl)methyl)morpholine-3-carboxylic acid (48.5 g, 98 mmol) and anhydrous ethanol (340 mL). The mixture was stirred at room temperature until dissolved completely, then cooled to 50° C. To the mixture was added dropwise a prepared solution of L-tartrate (15.4 mL, 103 mmol) in anhydrous ethanol (146 mL). The addition time was controlled within about 30 minutes. After the addition, the mixture was further stirred for 30 minutes, whereupon the heating was turned off, then the mixture was cooled naturally to 25±5° C. and crystallized, and kept at the temperature and stirred continually for 12±4 hours. The mixture was filtered and the filter cake was washed with anhydrous ethanol (150 mL), the resulting product was dried in air for 30 minutes, then dried in vacuo at room temperature for 1-2 hours, thereafter dried in vacuo at 60° C. for 8-12 hours, the heating was stopped, the solid was cooled to room temperature naturally to give crystalline form I(A) of the complex of the compound named (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic acid and L-tartaric acid as a yellow crystalline solid (49.5 g, productivity: 78.3%).

Preparation Method 2 of L-tartaric Acid Complex Having Crystalline Form I(A):

To a dry flask were added sequentially L-tartaric acid (10 g, 66.6 mmol), water (50 mL), acetone (25 mL), after stirring to uniformity, the mixture was heated to 60° C. until the solid was dissolved completely, to the mixture was added (S)-4-(((R)-6-(2-chloro-4-fluorophenyl)-5-(methoxycarbonyl)-2-(thiazol-2-yl)-3,6-dihydropyrimidin-4-yl)methyl)morpholine-3-carboxylic acid (10 g, 20.23 mmol), kept at the temperature and stirred for 30 minutes, the heating was turned off, the mixture was cooled to 25±5° C., kept at the temperature and stirred for 8 hours. The mixture was filtered and washed with water (35 mL). The product was dried in vacuo at 70° C. for 16 hours to give crystalline form I(A) of the complex of the compound named (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic acid and L-tartaric acid as a yellow crystalline solid (9.57 g, productivity: 73.4%).

Preparation Method 3 of L-TARTARIC Acid Complex Having Crystalline Form I(A):

To a solution of (S)-4-(((R)-6-(2-chloro-4-fluorophenyl)-5-(methoxycarbonyl)-2-(thiazol-2-yl)-3,6-dihydropyrimidin-4-yl)methyl)morpholine-3-carboxylic acid (100 mg) in isopropanol (0.8 mL) was added dropwise a solution of L-tartaric acid (61 mg) in isopropanol (1.8 mL) at room temperature. After the addition, the resulting mixture was reacted at room temperature for 27 hours, then filtered. The filter cake was washed with isopropanol (5.0 mL×2) and dried in vacuo at 60° C. to give crystalline form I(A) of the complex of the compound named (S)-4-(((R)-6-(2-chloro-4-fluorophenyl)-5-(methoxycarbonyl)-2-(thiazol-2-yl)-1,6-dihydropyrimidine-4-yl)methyl)morpholine-3-carboxylic acid and L-tartaric acid as a yellow crystalline solid (78 mg, productivity: 59.9%). The compound was characterized by the following spectroscopic data: $^1$H NMR (400 MHz, DMSO-$d_6$) δ (ppm): 9.86 (s, 1H), 8.02 (d, J=3.1 Hz, 1H), 7.93 (d, J=3.1 Hz, 1H), 7.40 (dt, J=9.0, 4.6 Hz, 2H), 7.15 (td, J=8.5, 2.6 Hz, 1H), 6.04 (s, 1H), 4.31 (s, 2H), 4.24 (d, J=17.6 Hz, 1H), 4.10-3.91 (m, 2H), 3.83 (dd, J=11.1, 3.1 Hz, 1H), 3.74-3.64 (m, 2H), 3.61 (t, J=3.6 Hz, 1H), 3.51 (s, 3H), 3.08 (t, J=8.5 Hz, 1H), 2.40 (d, J=12.0 Hz, 1H).

2. Identification of Crystalline Form I(A) of the Complex of (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid and L-tartaric Acid (1) L-tartrate having crystalline form I(A) was analyzed and identified by using Empyrean X-ray powder diffraction (XRPD) with Cu-Kα radiation, the same X-ray powder diffraction (XRPD) patterns of L-tartaric acid complex having crystalline form I(A) obtained by the above three methods were as shown in FIG. 1, having the following characteristic diffraction peaks expressed in degrees 2θ at 7.30°, 7.310, 7.61°, 9.29 0, 11.600, 14.690, 15.330, 17.220, 17.820, 18.080, 18.42°, 19.510, 20.51°, 20.800, 21.61°, 22.560, 23.05°, 23.360, 23.54°, 23.790, 24.39°, 24.810, 25.78°, 26.070, 27.34°, 28.250, 28.87°, 29.720, 30.22°, 31.070, 31.55°, 32.250, 32.85°, 33.24°, 34.24°, 35.03°, 35.22°, 36.03°, 36.88°, 37.33°, 37.86° and 38.36°. The error margin in 2θ of the characteristic peaks is ±0.2°.

Figure 2:
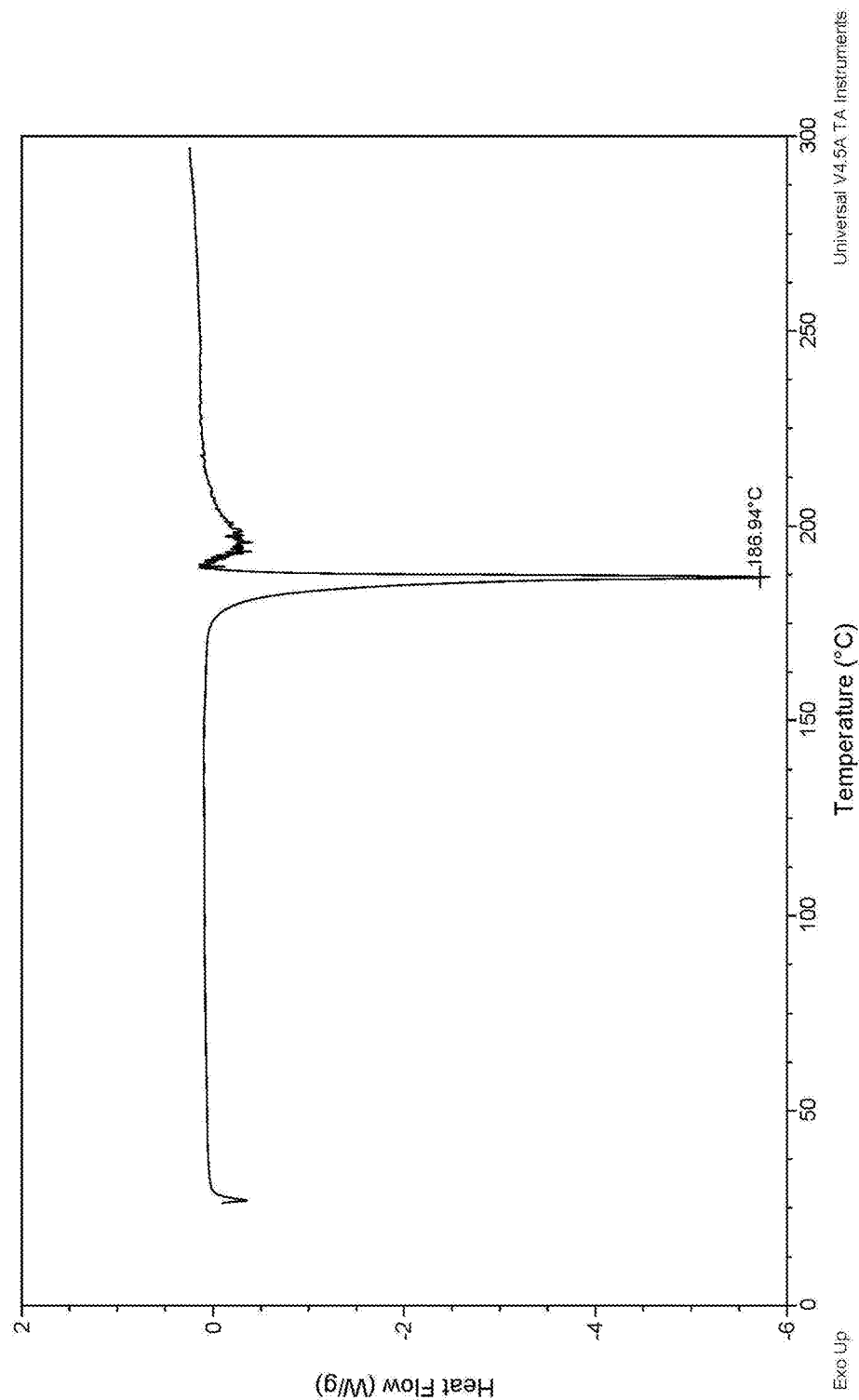
FIG. 2 provides a differential scanning calorimetry (DSC) thermogram of the complex having crystalline form I(A) of L-tartaric acid and the compound of formula (Ia) (obtained by preparation method 3).
Figure 3:
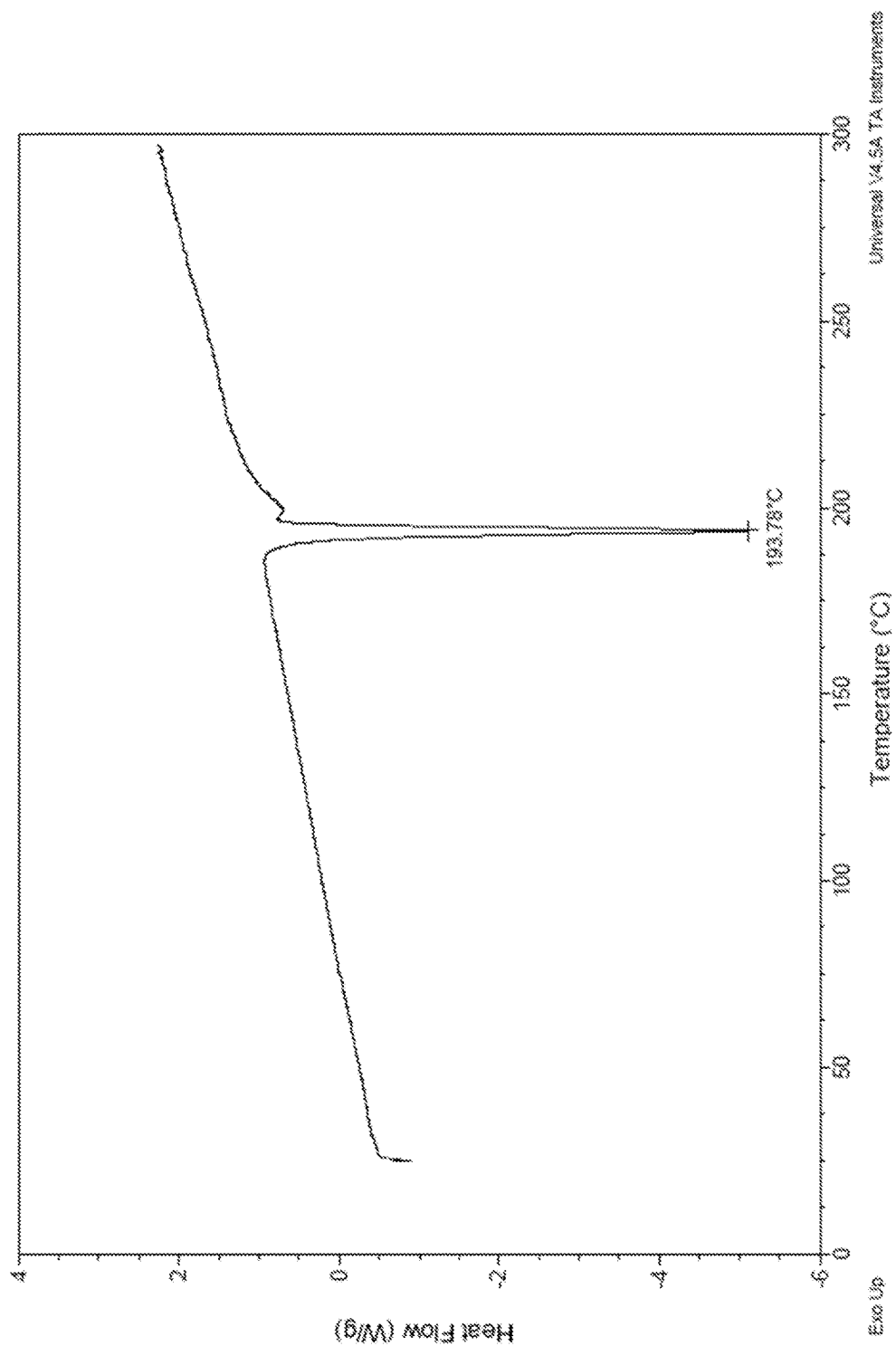
FIG. 3 provides a differential scanning calorimetry (DSC) thermogram of the complex having crystalline form I(A) of L-tartaric acid and the compound of formula (Ia)(obtained by preparation method 1 or 2).

(2) L-tartaric acid complex having crystalline form I(A) obtained by preparation method 3 was identified by using TA Q2000 differential scanning calorimetry (DSC) with a scan rate of 10° C./minute, experimental results are shown in FIG. 2, comprising an endothermic peak at 186.94° C. The error margin of the endothermic peaks is ±3° C.; L-tartaric acid complex having crystalline form I(A) obtained by preparation method 1 and preparation method 2 was identified by using TA Q2000 differential scanning calorimetry (DSC) with a scan rate of 10° C./minute, the same experimental results are shown in FIG. 3, comprising an endothermic peak at 193.78° C. The error margin of the endothermic peaks is ±3° C.

Figure 4:
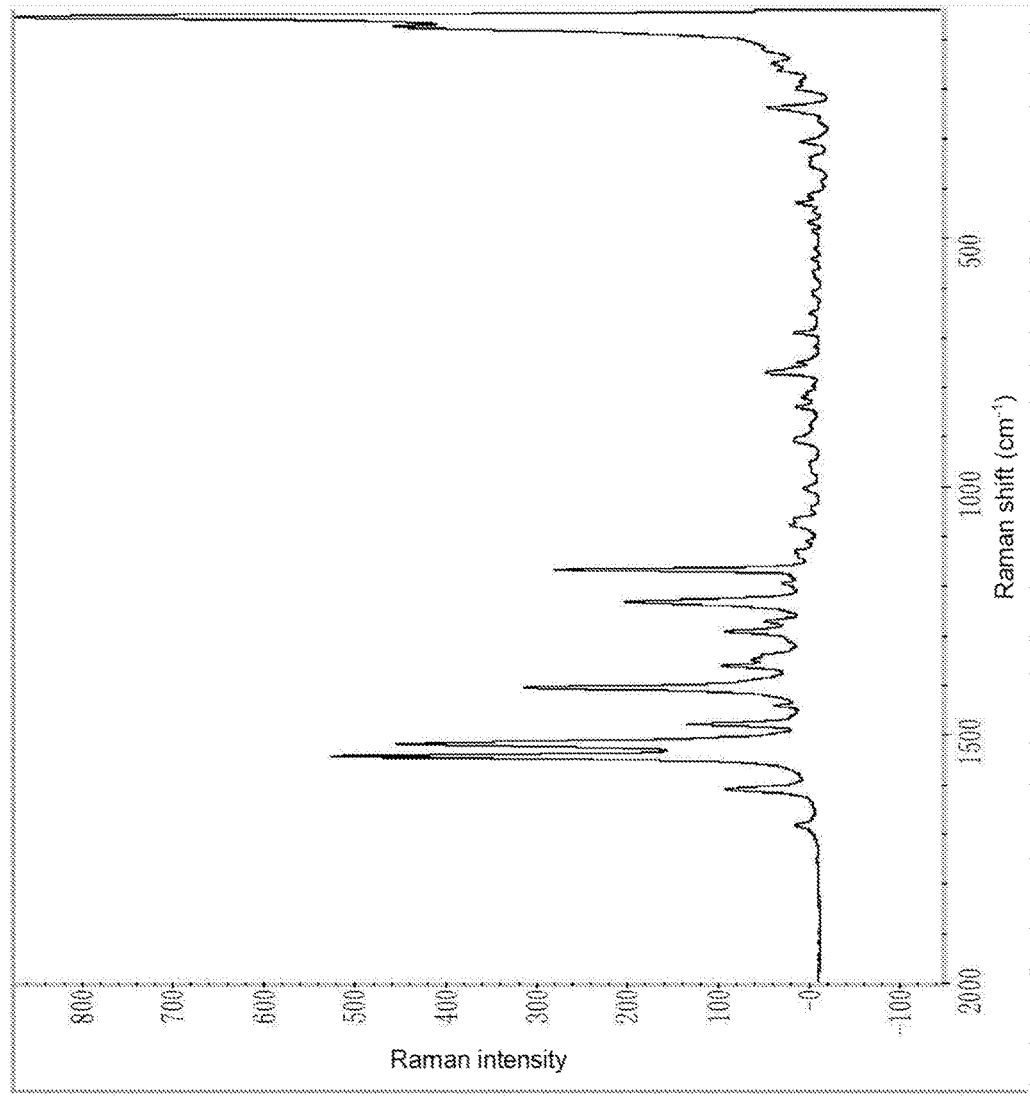
FIG. 4 provides a Raman spectrogram of the complex having crystalline form I(A) of L-tartaric acid and the compound of formula (Ia).

(3) L-tartrate having crystalline form I(A) was determinated by using Thermo DXR confocal laser Raman spectrometer, and the Raman spectrograms of L-tartaric acid complex having crystalline form I(A) obtained by the above three preparation methods were the same, the experimental results are shown in FIG. 4, having the following absorption peaks at 51, 71, 115, 144, 158, 180, 196, 234, 303, 427, 688, 746, 767, 818, 837, 905, 1001, 1062, 1075, 1128, 1137, 1165, 1179, 1193, 1230, 1269, 1289, 1324, 1337, 1346, 1357, 1401, 1438, 1453, 1477, 1517, 1541, 1607 and 1679 cm$^{-1}$, the error margin of the absorption peaks is ±2 cm$^{-1}$.

(4) Single Crystal X-Ray Study

L-tartaric acid complex having crystalline form I(A) was characterized by unit cell parameters approximately equal to those reported in Table 2 below. The unit cell parameters were measured at a temperature of about 150(2) K.

Figure 30:
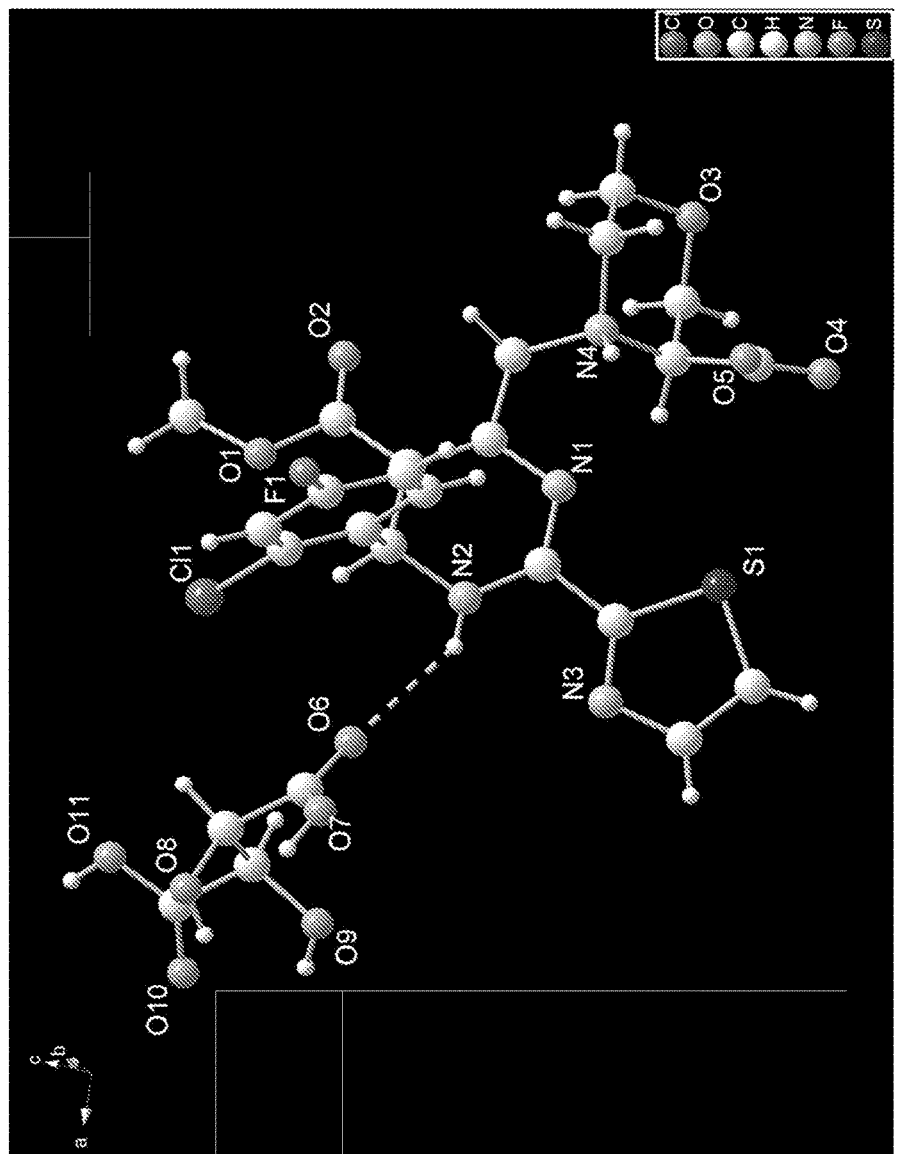
FIG. 30 provides an X-ray single crystal diffraction pattern of the crystalline form I(A) of the complex of compound (Ia) and L-startaric acid.

TABLE 2 a = 11.7649(3) Å
b = 9.75352(19) Å
c = 12.3294(2) Å
α = 90°
β = 102.581(2)°
γ = 90°
Space group: monoclinic, P2$_1$
Asymmetric unit number Z in the unit cell:: 2
Volume: 1380.83(5) Å$^3$ The crystal structure belongs to the monoclinic space group, P2$_1$, with two formula units in the unit cell. The structure contains (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic acid and L-tartaric acid, the molar ratio thereof is 1:1. The atomic coordinates parameters (×10$^4$) of crystalline form I(A) of L-tartaric acid complex are shown in Table 3 below. After analytic structure, crystalline form I(A) of the complex formed from compound (Ia) and L-tartaric acid was proved as shown in FIG. 30.

TABLE 3

Atomic coordinates parameters (×10$^4$) for crystalline form I(A) of the complex formed from compound (Ia) and L-tartaric acid

| Non-hydrogen atomic coordinates parameters (×10$^4$) | | | | Hydrogen atomic coordinates parameters (×10$^4$) | | | |
|---|---|---|---|---|---|---|---|
| Atom | X | Y | Z | Atom | X | Y | Z |
| C (1) | 8375 (3) | 8130 (3) | 1730 (2) | H (2) | 9396 | 9319 | 4159 |
| C (2) | 8840 (3) | 9487 (3) | 3433 (2) | H (6) | 9032 | 5916 | −1526 |
| C (3) | 7629 (3) | 9053 (3) | 3533 (3) | H (7) | 10804 | 6326 | −159 |
| C (4) | 6895 (3) | 8505 (3) | 2630 (2) | H (9) | 7738 | 10812 | 1638 |
| C (5) | 8805 (3) | 7500 (4) | 823 (3) | H (10) | 7740 | 13102 | 1105 |
| C (6) | 9065 (3) | 6356 (5) | −832 (3) | H (12) | 9995 | 14005 | 3998 |
| C (7) | 10060 (3) | 6599 (5) | −57 (3) | H (15A) | 7152 | 10593 | 6405 |
| C (8) | 8889 (3) | 10992 (3) | 3133 (3) | H (15B) | 8520 | 10512 | 6933 |
| C (9) | 8205 (3) | 11453 (4) | 2119 (3) | H (15C) | 7755 | 9140 | 6750 |
| C (10) | 8192 (3) | 12811 (4) | 1802 (3) | H (16A) | 5305 | 9001 | 2967 |
| C (11) | 8847 (3) | 13731 (4) | 2517 (3) | H (16B) | 5542 | 7382 | 2994 |
| C (12) | 9542 (3) | 13349 (4) | 3520 (3) | H (17A) | 3788 | 9597 | 1676 |
| C (13) | 9558 (3) | 11974 (4) | 3809 (2) | H (17B) | 3439 | 8930 | 461 |
| C (14) | 7261 (3) | 9271 (3) | 4579 (3) | H (18A) | 3208 | 7601 | 2467 |
| C (15) | 7861 (3) | 10049 (5) | 6447 (3) | H (18B) | 2145 | 8163 | 1529 |
| C (16) | 5626 (3) | 8242 (4) | 2592 (2) | H (19A) | 3941 | 4916 | 988 |
| C (17) | 3747 (3) | 8725 (3) | 1258 (3) | H (19B) | 4237 | 5701 | 2156 |
| C (18) | 2934 (3) | 7755 (4) | 1659 (3) | H (20) | 5683 | 6248 | 1223 |
| C (19) | 3994 (3) | 5832 (4) | 1342 (3) | H (2A) | 9900 (30) | 8580 (40) | 2550 (30) |
| C (20) | 4905 (3) | 6686 (3) | 942 (2) | H (4) | 5330 (30) | 8720 (40) | 960 (30) |
| C (21) | 4692 (3) | 6770 (3) | −338 (2) | H (23) | 2883 | 9914 | 5717 |
| Cl (1) | 10456 (1) | 11531 (1) | 5080 (1) | H (24) | 2757 | 7566 | 5354 |
| F (1) | 8814 (2) | 15074 (2) | 2244 (2) | H (7A) | 3490 (40) | 10990 (50) | 3620 (40) |
| N (1) | 7242 (2) | 8127 (3) | 1668 (2) | H (8) | 4870 (40) | 9810 (50) | 5120 (50) |
| N (2) | 9167 (2) | 8617 (3) | 2580 (2) | H (9A) | 4640 (40) | 7080 (50) | 4820 (30) |
| N (3) | 9915 (2) | 7266 (3) | 882 (2) | H (11) | 4370 (50) | 8250 (70) | 7960 (30) |
| N (4) | 4952 (2) | 8128 (3) | 1408 (2) | | | | |
| O (1) | 8092 (2) | 9903 (2) | 5341 (2) | | | | |
| O (2) | 6338 (2) | 8919 (3) | 4781 (2) | | | | |
| O (3) | 2884 (2) | 6473 (3) | 1084 (2) | | | | |
| O (4) | 4441 (2) | 5699 (2) | −865 (2) | | | | |
| O (5) | 4800 (2) | 7961 (3) | −720 (2) | | | | |
| S (1) | 7884 (1) | 6957 (1) | −380 (1) | | | | |
| C (22) | 2517 (3) | 9718 (4) | 4001 (3) | | | | |
| C (23) | 3305 (3) | 9545 (4) | 5158 (3) | | | | |
| C (24) | 3522 (3) | 8030 (4) | 5386 (2) | | | | |
| C (25) | 4308 (3) | 7774 (4) | 6535 (3) | | | | |
| O (6) | 1613 (2) | 9094 (3) | 3717 (2) | | | | |
| O (7) | 2854 (2) | 10602 (3) | 3316 (2) | | | | |
| O (8) | 4366 (2) | 10280 (3) | 5265 (2) | | | | |
| O (9) | 4028 (2) | 7482 (3) | 4538 (2) | | | | |
| O (10) | 5125 (2) | 6989 (3) | 6644 (2) | | | | |
| O (11) | 3983 (2) | 8455 (3) | 7311 (2) | | | | |

Example 6: Preparation and Identification of Amorphous (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Sulfate

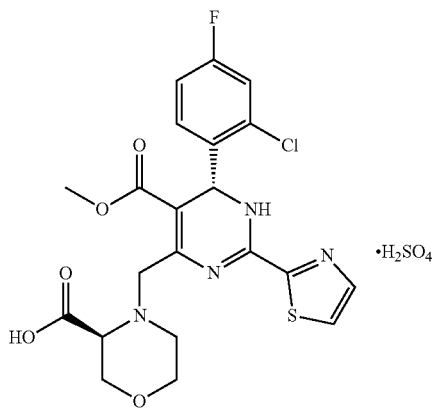

1. Preparation of Amorphous (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Sulfate To a solution of (S)-4-(((R)-6-(2-chloro-4-fluorophenyl)-5-(methoxycarbonyl)-2-(thiazol-2-yl)-3,6-dihydropyrimidine-4-yl)methyl)morpholine-3-carboxylic acid (101 mg) in ethanol (1.0 mL) was added a mixed solution of sulfuric acid (24.7 mg, Mw=98%) and ethanol (0.5 mL) dropwise at room temperature. After the addition, the resulting mixture was warmed and reacted for 12 hours, then dried over anhydrous sodium sulfate and filtered. The filtrate was concentrated to give the compound named (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic acid sulfate as a yellow solid (87 mg, productivity: 71.9%). The compound was characterized by the following spectroscopic data: $^1$H NMR (400 MHz, DMSO-$d_6$) δ (ppm): 12.52 (br, 1H), 9.86 (s, 1H), 8.03 (d, 1H), 7.94 (d, 1H), 7.43-7.38 (m, 2H), 7.16 (td, 1H), 6.04 (s, 1H), 4.24 (d, 1H), 4.06-3.97 (m, 2H), 3.84 (dd, 1H), 3.73-3.66 (m, 2H), 3.64-3.59 (m, 1H), 3.51 (s, 3H), 3.10-3.06 (m, 1H), 2.43-2.39 (m, 1H).

Figure 17:
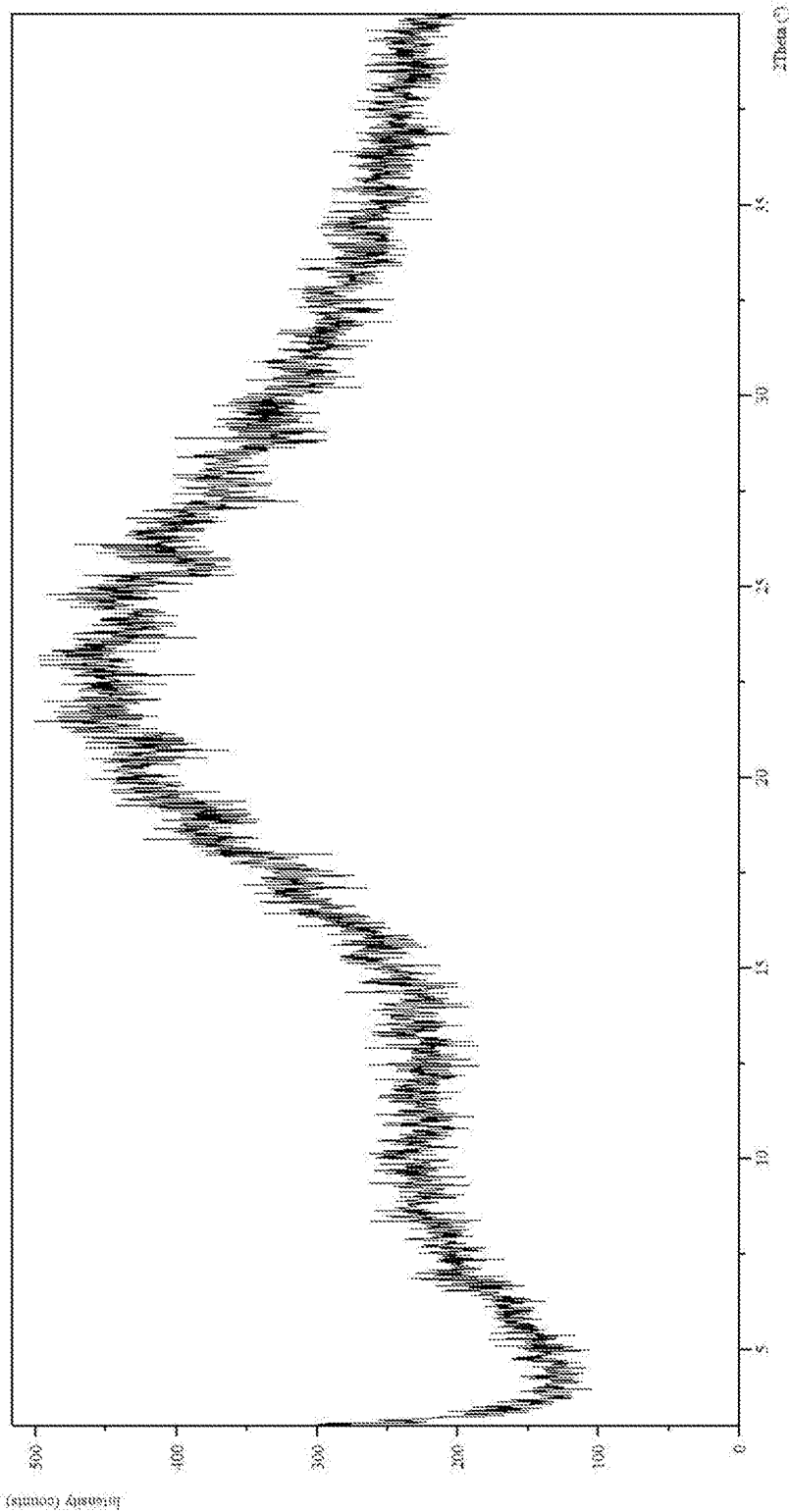
FIG. 17 provides an X-ray powder diffraction (XRPD) pattern of amorphous sulfate of the compound of formula (Ia).

2. Identification of Amorphous (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Sulfate The XRPD pattern was analyzed and identified by using Empyrean X-ray powder diffraction (XRPD) with Cu-Kα radiation, experimental results are shown in FIG. 17.

Example 7: Preparation and Identification of Amorphous (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Hydrobromide

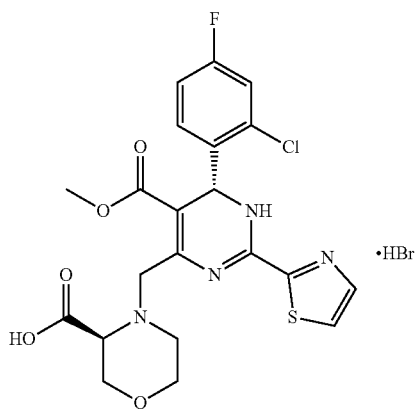 [SMILES: COC(=O)C1=C(CN2CCOC[C@H]2C(=O)O)N=C(c2nccs2)N[C@H]1c1ccc(F)cc1Cl ; Br]

1. Preparation of Amorphous (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Hydrobromide To a solution of (S)-4-(((R)-6-(2-chloro-4-fluorophenyl)-5-(methoxycarbonyl)-2-(thiazol-2-yl)-3,6-dihydropyrimidin-4-yl)methyl)morpholine-3-carboxylic acid (106 mg) in isopropanol (1.0 mL) was added dropwise a mixed solution of hydrobromic acid (40.0 mg, Mw=48%) and isopropanol (1.0 mL) at room temperature. After the addition, the resulting mixture was warmed and reacted for 12 hours, then dried over anhydrous sodium sulfate and filtered. The filtrate was concentrated to give the compound named (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic acid hydrobromide as a yellow solid (85 mg, productivity: 68.9%). The compound was characterized by the following spectroscopic data: $^1$H NMR (400 MHz, DMSO-$d_6$) δ (ppm): 12.52 (br, 1H), 9.86 (s, 1H), 8.03 (d, 1H), 7.94 (d, 1H), 7.43-7.38 (m, 2H), 7.16 (td, 1H), 6.04 (s, 1H), 4.24 (d, 1H), 4.06-3.97 (m, 2H), 3.84 (dd, 1H), 3.73-3.66 (m, 2H), 3.64-3.59 (m, 1H), 3.51 (s, 3H), 3.10-3.06 (m, 1H), 2.43-2.39 (m, 1H).

Figure 16:
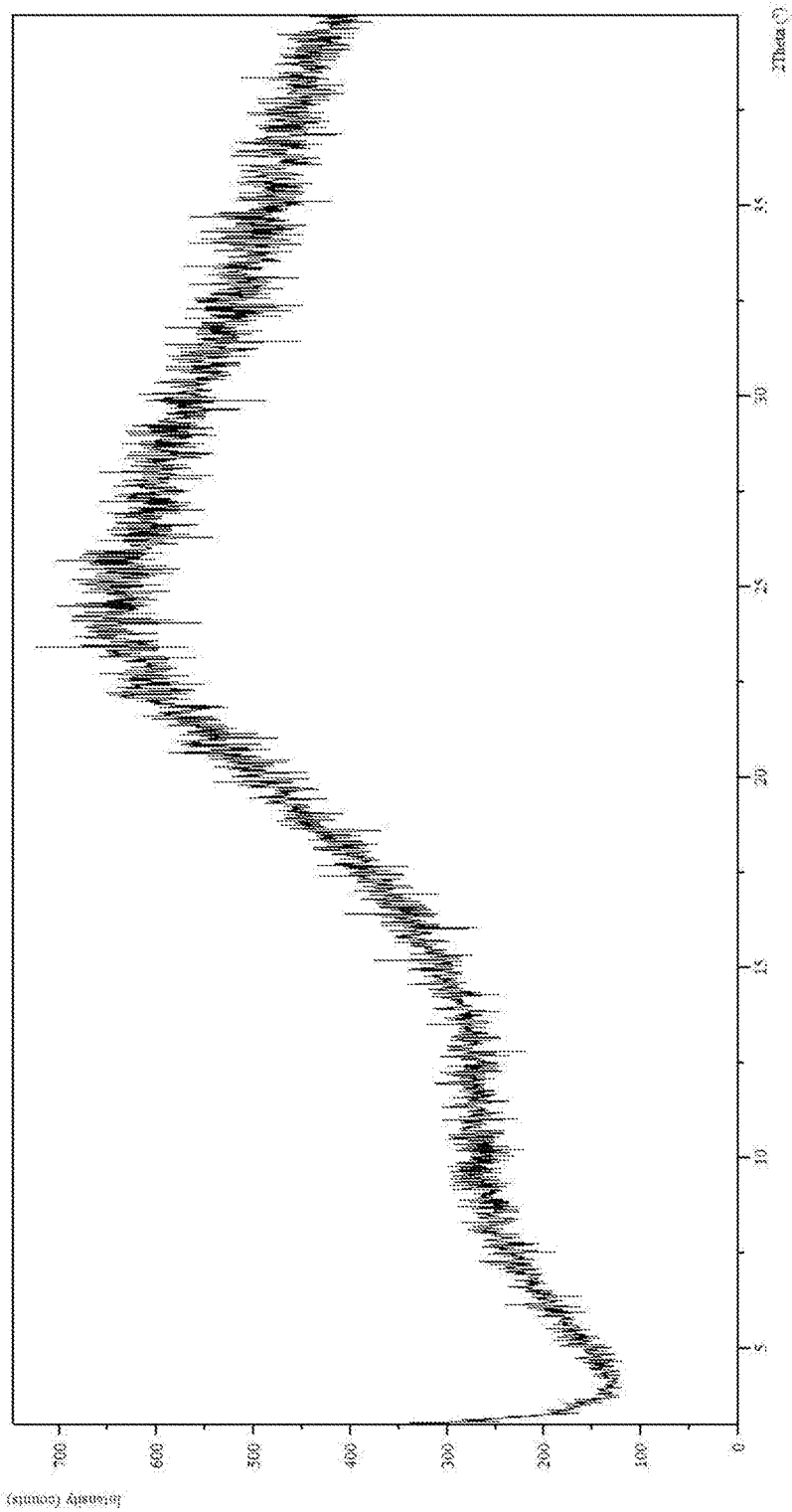
FIG. 16 provides an X-ray powder diffraction (XRPD) pattern of amorphous hydrobromide of the compound of formula (Ia).

2. Identification of Amorphous (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Hydrobromide The XRPD pattern was analyzed and identified by using Empyrean X-ray powder diffraction (XRPD) with Cu-Kα radiation, experimental results are shown in FIG. 16.

Example 8: Preparation and Identification of Crystalline Form I(C) (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Hydrobromide

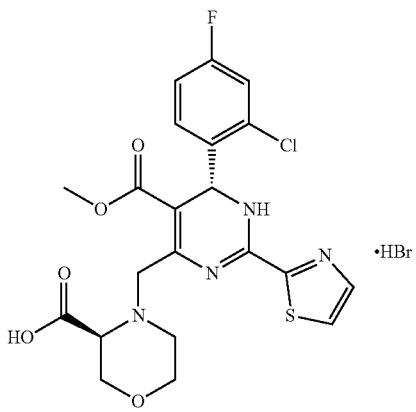

1. Preparation of Crystalline Form I(C) of (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Hydrobromide To a 100 mL of three-neck flask was added sequentially water (80 mL) and acetone (16 mL), then aqueous hydrobromic acid was added with stirring, heated to 60° C., a solution of (S)-4-(((R)-6-(2-chloro-4-fluorophenyl)-5-(methoxycarbonyl)-2-(thiazol-2-yl)-3,6-dihydropyrimidin-4-yl)methyl)morpholine-3-carboxylic acid (10 g, 20.21 mmol) was added in portions, after the solid was dissolved completely, the mixture was kept at the temperature and stirred for 30 minutes, the heating was turned off, then the mixture was cooled to 25-35° C., kept at the temperature and stirred for 12 hours, filtered, the filtrate was washed with water (50 mL), dried in vacuo at 25-35° C. for 1 hours, then dried in vacuo at 70° C. for 12 hours to give the compound named (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic acid hydrobromide having crystalline form I(C) as a yellow solid (7.7 g, productivity: 66.2%).

Figure 8:
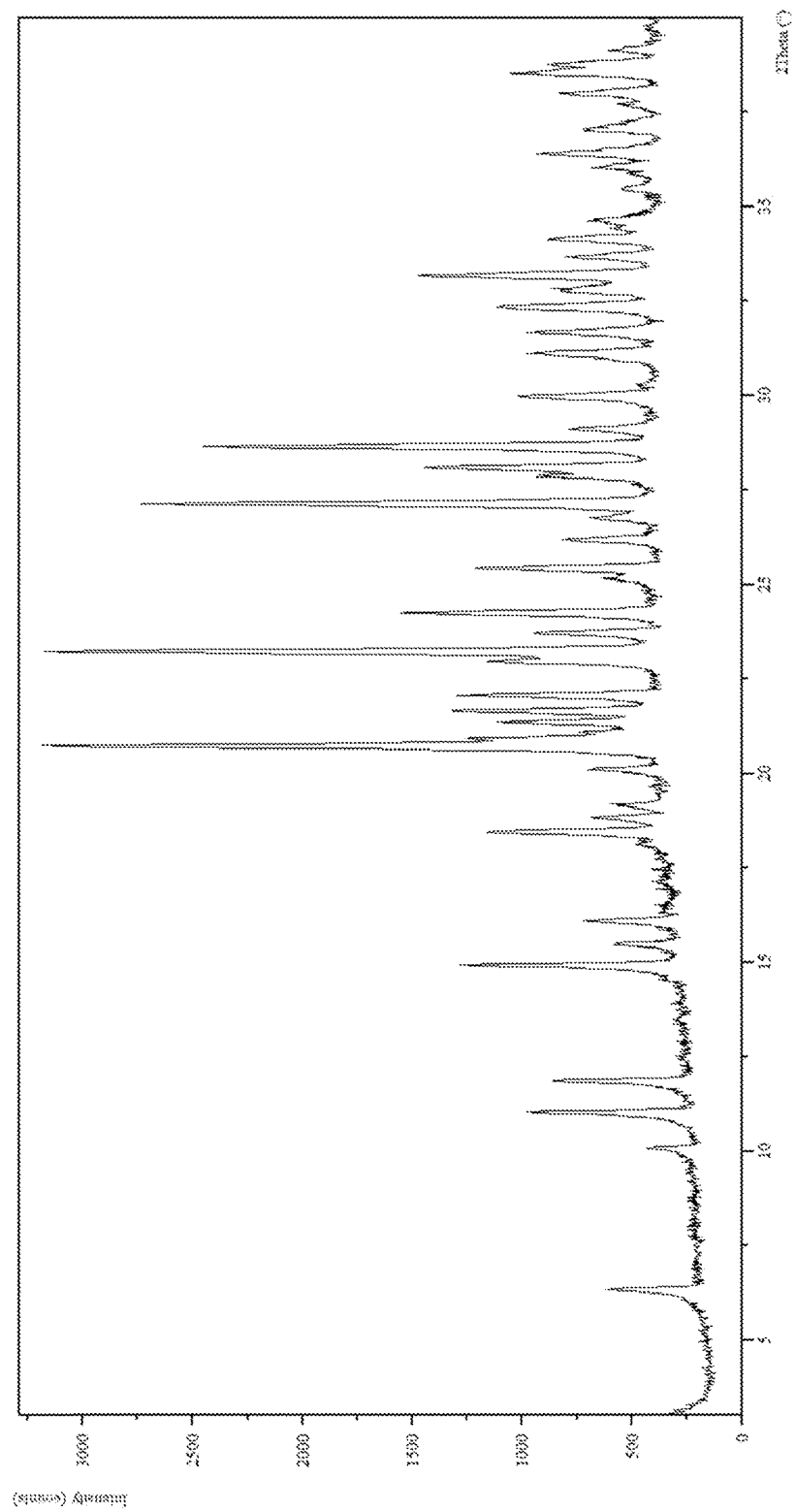
FIG. 8 provides an X-ray powder diffraction (XRPD) pattern of hydrobromide having crystalline form I(C) of the compound of formula (Ia).

2. Identification of Crystalline Form I(C) of (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Hydrobromide (1) The XRPD pattern of crystalline form I(C) was analyzed and identified by using Empyrean X-ray powder diffraction (XRPD) with Cu-Kα radiation, experimental results are shown in FIG. 8, having the following characteristic peaks expressed in degrees 2θ at 6.290, 10.04°, 10.990, 11.83°, 14.870, 15.44°, 16.050, 18.41°, 18.790, 19.12°, 20.060, 20.69°, 21.300, 21.61°, 22.020, 22.93°, 23.180, 23.67°, 24.200, 25.38°, 26.140, 26.73°, 27.090, 27.83°, 28.050, 28.59°, 29.060, 29.92°, 31.050, 31.63°, 32.290, 32.76°, 33.130, 33.63°, 34.100, 34.55°, 35.420, 35.99° 36.36°, 37.02°, 37.93°, 38.49°, 38.72° and 39.10°. The error margin in 2θ of the characteristic peaks is ±0.2°.

Figure 9:
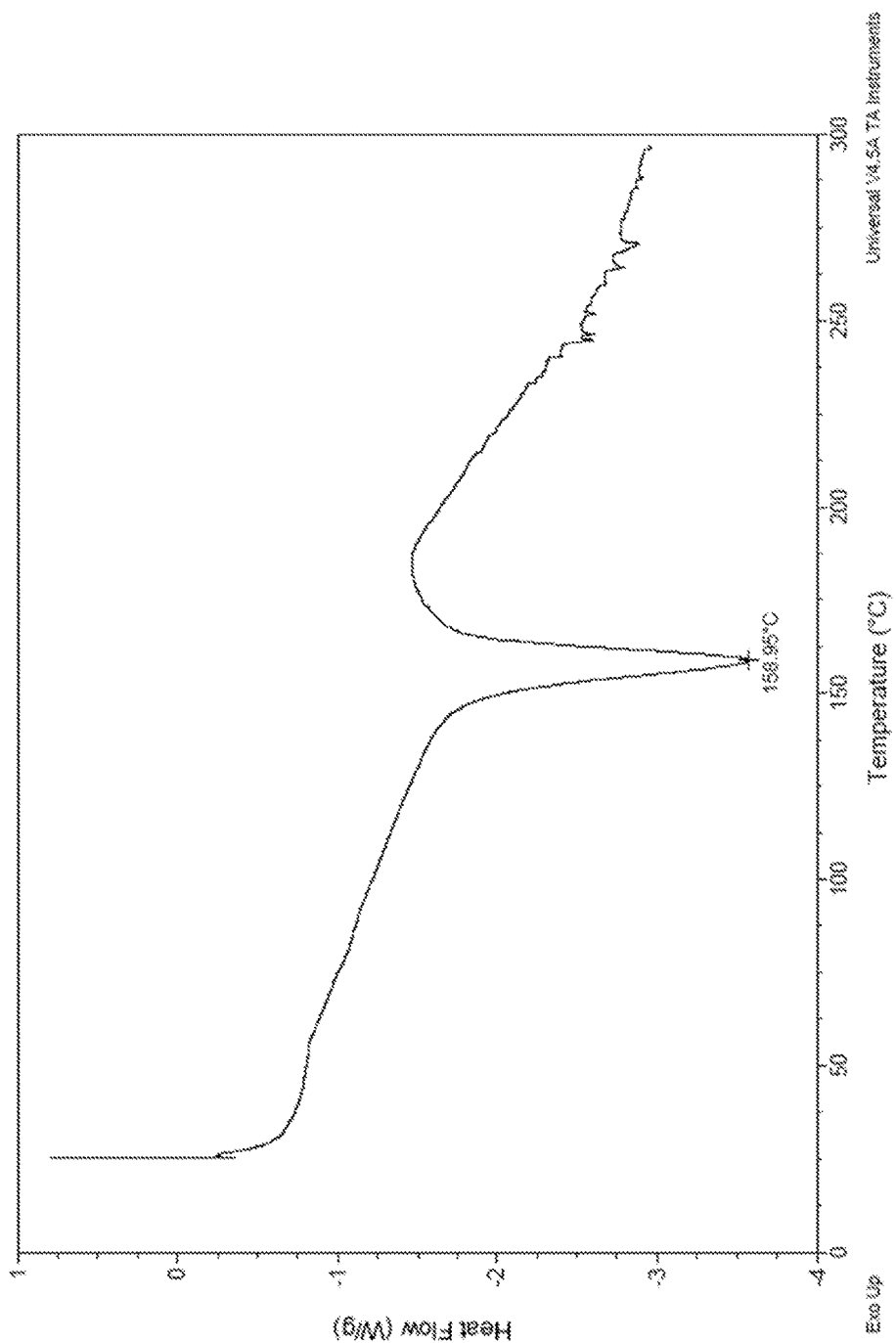
FIG. 9 provides a differential scanning calorimetry (DSC) thermogram of hydrobromide having crystalline form I(C) of the compound of formula (Ia).

(2) The DSC thermogram of crystalline form I(C) was analyzed and identified by using TA Q2000 differential scanning calorimetry (DSC) with a scan rate of 10° C./minute, experimental results are shown in FIG. 9, comprising an endothermic peak at 158.95° C. The error margin of the endothermic peaks is ±3° C.

Example 9: Preparation and Identification of Amorphous (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Oxalate

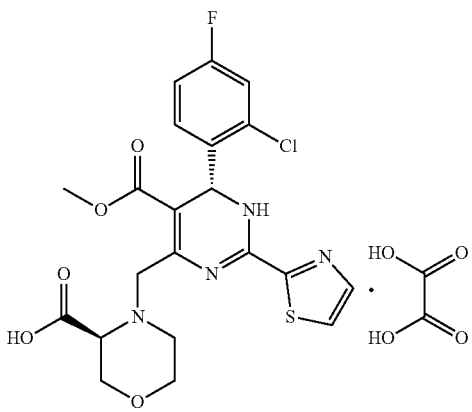

1. Preparation of Amorphous (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Oxalate To a solution of (S)-4-(((R)-6-(2-chloro-4-fluorophenyl)-5-(methoxycarbonyl)-2-(thiazol-2-yl)-3,6-dihydropyrimidin-4-yl)methyl)morpholine-3-carboxylic acid (104 mg) in ethyl acetate (0.5 mL) was added a solution of oxalate dihydrate (27 mg) in ethyl acetate (1.0 mL) dropwise at room temperature. After the addition, the resulting mixture was reacted at room temperature for 11 hours, then n-heptane (15 mL) was added dropwise. The mixture was stirred and crystals precipitated out. The resulting mixture was filtered by suction. The filter cake was washed with n-heptane (5.0 mL×2) and dried in vacuo at 25° C. to give the compound named (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic acid oxalate as a yellow solid (90 mg, productivity: 73.2%). The compound was characterized by the following spectroscopic data: $^1$H NMR (400 MHz, DMSO-$d_6$) δ (ppm): 12.52 (br, 1H), 9.86 (s, 1H), 8.03 (d, 1H), 7.94 (d, 1H), 7.43-7.38 (m, 2H), 7.16 (td, 1H), 6.04 (s, 1H), 4.24 (d, 1H), 4.06-3.97 (m, 2H), 3.84 (dd, 1H), 3.73-3.66 (m, 2H), 3.64-3.59 (m, 1H), 3.51 (s, 3H), 3.10-3.06 (m, 1H), 2.43-2.39 (m, 1H).

Figure 13:
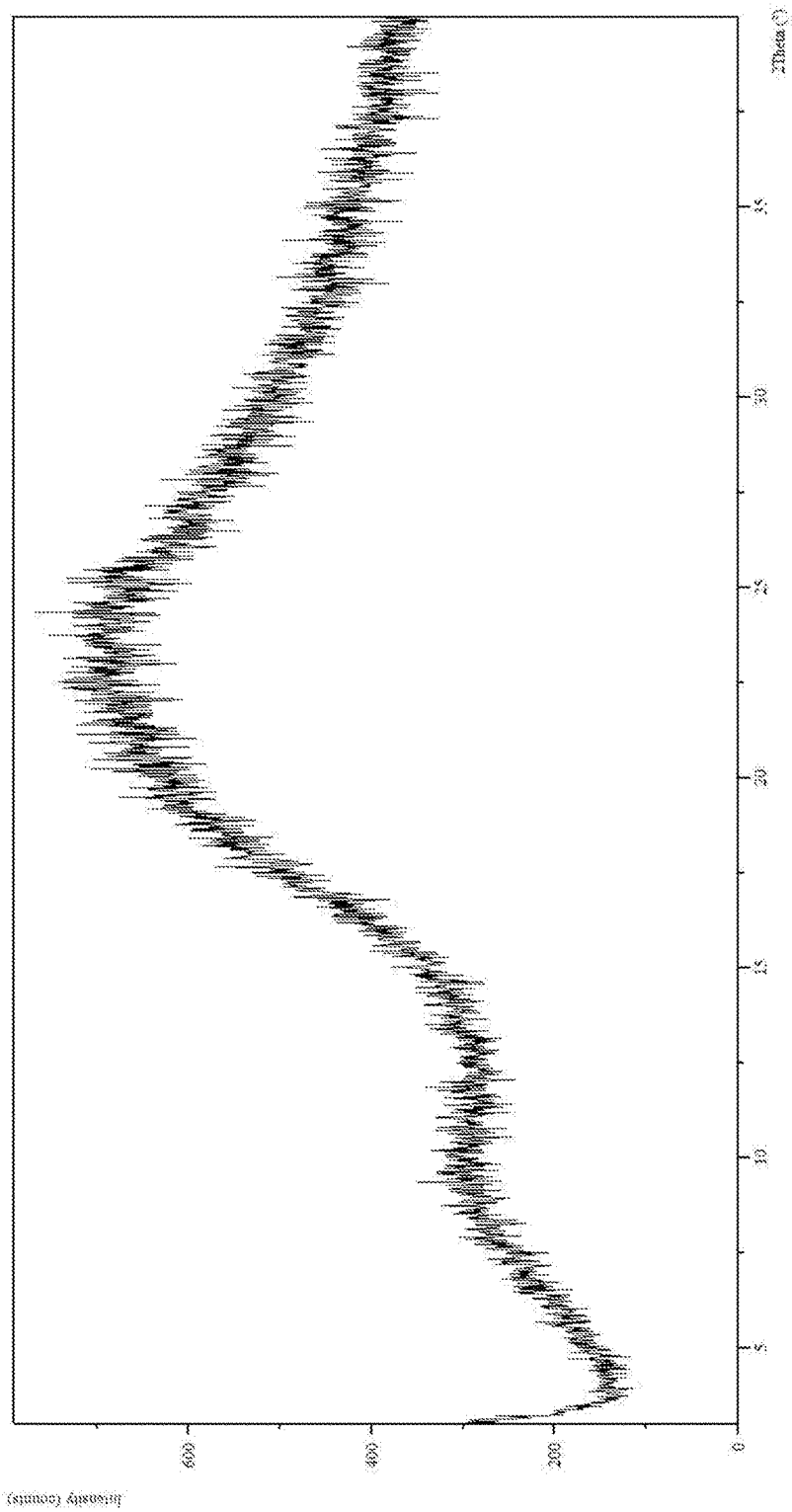
FIG. 13 provides an X-ray powder diffraction (XRPD) pattern of amorphous oxalate of the compound of formula (Ia).

2. Identification of Amorphous (S)-4-(((R)-6-(2-chloro-4-fluorophenyl)-5-(methoxycarbonyl)-2-(thiazol-22-yl)-1,6-dihydropyrimidin-4-yl)methyl)morpholine-3-carboxylic Acid Oxalate The XRPD pattern was analyzed and identified by using Empyrean X-ray powder diffraction (XRPD) with Cu-Kα radiation, experimental results are shown in FIG. 13.

Example 10: Preparation and Identification of Amorphous (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Maleate

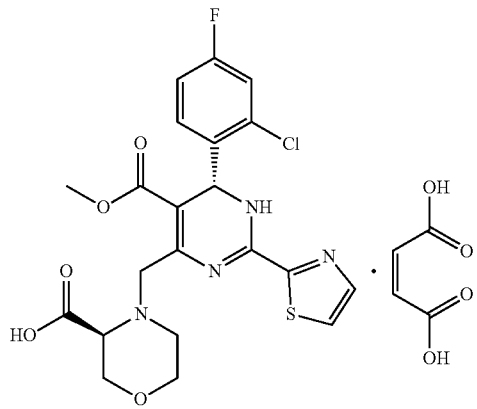

1. Preparation of Amorphous (S)-4-(((R)-6-(2-chloro-4-fluorophenyl)-5-(methoxycarbonyl)-2-(thiazol-22-yl)-1,6-dihydropyrimidin-4-yl)methyl)morpholine-3-carboxylic Acid Maleate To a solution of (S)-4-(((R)-6-(2-chloro-4-fluorophenyl)-5-(methoxycarbonyl)-2-(thiazol-2-yl)-3,6-dihydropyrimidin-4-yl)methyl)morpholine-3-carboxylic acid (103 mg) in isopropanol (1.0 mL) was added a solution of maleic acid (28 mg) in isopropanol (1.0 mL) dropwise at room temperature. After the addition, the resulting mixture was stirred at room temperature for 19 hours, then n-heptane (15 mL) was added dropwise. The mixture was stirred and crystals precipitated out. The resulting mixture was filtered by suction. The filter cake was washed with n-heptane (5.0 mL×2) and dried in vacuo at ° C. to give the compound named (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic acid maleate as a yellow solid (67 mg, productivity: 52.8%). The compound was characterized by the following spectroscopic data: $^1$H NMR (400 MHz, DMSO-$d_6$) δ (ppm): 9.87 (s, 1H), 8.03 (d, J=3.1 Hz, 1H), 7.94 (d, J=3.1 Hz, 1H), 7.41 (dt, J=10.3, 5.4 Hz, 2H), 7.16 (td, J=8.5, 2.6 Hz, 1H), 6.22 (s, 2H), 6.04 (s, 1H), 4.25 (d, J=17.6 Hz, 1H), 4.09-3.93 (m, 2H), 3.84 (dd, J=11.2, 3.2 Hz, 1H), 3.69 (dd, J=10.5, 7.0 Hz, 3H), 3.51 (s, 3H), 3.15-3.03 (m, 1H), 2.57 (s, 1H), 2.43 (d, J=11.9 Hz, 1H).

Figure 15:
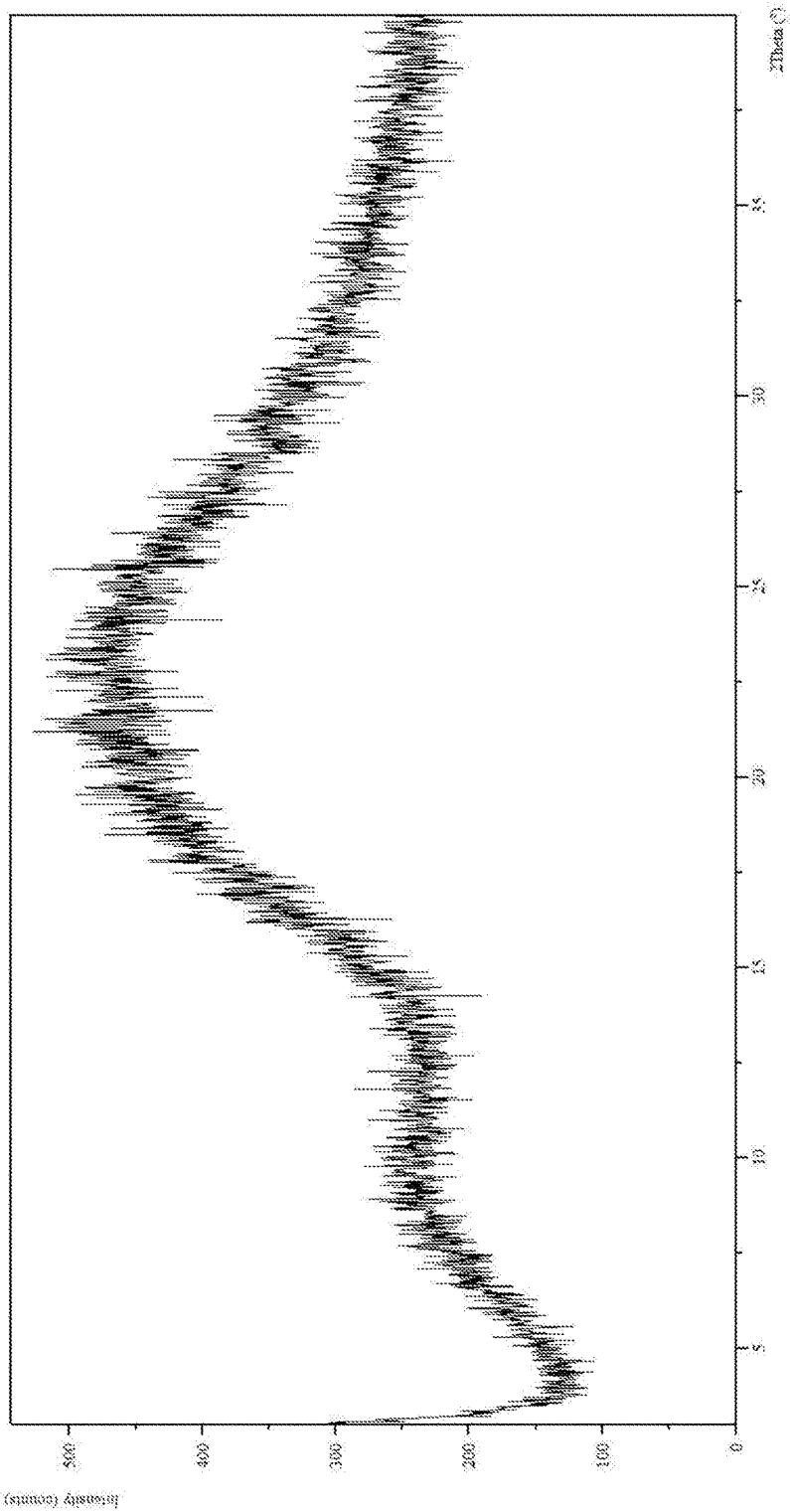
FIG. 15 provides an X-ray powder diffraction (XRPD) pattern of amorphous maleate of the compound of formula (Ia).

2. Preparation of Amorphous (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Maleate The XRPD pattern was analyzed and identified by using Empyrean X-ray powder diffraction (XRPD) with Cu-Kα radiation, experimental results are shown in FIG. 15.

Example 11: Preparation and Identification of Amorphous (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Citrate

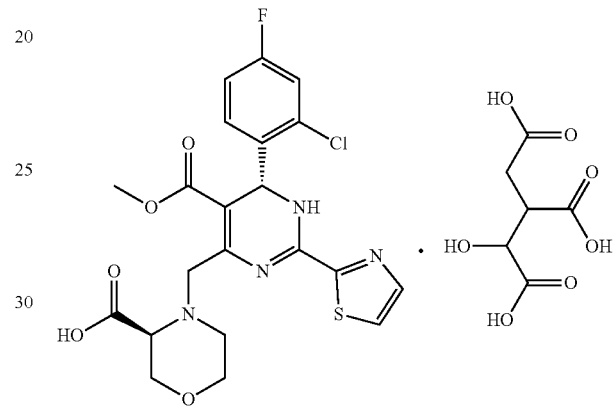

1. Preparation of Amorphous (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Citrate To a solution of (S)-4-(((R)-6-(2-chloro-4-fluorophenyl)-5-(methoxycarbonyl)-2-(thiazol-2-yl)-3,6-dihydropyrimidin-4-yl)methyl)morpholine-3-carboxylic acid (103 mg) in ethyl acetate (1.0 mL) was added a solution of citric acid monohydrate (51 mg) in ethyl acetate (1.0 mL) dropwise at room temperature. After the addition, the resulting mixture was stirred at room temperature for 22.5 hours, then n-heptane (15 mL) was added dropwise. The mixture was stirred and crystals precipitated out. The resulting mixture was filtered by suction. The filter cake was washed with n-heptane (5.0 mL×2) and dried in vacuo at 25° C. to give the compound named (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic acid citrate as a yellow solid (127 mg, productivity: 88.8%). The compound was characterized by the following spectroscopic data: $^1$H NMR (400 MHz, DMSO-$d_6$) δ (ppm): 9.86 (s, 1H), 8.02 (d, J=3.1 Hz, 1H), 7.94 (t, J=4.0 Hz, 1H), 7.40 (dt, J=8.7, 6.4 Hz, 2H), 7.15 (td, J=8.5, 2.5 Hz, 1H), 6.04 (s, 1H), 4.23 (d, J=17.5 Hz, 1H), 4.10-3.92 (m, 2H), 3.83 (dd, J=11.1, 3.1 Hz, 1H), 3.70 (dd, J=12.2, 7.9 Hz, 2H), 3.61 (d, J=3.5 Hz, 1H), 3.51 (s, 3H), 3.14-3.02 (m, 1H), 2.75 (d, J=15.6 Hz, 2H), 2.65 (d, J=15.4 Hz, 2H), 2.56 (s, 1H), 2.40 (d, J=11.9 Hz, 1H).

Figure 14:
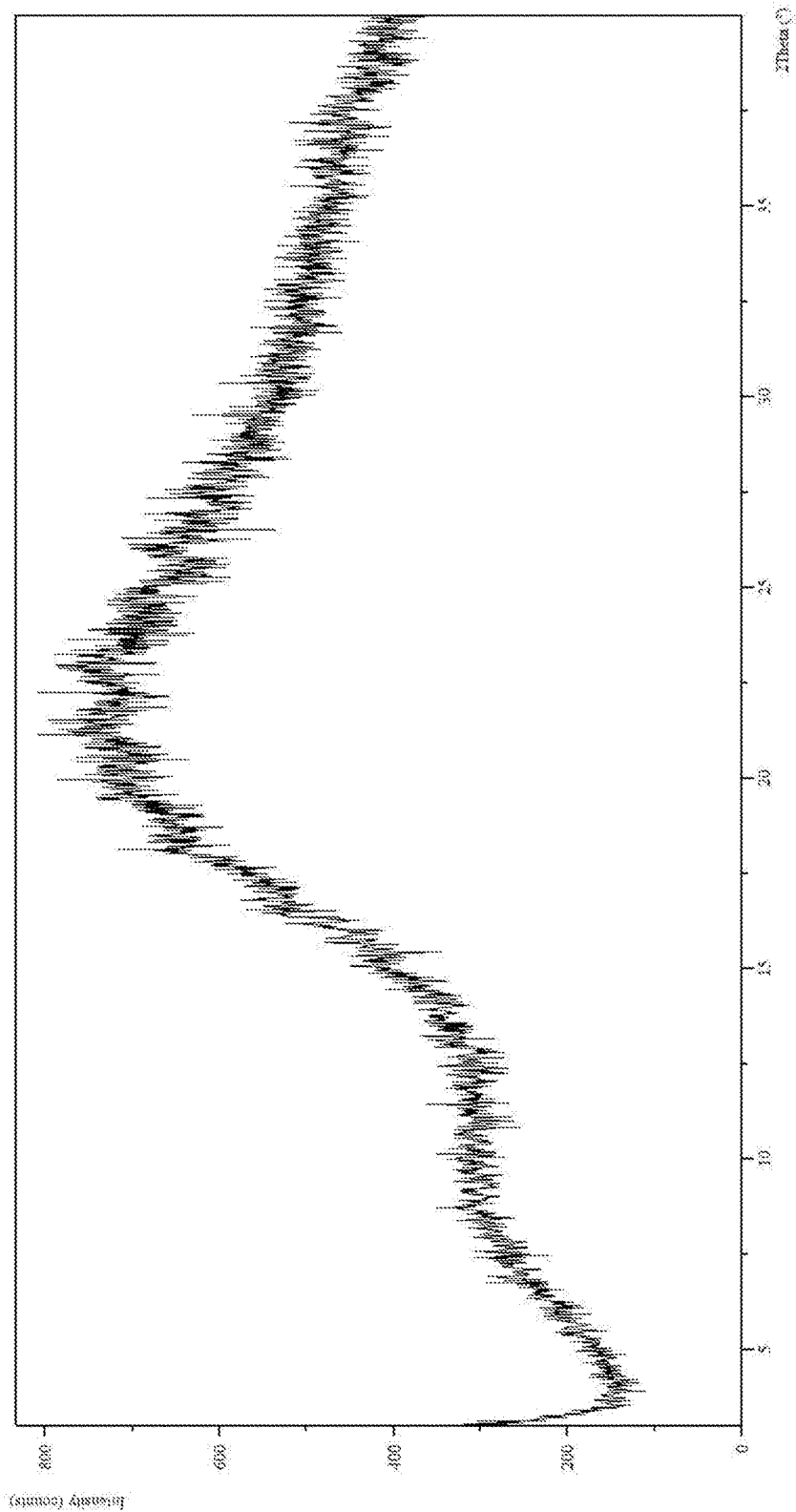
FIG. 14 provides an X-ray powder diffraction (XRPD) pattern of amorphous citrate of the compound of formula (Ia).

2. Identification of Amorphous (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Citrate The XRPD pattern was analyzed and identified by using Empyrean X-ray powder diffraction (XRPD) with Cu-Kα radiation, experimental results are shown in FIG. 14.

Example 12: Preparation and Identification of Amorphous (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Hydrochloride

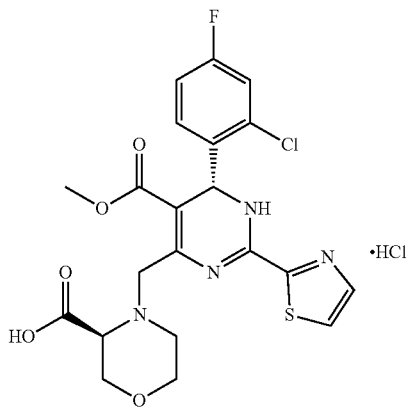 [SMILES: COC(=O)C1=C(CN2CCOC[C@H]2C(=O)O)N=C(c2nccs2)N[C@H]1c1ccc(F)cc1Cl ; Cl]

1. Preparation of Amorphous (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Hydrochloride To a solution of (S)-4-(((R)-6-(2-chloro-4-fluorophenyl)-5-(methoxycarbonyl)-2-(thiazol-2-yl)-3,6-dihydropyrimidin-4-yl)methyl)morpholine-3-carboxylic acid (650 mg) in ethyl acetate (4.0 mL) was added a solution of hydrochloric acid in ethyl acetate (0.635 mL, 3.11 mol/L) dropwise at room temperature. After the addition, additional ethyl acetate (4.0 mL) was added dropwise. The resulting mixture was stirred at room temperature for 12 hours, then remove the solvent was removed, the residue was dried in vacuo at 25° C. to give the compound named (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic acid hydrochloride as a yellow solid (650 mg, productivity: 93.1%). The compound was characterized by the following spectroscopic data: $^1$H NMR (400 MHz, DMSO-d$_6$) δ (ppm): 12.52 (br, 1H), 9.86 (s, 1H), 8.03 (d, 1H), 7.94 (d, 1H), 7.43-7.38 (m, 2H), 7.16 (td, 1H), 6.04 (s, 1H), 4.24 (d, 1H), 4.06-3.97 (m, 2H), 3.84 (dd, 1H), 3.73-3.66 (m, 2H), 3.64-3.59 (m, 1H), 3.51 (s, 3H), 3.10-3.06 (m, 1H), 2.43-2.39 (m, 1H).

Figure 10:
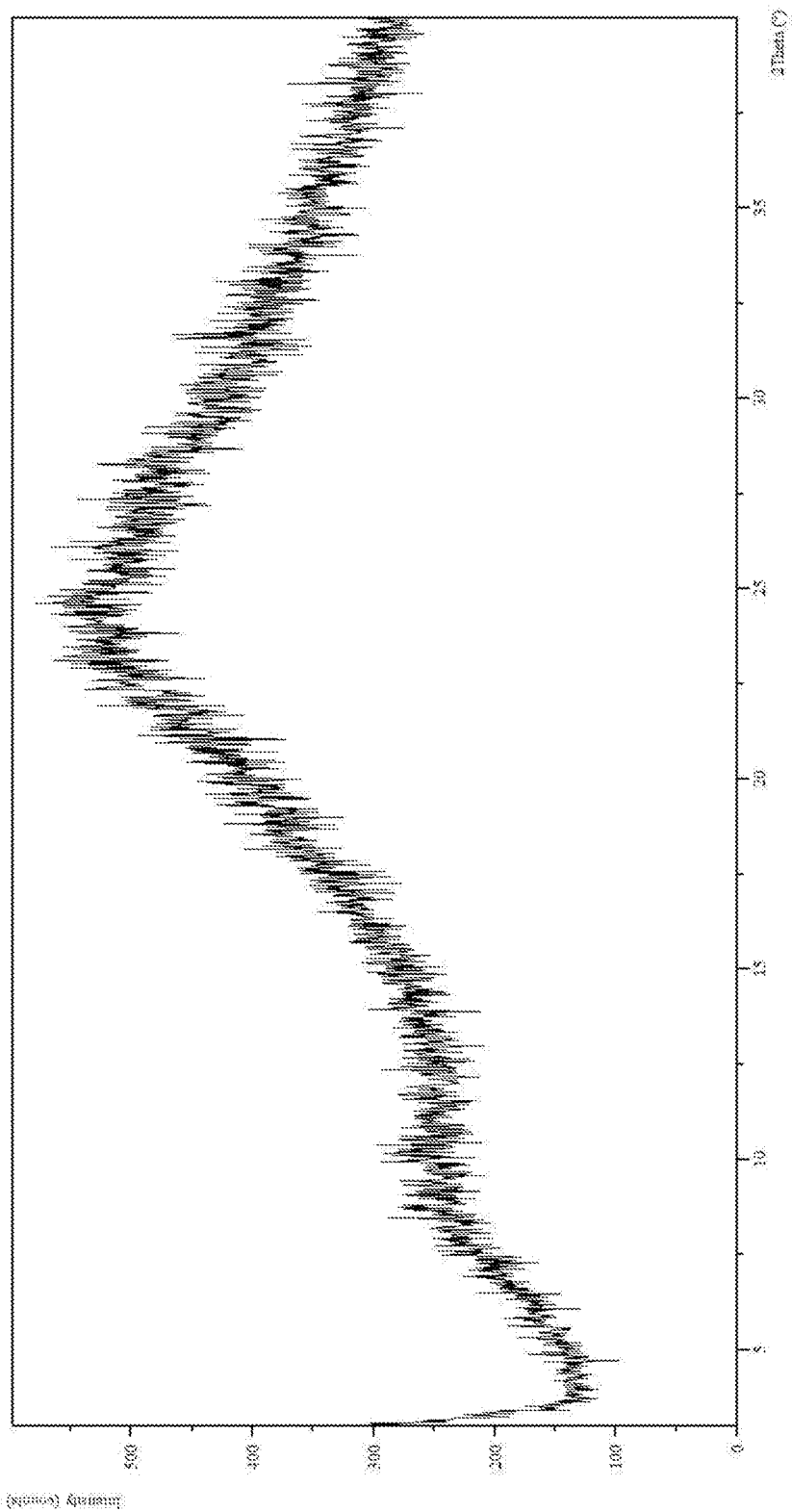
FIG. 10 provides an X-ray powder diffraction (XRPD) pattern of amorphous hydrochloride of the compound of formula (Ia).

2. Identification of Amorphous (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Hydrochloride The XRPD pattern was analyzed and identified by using Empyrean X-ray powder diffraction (XRPD) with Cu-Kα radiation, experimental results are shown in FIG. 10.

Example 13: Preparation and Identification of Crystalline Form I(B) of (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Hydrochloride

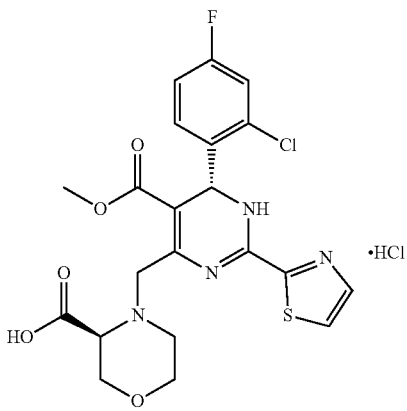 [SMILES: COC(=O)C1=C(CN2CCOC[C@H]2C(=O)O)N=C(c2nccs2)N[C@H]1c1ccc(F)cc1Cl ; Cl]

1. Preparation of Crystalline Form I(B) of (S)-4-(((R)-6-(2-chloro-4-fluorophenyl)-5-(methoxycarbonyl)-2-(thiazol-22-yl)-1,6-dihydropyrimidin-4-yl)methyl)morpholine-3-carboxylic Acid Hydrochloride To a solution of (S)-4-(((R)-6-(2-chloro-4-fluorophenyl)-5-(methoxycarbonyl)-2-(thiazol-2-yl)-3,6-dihydropyrimidin-4-yl)methyl)morpholine-3-carboxylic acid (100 mg) in ethyl acetate (1.0 mL) was added a solution of hydrochloric acid in ethyl acetate (0.13 mL, 3.11 mol/L) dropwise at room temperature. After the addition, further ethyl acetate (1.0 mL) was added dropwise. The mixture was stirred at room temperature for 7 hours, then remove the solvent, additional ethyl acetate (4.0 mL) was added, the resulting mixture was stirred at 60° C. for 4.5 hours, then cooled down to room temperature. The resulting mixture was stirred at room temperature for 12 hours, filtered, the residue was dried in vacuo to give the compound named (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic acid hydrochloride having crystalline form I(B) as a yellow solid (8 mg, productivity: 7.5%). The compound was characterized by the following spectroscopic data: $^1$H NMR (400 MHz, DMSO-d$_6$) δ (ppm): 12.52 (br, 1H), 9.86 (s, 1H), 8.03 (d, 1H), 7.94 (d, 1H), 7.43-7.38 (m, 2H), 7.16 (td, 1H), 6.04 (s, 1H), 4.24 (d, 1H), 4.06-3.97 (m, 2H), 3.84 (dd, 1H), 3.73-3.66 (m, 2H), 3.64-3.59 (m, 1H), 3.51 (s, 3H), 3.10-3.06 (m, 1H), 2.43-2.39 (m, 1H).

Figure 5:
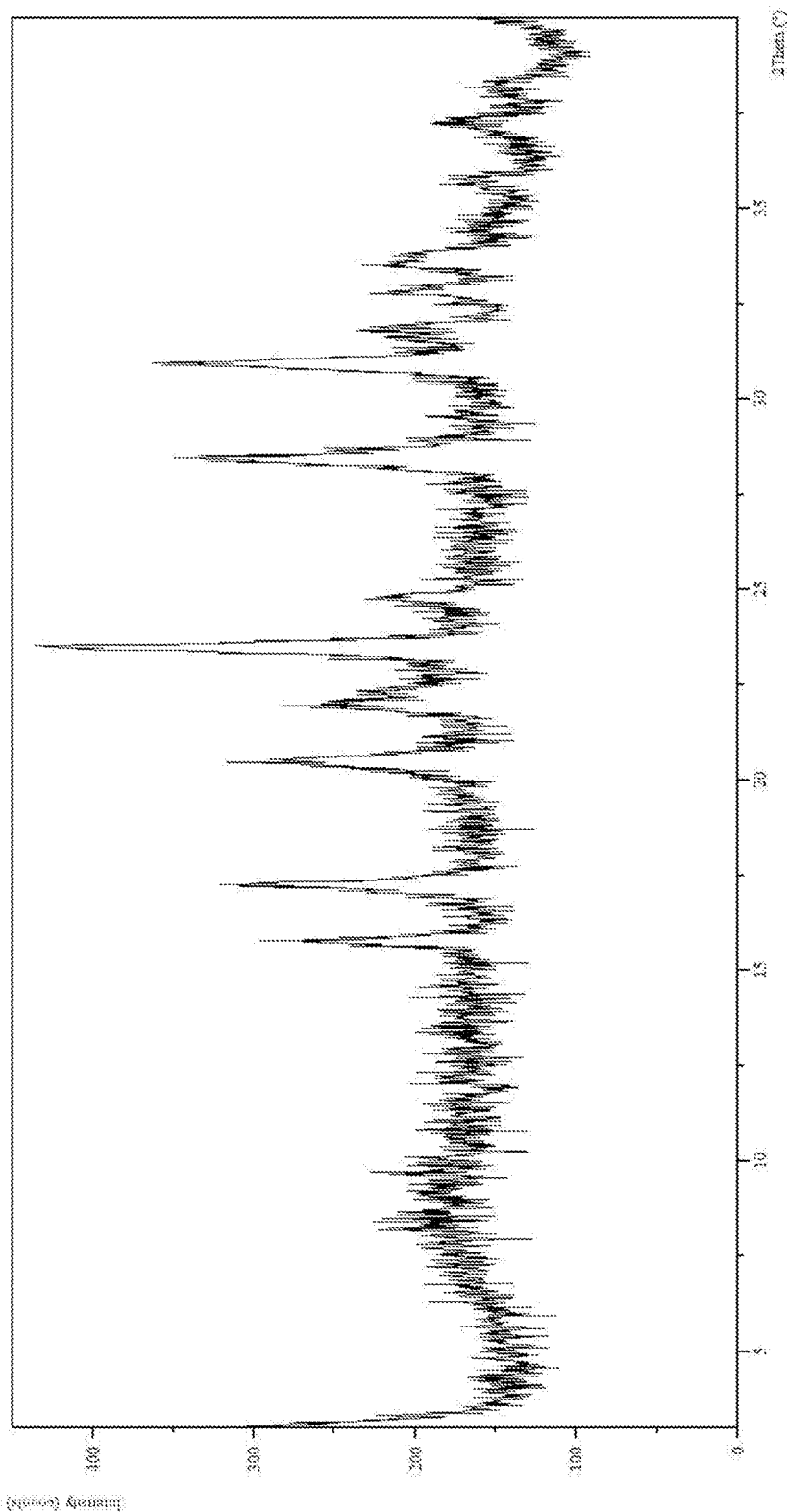
FIG. 5 provides an X-ray powder diffraction (XRPD) pattern of hydrochloride having crystalline form I(B) of the compound of formula (Ia).

2. Identification of Crystalline Form I(B) of (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Hydrochloride The XRPD pattern was analyzed and identified by using Empyrean X-ray powder diffraction (XRPD) with Cu-Kα radiation, experimental results are shown in FIG. 5, having the following characteristic peaks expressed in degrees 2θ at 15.73°, 17.21°, 20.44°, 22.04°, 23.44°, 24.73°, 28.39°, 30.86°, 31.73°, 32.78°, 33.61°, 35.63°, 37.16° and 38.13°. The error margin in 2θ of the characteristic peaks is ±0.2°.

Example 14: Preparation and Identification of Crystalline Form II of (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Hydrochloride

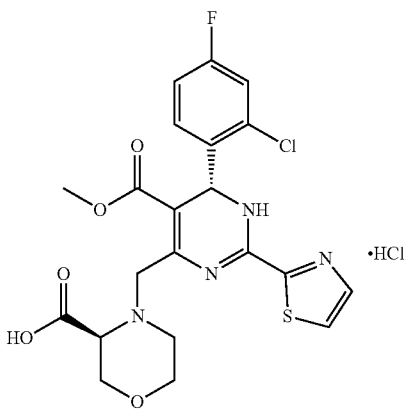 [SMILES: COC(=O)C1=C(CN2CCOC[C@H]2C(=O)O)N=C(c2nccs2)N[C@H]1c1ccc(F)cc1Cl ; Cl]

1. Preparation of Crystalline Form II of (S)-4-(((R)-6-(2-chloro-4-fluorophenyl)-5-(methoxycarbonyl)-2-(thiazol-2-yl)-1,6-dihydropyrimidin-4-yl)methyl) morpholine-3-carboxylic Acid Hydrochloride To a 50 mL of three-neck flask was added sequentially water (36 mL) and aqueous hydrochloric acid solution (37.5%, 4.5 mL, 54 mmol) with stirring, the mixture was heated to 60° C., (S)-4-(((R)-6-(2-chloro-4-fluorophenyl)-5-(methoxycarbonyl)-2-(thiazol-2-yl)-3,6-dihydropyrimidin-4-yl)methyl)morpholine-3-carboxylic acid (4.5 g, 9 mmol) was added in portions, after the solid was dissolved completely, the mixture was kept at the temperature and stirred for 30 minutes, the heating was stopped, the mixture was cooled naturally to 25-35° C., kept at the temperature and stirred for 12 hours and filtered, the filter cake was washed with water (25 mL), dried in vacuo at 25-35° C. for 1 hours, then dried in vacuo at 70° C. for 12 hours to give a compound named (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic acid hydrochloride having crystalline form II as a yellow solid (2.6 g, productivity: 55%).

Figure 6:
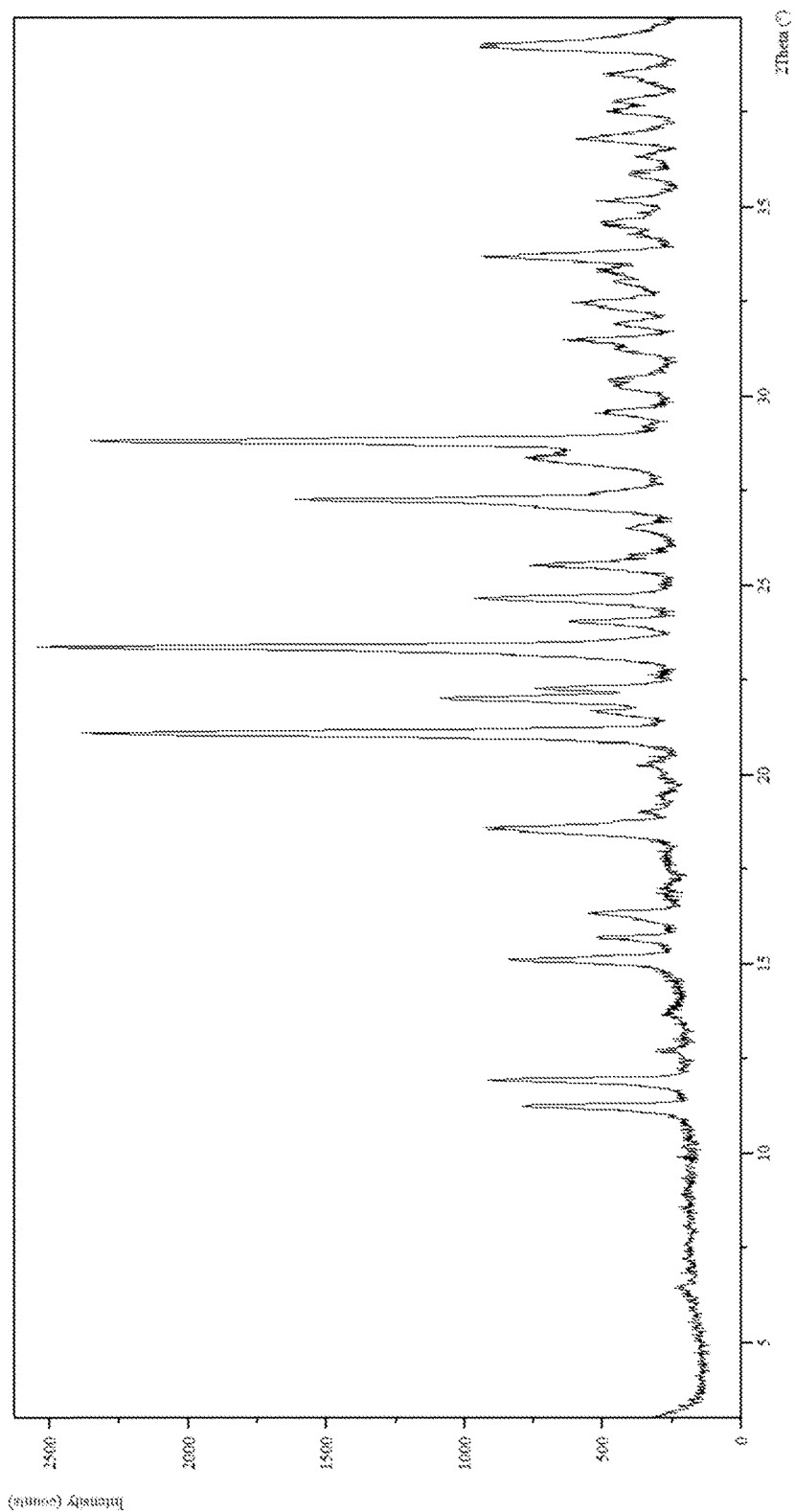
FIG. 6 provides an X-ray powder diffraction (XRPD) pattern of hydrochloride having crystalline form II of the compound of formula (Ia).

2. Identification of Crystalline Form II of (S)-4-(((R)-6-(2-chloro-4-fluorophenyl)-5-(methoxycarbonyl)-2-(thiazol-2-yl)-1,6-dihydropyrimidin-4-yl) methyl)morpholine-3-carboxylic Acid Hydrochloride (1) The XRPD pattern was analyzed and identified by using Empyrean X-ray powder diffraction (XRPD) with Cu-Kα radiation, experimental results are shown in FIG. 6, having the following characteristic peaks expressed in degrees 2θ at 6.390, 11.20°, 11.90°, 12.68°, 13.68°, 15.060, 15.65°, 16.270, 18.53°, 19.000, 20.21°, 21.040, 21.61°, 21.960, 22.24°, 23.300, 24.00°, 24.600, 25.50°, 26.480, 27.20°, 28.320, 28.75°, 29.510, 30.31°, 31.390, 31.87°, 32.400, 33.62°, 34.53°, 35.12°, 35.80°, 36.28°, 36.76°, 37.48°, 37.74°, 38.44° and 39.21°. The error margin in 2θ of the characteristic peaks is ±0.2°.

Figure 7:
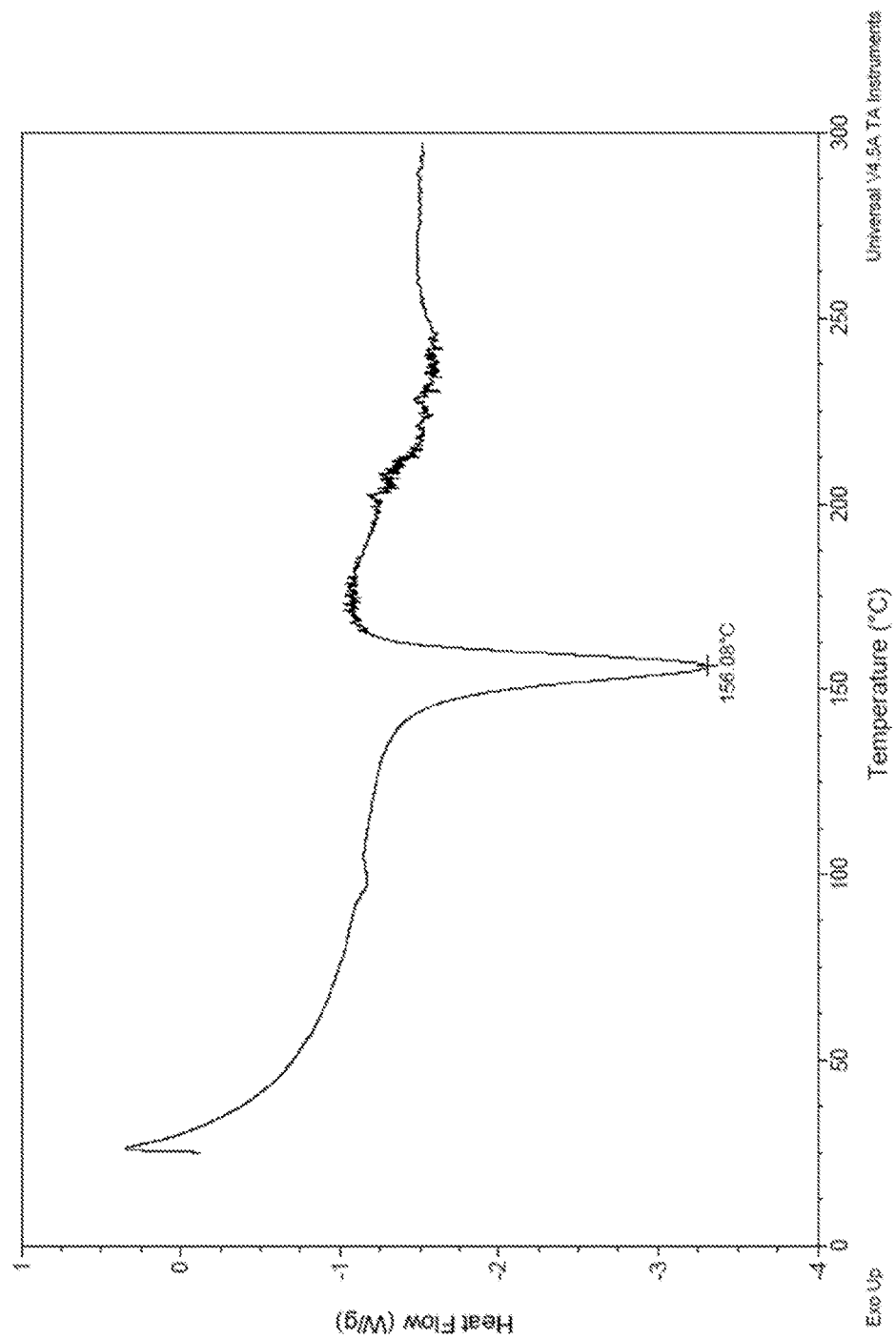
FIG. 7 provides a differential scanning calorimetry (DSC) thermogram of hydrochloride having crystalline form II of the compound of formula (Ia).

(2) The DSC thermogram was analyzed and identified by using TA Q2000 differential scanning calorimetry (DSC) with a scan rate of 10° C./minute, experimental results are shown in FIG. 7, comprising an endothermic peak at 156.08° C. The error margin of the endothermic peaks is ±3° C.

Example 15: Preparation and Identification of Amorphous (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Nitrate

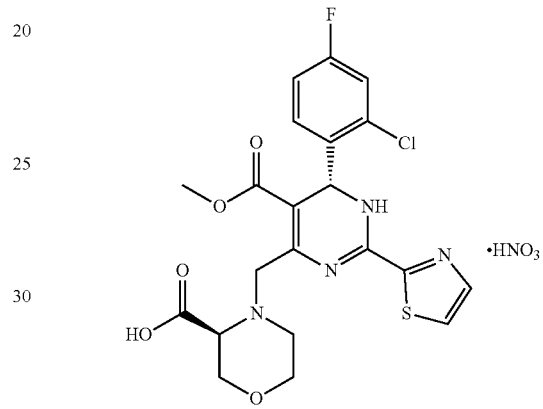

1. Preparation of Amorphous (S)-4-(((R)-6-(2-chloro-4-fluorophenyl)-5-(methoxycarbonyl)-2-(thiazol-22-yl)-1,6-dihydropyrimidin-4-yl)methyl)morpholine-3-carboxylic Acid Nitrate To a solution of (S)-4-(((R)-6-(2-chloro-4-fluorophenyl)-5-(methoxycarbonyl)-2-(thiazol-2-yl)-3,6-dihydropyrimidin-4-yl)methyl)morpholine-3-carboxylic acid (101 mg) in ethanol (1.0 mL) was added a mixed solution of nitric acid (38.0 mg, Mw=65%) and ethanol (0.5 mL) dropwise at room temperature. After the addition, the resulting mixture was reacted at room temperature for 12 hours, then dried over anhydrous sodium sulfate and filtered. The filtrate was concentrated and dried in vacuo at ° C. to give the compound named (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic acid nitrate as a yellow solid (72 mg, productivity: 63.8%).

Figure 18:
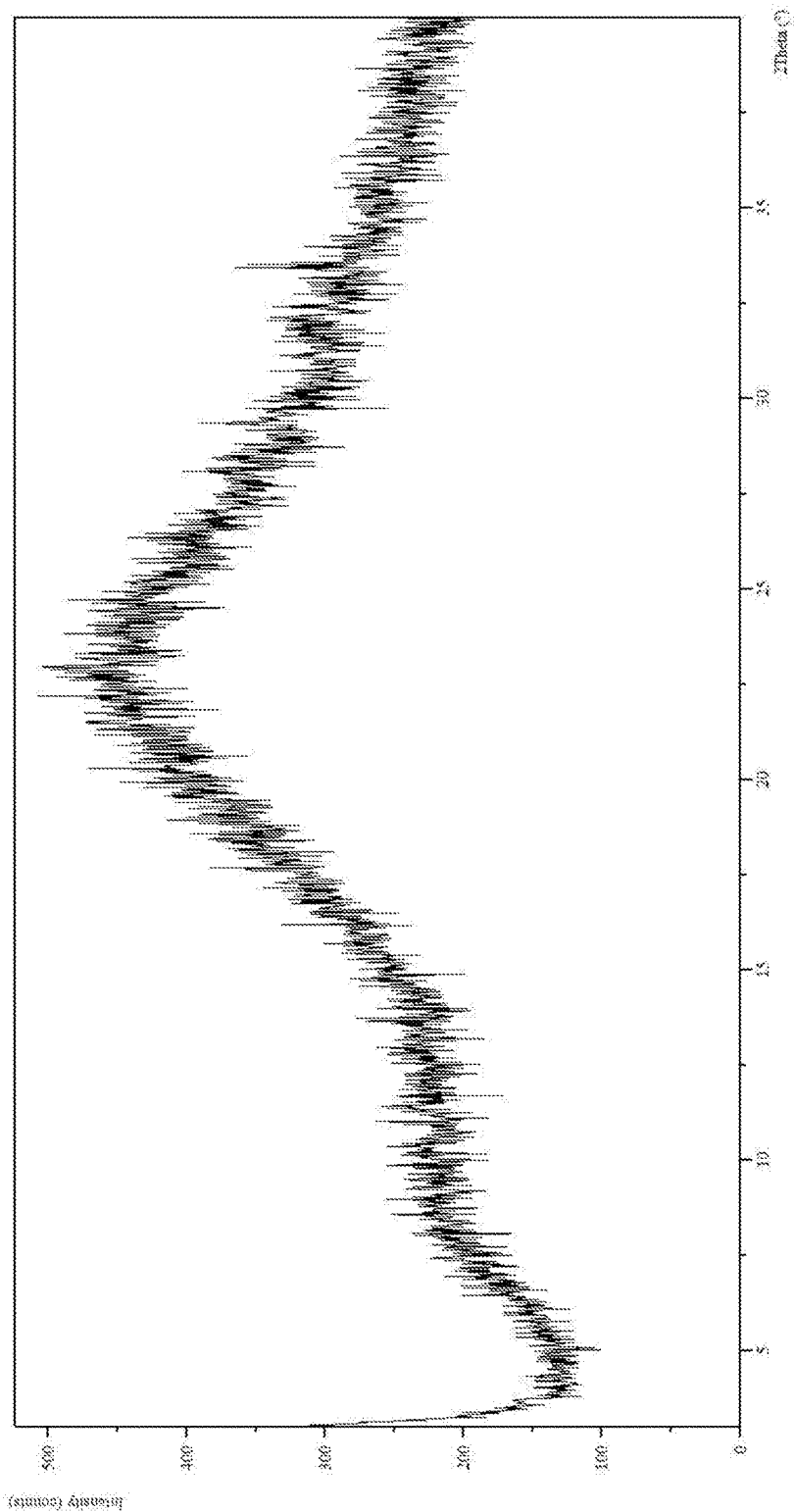
FIG. 18 provides an X-ray powder diffraction (XRPD) pattern of amorphous nitrate of the compound of formula (Ia).

2. Identification of Amorphous (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Nitrate The XRPD pattern was analyzed and identified by using Empyrean X-ray powder diffraction (XRPD) with Cu-Kα radiation, experimental results are shown in FIG. 18.

Example 16: Preparation and Identification of Amorphous (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid L-lysine Salt Example 17: Preparation and Identification of Amorphous (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Sodium Salt

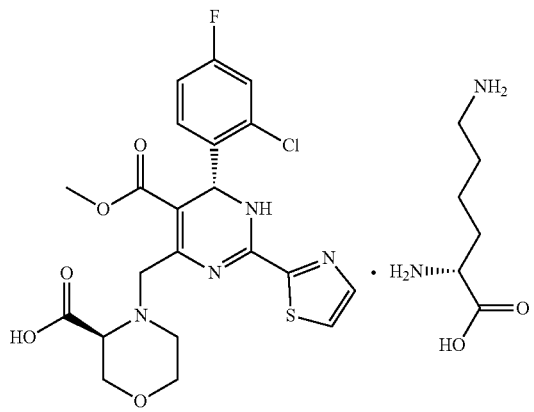 [SMILES: COC(=O)C1=C(CN2CCOC[C@H]2C(=O)O)N=C(c2nccs2)N[C@H]1c1ccc(F)cc1Cl ; NCCCC[C@@H](N)C(=O)O]

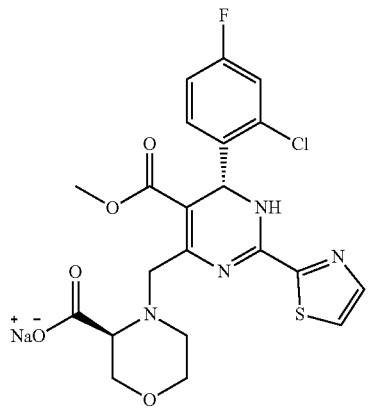

1. Preparation of Amorphous (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid L-lysine Salt 1. Preparation of Amorphous (S)-4-(((R)-6-(2-chloro-4-fluorophenyl)-5-(methoxycarbonyl)-2-(thiazol-22-yl)-1,6-dihydropyrimidin-4-yl)methyl)morpholine-3-carboxylic Acid Sodium Salt To a solution of (S)-4-(((R)-6-(2-chloro-4-fluorophenyl)-5-(methoxycarbonyl)-2-(thiazol-2-yl)-3,6-dihydropyrimidin-4-yl)methyl)morpholine-3-carboxylic acid (201 mg) in ethanol (2.0 mL) was added a solution of L-lysine (60 mg) in water (1.0 mL) dropwise at room temperature. After the addition, the mixture was reacted at room temperature for 12 hours, then the solvent was removed. To the residue was added ether (20.0 mL). The resulting mixture was stirred for at room temperature 12 hours, then the solvent was removed. The residue was dried in vacuo at 25° C. to give the compound named (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic acid L-lysine salt as a yellow solid (150 mg, productivity: 57.6%). The compound was characterized by the following spectroscopic data: $^1$H NMR (400 MHz, DMSO-$d_6$) δ (ppm): 7.99 (d, J=3.0 Hz, 1H), 7.87 (d, J=3.1 Hz, 1H), 7.39 (dt, J=9.0, 4.7 Hz, 2H), 7.18 (td, J=8.5, 2.5 Hz, 1H), 6.00 (s, 1H), 4.05 (d, J=15.9 Hz, 1H), 3.88-3.77 (m, 2H), 3.69 (s, 1H), 3.54 (s, 2H), 3.49 (s, 3H), 3.23 (s, 2H), 3.06 (d, J=6.6 Hz, 1H), 2.89 (d, J=11.0 Hz, 1H), 2.73 (t, J=6.9 Hz, 2H), 2.41-2.34 (m, 1H), 1.72-1.27 (m, 6H).

To a solution of (S)-4-(((R)-6-(2-chloro-4-fluorophenyl)-5-(methoxycarbonyl)-2-(thiazol-2-yl)-3,6-dihydropyrimidin-4-yl)methyl)morpholine-3-carboxylic acid (650 mg) in a mixed solution of isopropanol (19.0 mL) and n-heptane (8.0 mL) was added a solution of sodium iso-octoate (1.08 mg) in isopropanol (8.0 mL) dropwise at room temperature. After the addition, the resulting mixture was stirred at room temperature for 12.0 hours, and filtered by suction. The filter cake was washed with n-heptane (10.0 mL×2) and dried in vacuo at 60° C. to give the compound named (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic acid sodium salt as a yellow solid (1.72 mg, productivity: 66.7%). The compound was characterized by the following spectroscopic data: $^1$H NMR (600 MHz, DMSO-$d_6$) δ (ppm): 7.96 (d, J=3.1 Hz, 1H), 7.84 (d, J=3.1 Hz, 1H), 7.41-7.35 (m, 2H), 7.19 (td, J=8.5, 2.6 Hz, 1H), 5.98 (s, 1H), 4.03 (d, J=15.5 Hz, 1H), 3.87 (dd, J=10.9, 3.1 Hz, 1H), 3.77 (d, J=15.6 Hz, 1H), 3.70 (d, J=11.1 Hz, 1H), 3.52-3.46 (m, 5H), 3.45-3.40 (m, 1H), 2.93 (d, J=9.3 Hz, 1H), 2.83 (d, J=11.6 Hz, 1H), 2.38 (td, J=11.3, 3.1 Hz, 1H).

Figure 25:
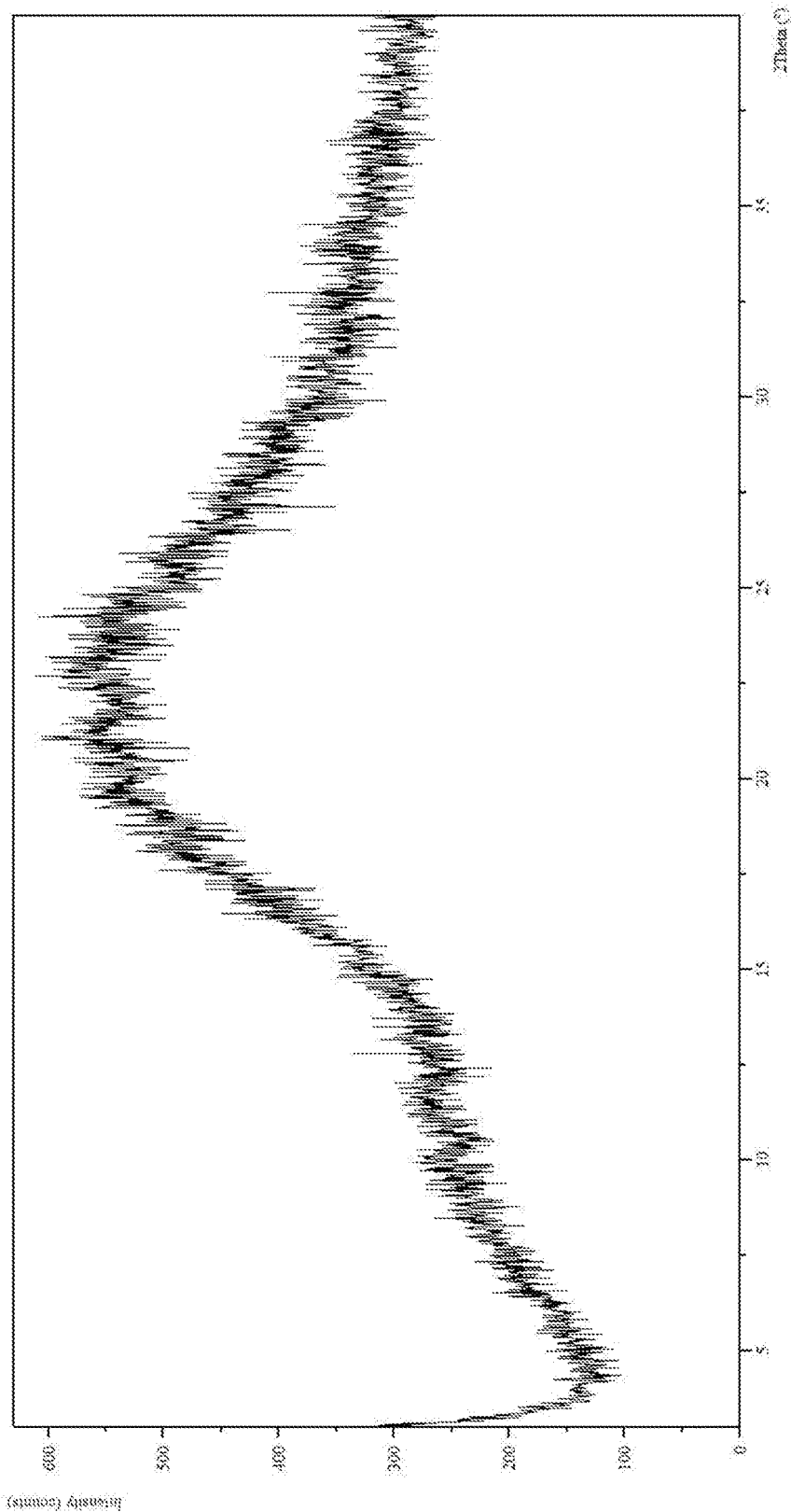
FIG. 25 provides an X-ray powder diffraction (XRPD) pattern of L-lysine amorphous of the compound of formula (Ia).

2. Identification of Amorphous (S)-4-(((R)-6-(2-chloro-4-fluorophenyl)-5-(methoxycarbonyl)-2-(thiazol-22-yl)-1,6-dihydropyrimidin-4-yl)methyl)morpholine-3-carboxylic Acid L-lysine Salt 2. Identification of Amorphous (S)-4-(((R)-6-(2-chloro-4-fluorophenyl)-5-(methoxycarbonyl)-2-(thiazol-22-yl)-1,6-dihydropyrimidin-4-yl)methyl)morpholine-3-carboxylic Acid Sodium Salt The XRPD pattern was analyzed and identified by using Empyrean X-ray powder diffraction (XRPD) with Cu-Kα radiation, experimental results are shown in FIG. 25.

Figure 23:
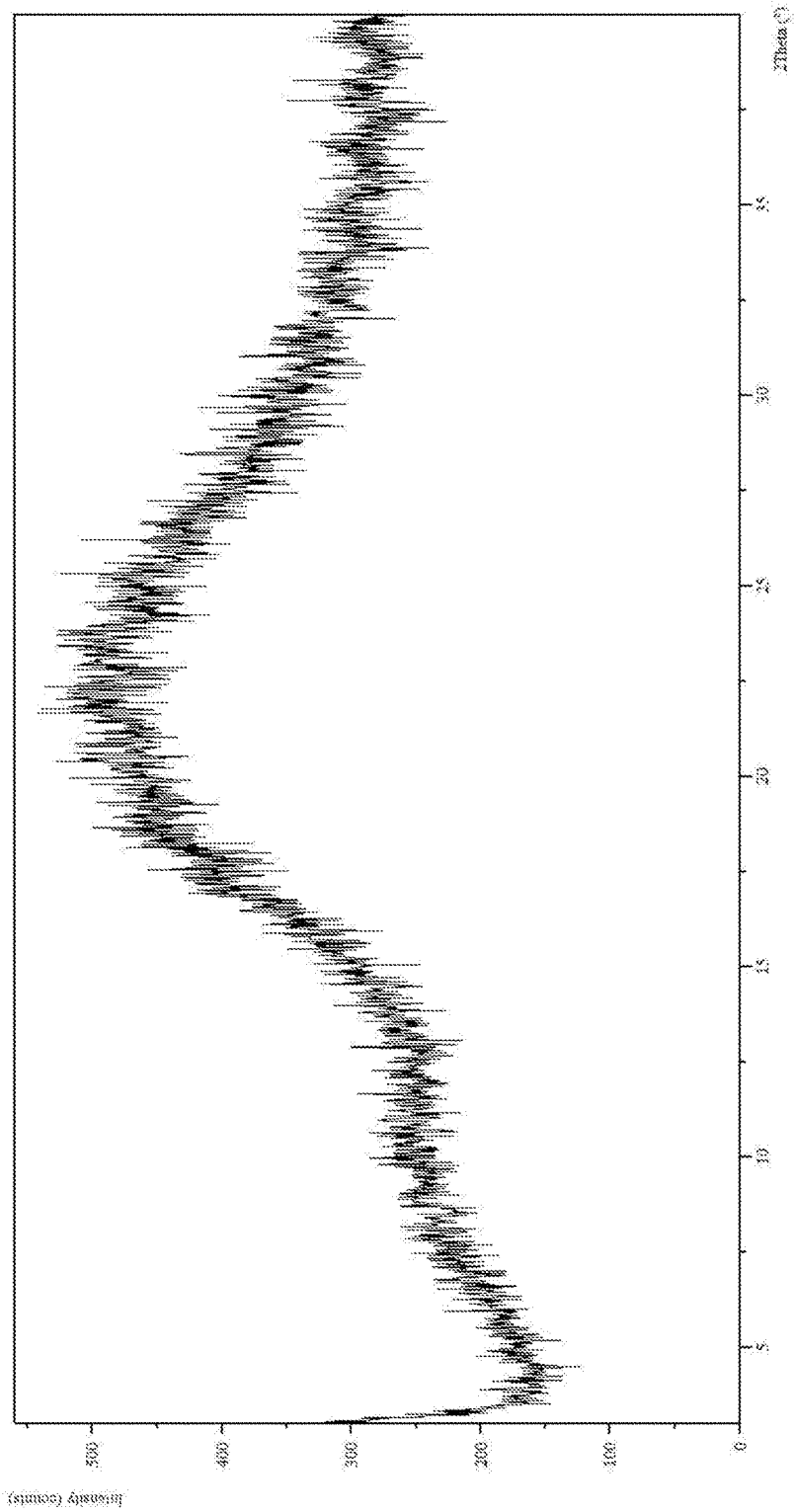
FIG. 23 provides an X-ray powder diffraction (XRPD) pattern of sodium salt amorphous of the compound of formula (Ia).

The XRPD pattern was analyzed and identified by using Empyrean X-ray powder diffraction (XRPD) with Cu-Kα radiation, experimental results are shown in FIG. 23.

Example 18: Preparation and Identification of Amorphous (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Calcium Salt

Example 19: Preparation and Identification of Crystalline Form I(D) of (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Calcium Salt

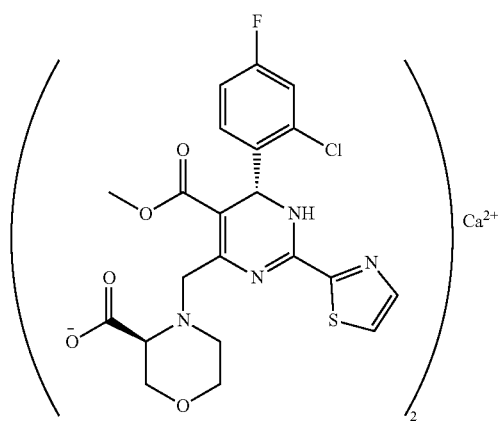

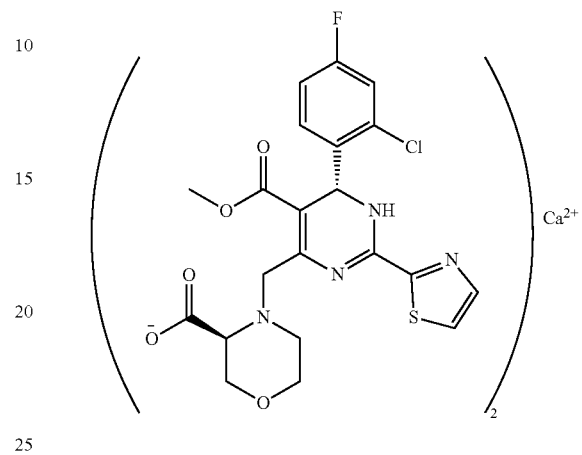

1. Preparation of Amorphous (S)-4-(((R)-6-(2-chloro-4-fluorophenyl)-5-(methoxycarbonyl)-2-(thiazol-22-yl)-1,6-dihydropyrimidin-4-yl)methyl)morpholine-3-carboxylic Acid Calcium Salt To a solution of (S)-4-(((R)-6-(2-chloro-4-fluorophenyl)-5-(methoxycarbonyl)-2-(thiazol-2-yl)-3,6-dihydropyrimidin-4-yl)methyl)morpholine-3-carboxylic acid (1.5 g) in ethanol (3.0 mL) was added a solution of sodium hydroxide (120 mg) in water (1.0 mL) dropwise at room temperature, the resulting mixture was stirred at room temperature for 12 hours. Then the mixture was added a solution of calcium chloride (500 mg) in water (1.0 mL). After the addition, additional water (5.0 mL) was added to the mixture and stirred at room temperature for 2.0 hours, then the resulting mixture was filtered by suction. The filter cake was washed with water (5.0 mL×2) and dried in vacuo at 25° C. to give the compound named (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic acid calcium salt as a yellow solid (1.35 mg, productivity: 83.3%). The compound was characterized by the following spectroscopic data: $^1$H NMR (400 MHz, DMSO-$d_6$) δ (ppm): 7.81 (s, 1H), 7.67 (d, J=3.2 Hz, 1H), 7.36-7.23 (m, 2H), 7.10 (t, J=8.5 Hz, 1H), 5.86 (s, 1H), 4.80 (d, J=14.9 Hz, 1H), 3.95 (d, J=6.6 Hz, 1H), 3.75-3.64 (m, 2H), 3.58 (s, 1H), 3.40 (s, 3H), 3.25 (s, 1H), 3.09 (s, 1H), 2.81 (s, 1H), 2.26 (d, J=13.7 Hz, 1H).

Figure 24:
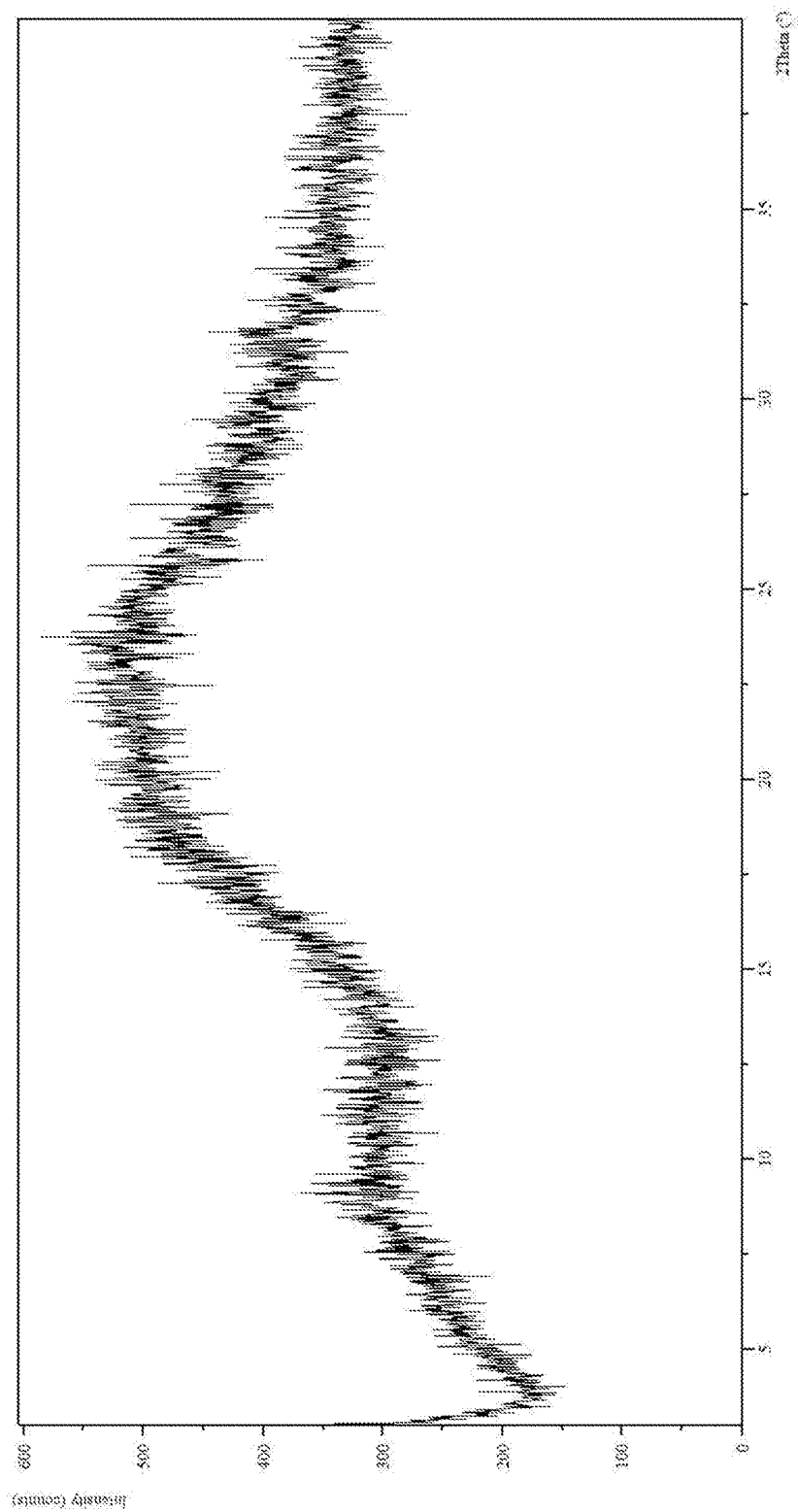
FIG. 24 provides an X-ray powder diffraction (XRPD) pattern of calcium salt amorphous of the compound of formula (Ia).

2. Identification of Amorphous (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Calcium Salt The XRPD pattern was analyzed and identified by using Empyrean X-ray powder diffraction (XRPD) with Cu-Kα radiation, experimental results are shown in FIG. 24.

1. Preparation of Crystalline Form I(D) of (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Calcium Salt To a solution of (S)-4-(((R)-6-(2-chloro-4-fluorophenyl)-5-(methoxycarbonyl)-2-(thiazol-2-yl)-3,6-dihydropyrimidin-4-yl)methyl)morpholine-3-carboxylic acid (247 mg) in acetonitrile (1.0 mL) was added a solution of sodium hydroxide (48 mg) in water (1.0 mL) dropwise at room temperature. After the addition, the resulting mixture was reacted at room temperature for 1 hour. Then the mixture was added a solution of calcium chloride (29 mg) in water (1.0 mL) dropwise. After the addition, the resulting mixture was stirred for 3.0 hours, then filtered by suction. The filter cake was washed with water (5.0 mL×2) and dried in vacuo at 60° C. for 8.0 hours to give the compound named (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic acid calcium salt having crystalline form I(D) as a yellow solid (130 mg, productivity: 48.8%). The compound was characterized by the following spectroscopic data: $^1$H NMR (400 MHz, DMSO-$d_6$) δ (ppm): 7.81 (s, 1H), 7.67 (d, J=3.2 Hz, 1H), 7.36-7.23 (m, 2H), 7.10 (t, J=8.5 Hz, 1H), 5.86 (s, 1H), 4.80 (d, J=14.9 Hz, 1H), 3.95 (d, J=6.6 Hz, 1H), 3.75-3.64 (m, 2H), 3.58 (s, 1H), 3.40 (s, 3H), 3.25 (s, 1H), 3.09 (s, 1H), 2.81 (s, 1H), 2.26 (d, J=13.7 Hz, 1H).

Figure 21:
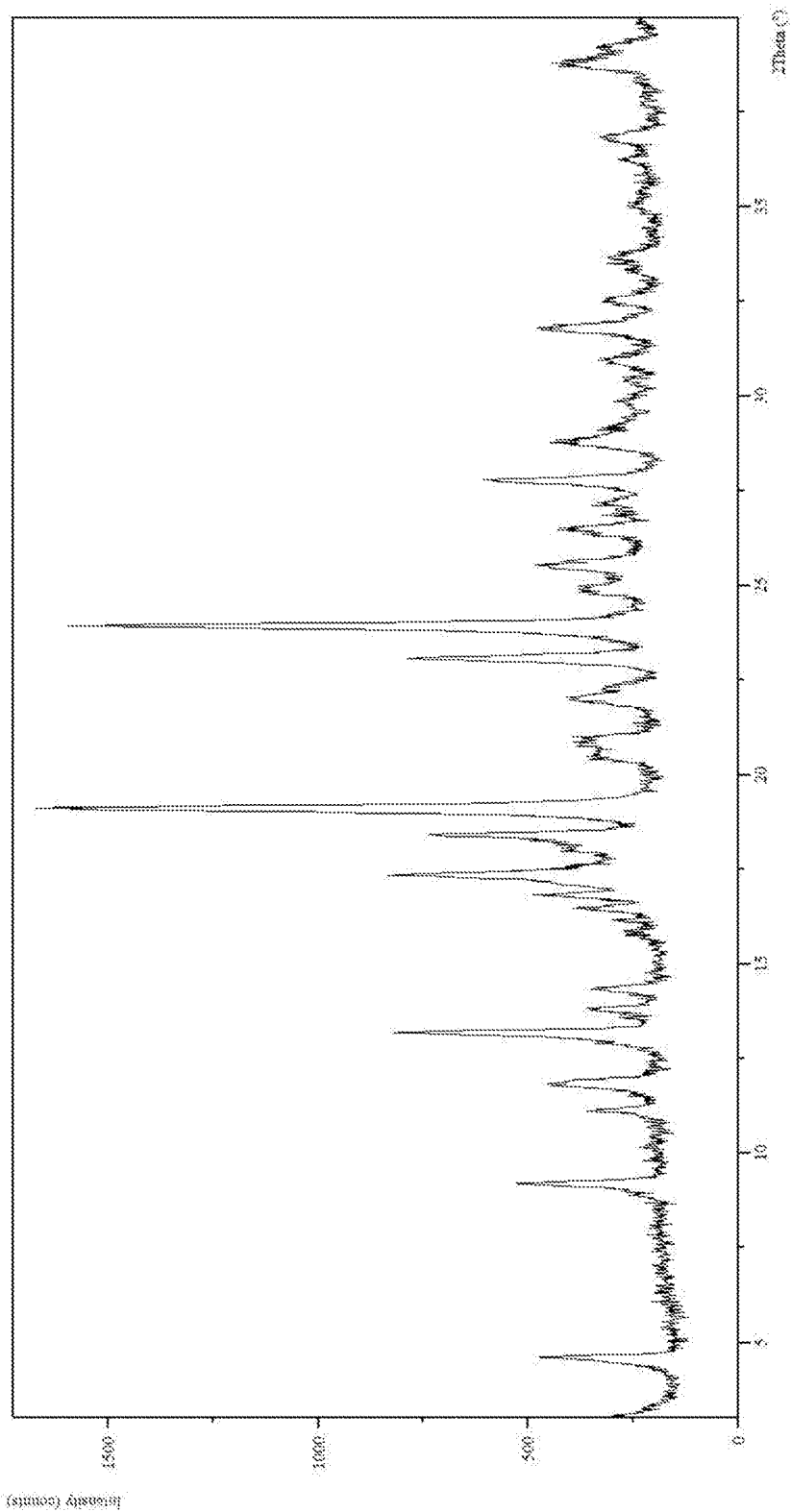
FIG. 21 provides an X-ray powder diffraction (XRPD) pattern of calcium salt having crystalline form I(D) of the compound of formula (Ia).

2. Identification of Crystalline Form I(D) of (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Calcium Salt (1) The XRPD pattern was analyzed and identified by using Empyrean X-ray powder diffraction (XRPD) with Cu-Kα radiation as shown in FIG. 21, having the following characteristic peaks expressed in degrees 2θ at 4.540, 9.14°, 11.09°, 11.79°, 13.13°, 13.75°, 14.29°, 16.43°, 16.78°, 17.310, 18.33°, 19.070, 20.45°, 20.810, 22.01°, 23.020, 23.88°, 24.870, 25.48°, 26.430, 27.71°, 28.80°, 30.87°, 31.75°, 32.48°, 33.55°, 35.04°, 36.18°, 36.76°, 38.73° and 39.16°. The error margin in 2θ of the characteristic peaks is ±0.2°.

Figure 22:
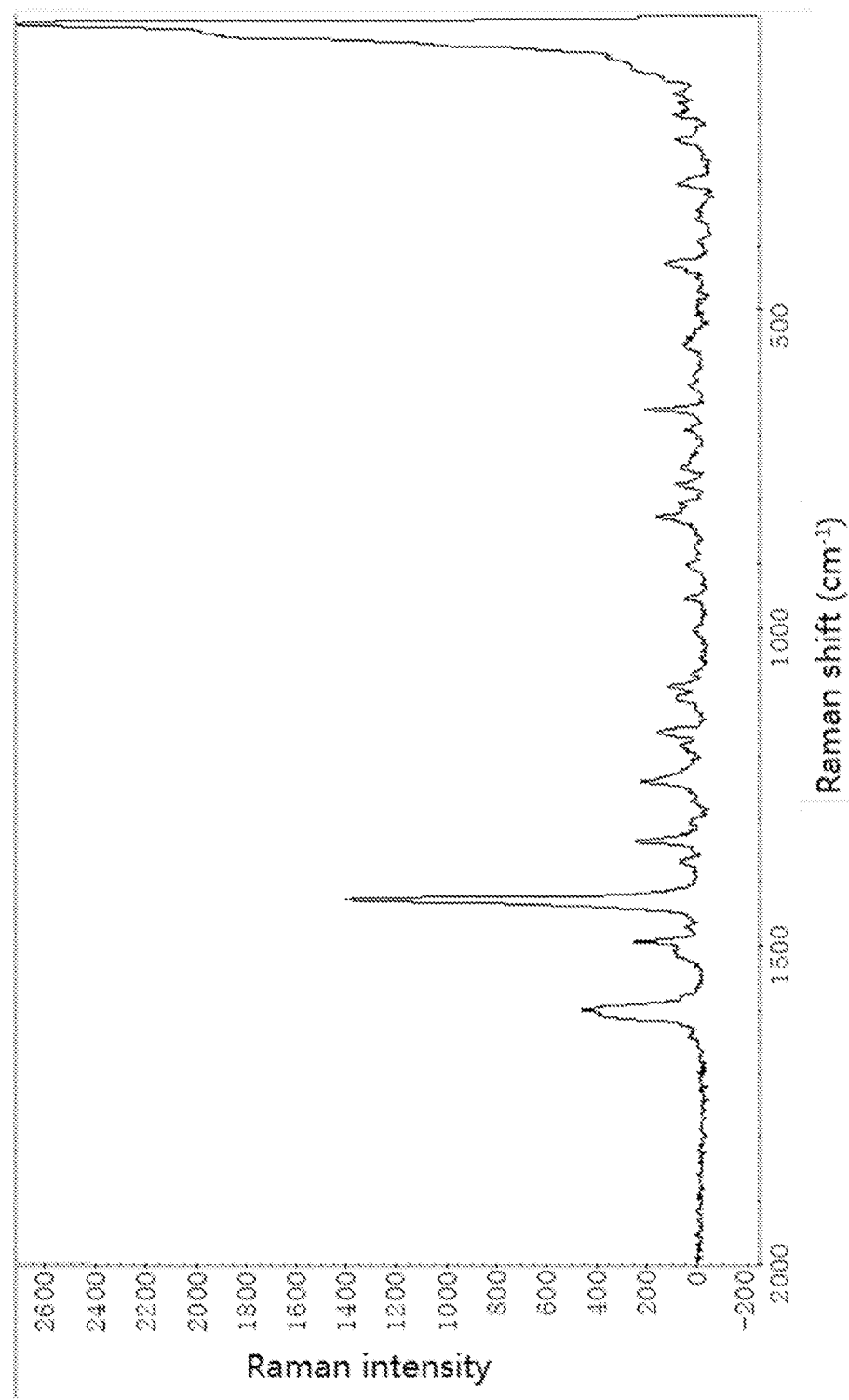
FIG. 22 provides a Raman spectrogram of calcium salt having crystalline form I(D) of the compound of formula (Ia).

(2) The Raman spectrogram was analyzed and identified by using Thermo DXR confocal laser Raman spectrometer as shown in FIG. 22, having the following absorption peaks at 52, 82, 107, 139, 194, 235, 254, 301, 355, 390, 425, 440, 497, 551, 600, 622, 656, 690, 720, 749, 773, 802, 824, 852, 900, 953, 1009, 1069, 1093, 1113, 1167, 1211, 1242, 1309, 1336, 1369, 1426, 1494 and 1597 cm$^{-1}$. The error margin of the absorption peaks is ±2 cm$^{-1}$.

Example 20: Preparation and Identification of Amorphous (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid L-tartrate

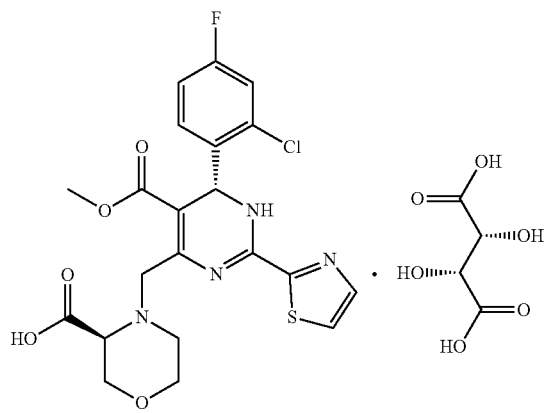 [SMILES: COC(=O)C1=C(CN2CCOC[C@H]2C(=O)O)N=C(c2nccs2)N[C@H]1c1ccc(F)cc1Cl ; O=C(O)[C@H](O)[C@@H](O)C(=O)O]

1. Preparation of Amorphous (S)-4-(((R)-6-(2-chloro-4-fluorophenyl)-5-(methoxycarbonyl)-2-(thiazol-22-yl)-1,6-dihydropyrimidin-4-yl)methyl)morpholine-3-carboxylic Acid L-tartrate To a solution of (S)-4-(((R)-6-(2-chloro-4-fluorophenyl)-5-(methoxycarbonyl)-2-(thiazol-2-yl)-3,6-dihydropyrimidin-4-yl)methyl)morpholine-3-carboxylic acid (100 mg) in methanol (4.0 mL) was added a solution of L-tartaric acid (32 mg) in methanol (6.0 mL) dropwise. After the addition, the resulting mixture was reacted at room temperature for 17 hours. Then remove the solvent and dried in vacuo at 25° C. to give the compound named (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic acid L-tartrate as a yellow solid (130 mg, productivity: 99.8%). The compound was characterized by the following spectroscopic data: $^1$H NMR (400 MHz, DMSO-d$_6$) δ (ppm): 9.86 (s, 1H), 8.02 (d, J=3.1 Hz, 1H), 7.93 (d, J=3.1 Hz, 1H), 7.40 (dt, J=9.0, 4.6 Hz, 2H), 7.15 (td, J=8.5, 2.6 Hz, 1H), 6.04 (s, 1H), 4.31 (s, 2H), 4.24 (d, J=17.6 Hz, 1H), 4.10-3.91 (m, 2H), 3.83 (dd, J=11.1, 3.1 Hz, 1H), 3.74-3.64 (m, 2H), 3.61 (t, J=3.6 Hz, 1H), 3.51 (s, 3H), 3.08 (t, J=8.5 Hz, 1H), 2.40 (d, J=12.0 Hz, 1H).

Figure 19:
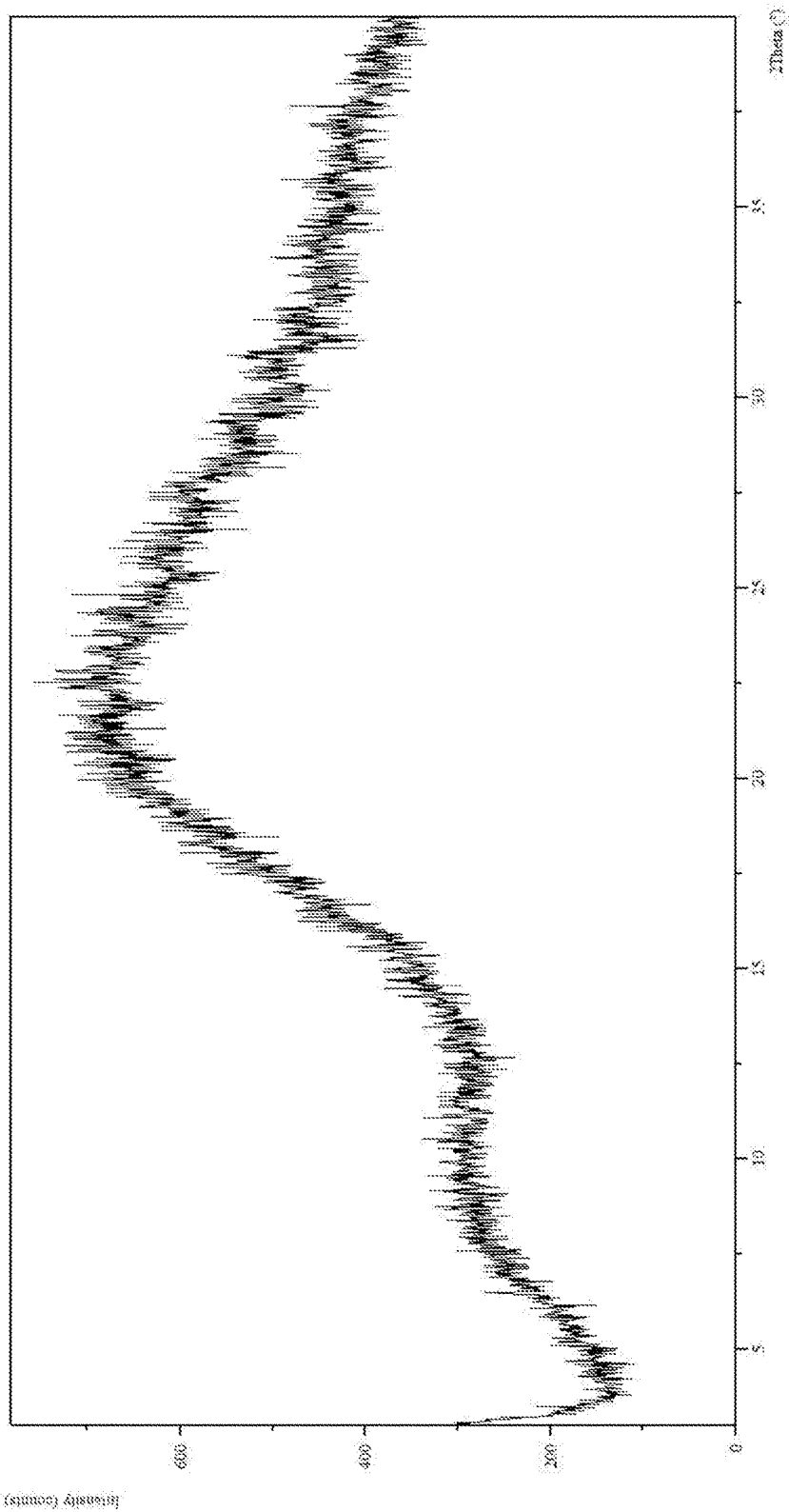
FIG. 19 provides an X-ray powder diffraction (XRPD) pattern of amorphous L-tartrate of the compound of formula (Ia).

2. Identification of Amorphous (S)-4-(((R)-6-(2-chloro-4-fluorophenyl)-5-(methoxycarbonyl)-2-(thiazol-22-yl)-1,6-dihydropyrimidin-4-yl)methyl)morpholine-3-carboxylic Acid L-tartrate The XRPD pattern was analyzed and identified by using Empyrean X-ray powder diffraction (XRPD) with Cu-Kα radiation, experimental results are shown in FIG. 19.

Example 21: Preparation and Identification of Crystalline Form I(E) of (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Mesylate 1. Preparation of Crystalline Form I(E) of (S)-4-(((R)-6-(2-chloro-4-fluorophenyl)-5-(methoxycarbonyl)-2-(thiazol-22-yl)-1,6-dihydropyrimidin-4-yl)methyl)morpholine-3-carboxylic Acid Mesylate To a dry flask was added sequentially (S)-4-(((R)-6-(2-chloro-4-fluorophenyl)-5-(methoxycarbonyl)-2-(thiazol-2-yl)-3,6-dihydropyrimidin-4-yl)methyl)morpholine-3-carboxylic acid (2 g, 4.0 mmol) and tetrahydrofuran (10 mL) with stirring at 25° C., after the solid was dissolved completely, to the mixture was added dropwise methylsulfonic acid (0.39 g, 4.0 mmol) in tetrahydrofuran (10 mL). After the addition, the resulting mixture was stirred for 8 hours. The stirring was stopped and the mixture was held still for 30 minutes. The supernatant was poured off and the operation was repeated 3 times. n-propyl acetate (20 mL) was added and the mixture was stirred for 2 hours at 25° C., then filtered by suction. The filter cake was washed with n-propyl acetate (10 mL×2) and transferred quickly to a single-neck flask, then dried in vacuo at 50° C. for 12 hours to give the compound named (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic acid mesylate having crystalline form I(E) as a yellow solid (1.83 g, productivity: 77%).

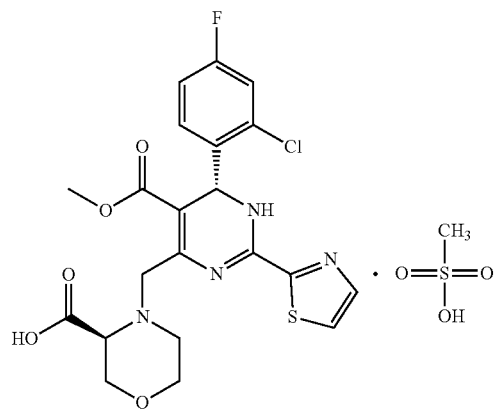

Figure 26:
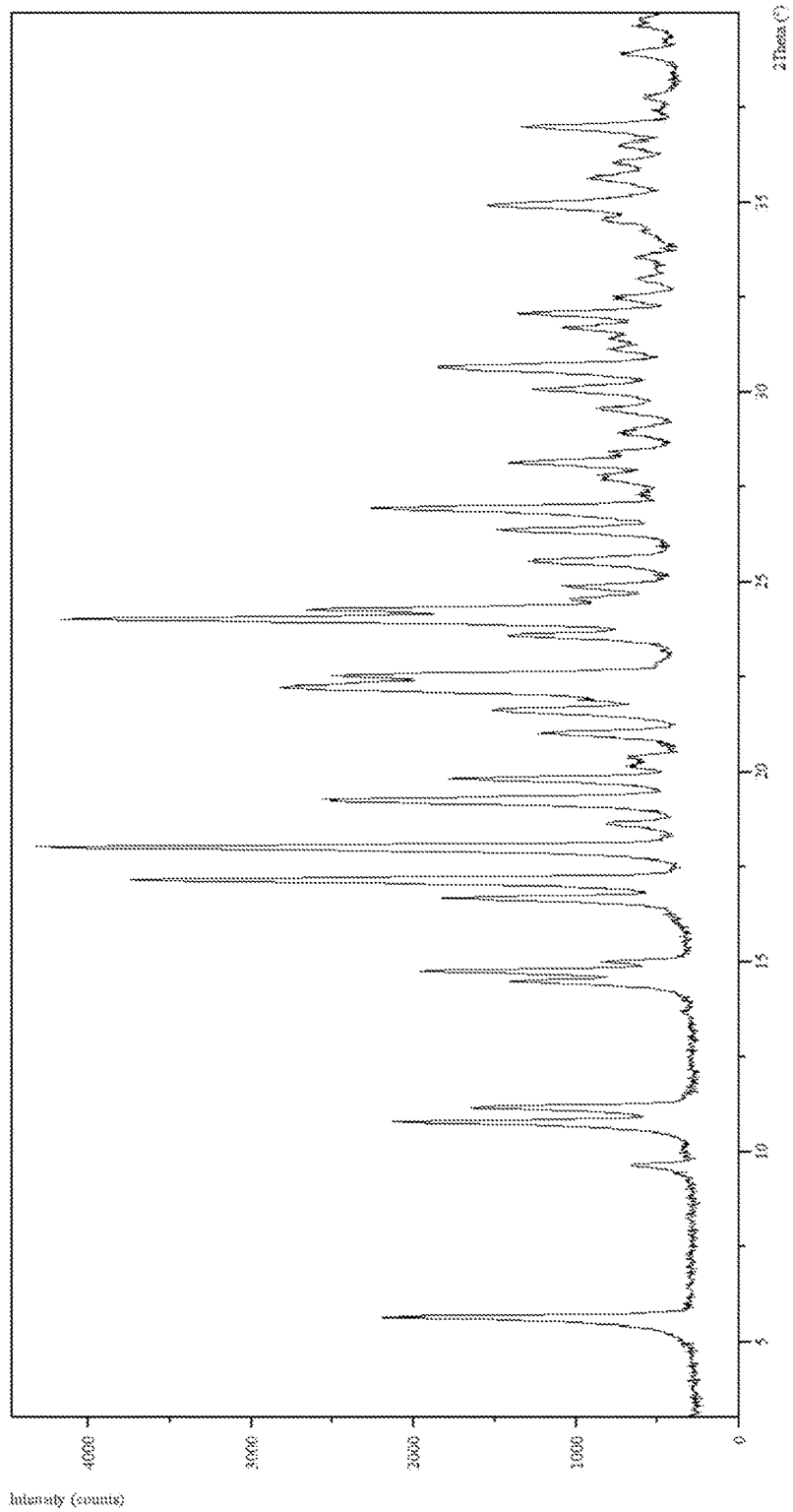
FIG. 26 provides an X-ray powder diffraction (XRPD) pattern of mesylate having crystalline form I(E) of the compound of formula (Ia).

2. Identification of Crystalline Form I(E) of (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Mesylate 1) The XRPD pattern was analyzed and identified by using Empyrean X-ray powder diffraction (XRPD) with Cu-Kα radiation as shown in FIG. 26, having the following characteristic peaks expressed in degrees 2θ at 5.580, 9.59°, 10.73°, 11.13°, 14.43°, 14.71°, 16.62°, 17.10°, 17.96°, 18.590, 19.20°, 19.770, 20.12°, 20.330, 20.95°, 21.560, 22.20°, 22.500, 23.54°, 23.980, 24.24°, 24.510, 24.83°, 25.500, 26.32°, 26.870, 27.70°, 28.100, 28.36°, 28.890, 29.49°, 30.020, 30.58°, 31.220, 31.650, 32.020, 32.430, 32.940, 33.520, 34.500, 34.88°, 35.59°, 36.000, 36.460, 36.920, 37.71° and 38.88°. The error margin in 2θ of the characteristic peaks is ±0.2°.

Figure 27:
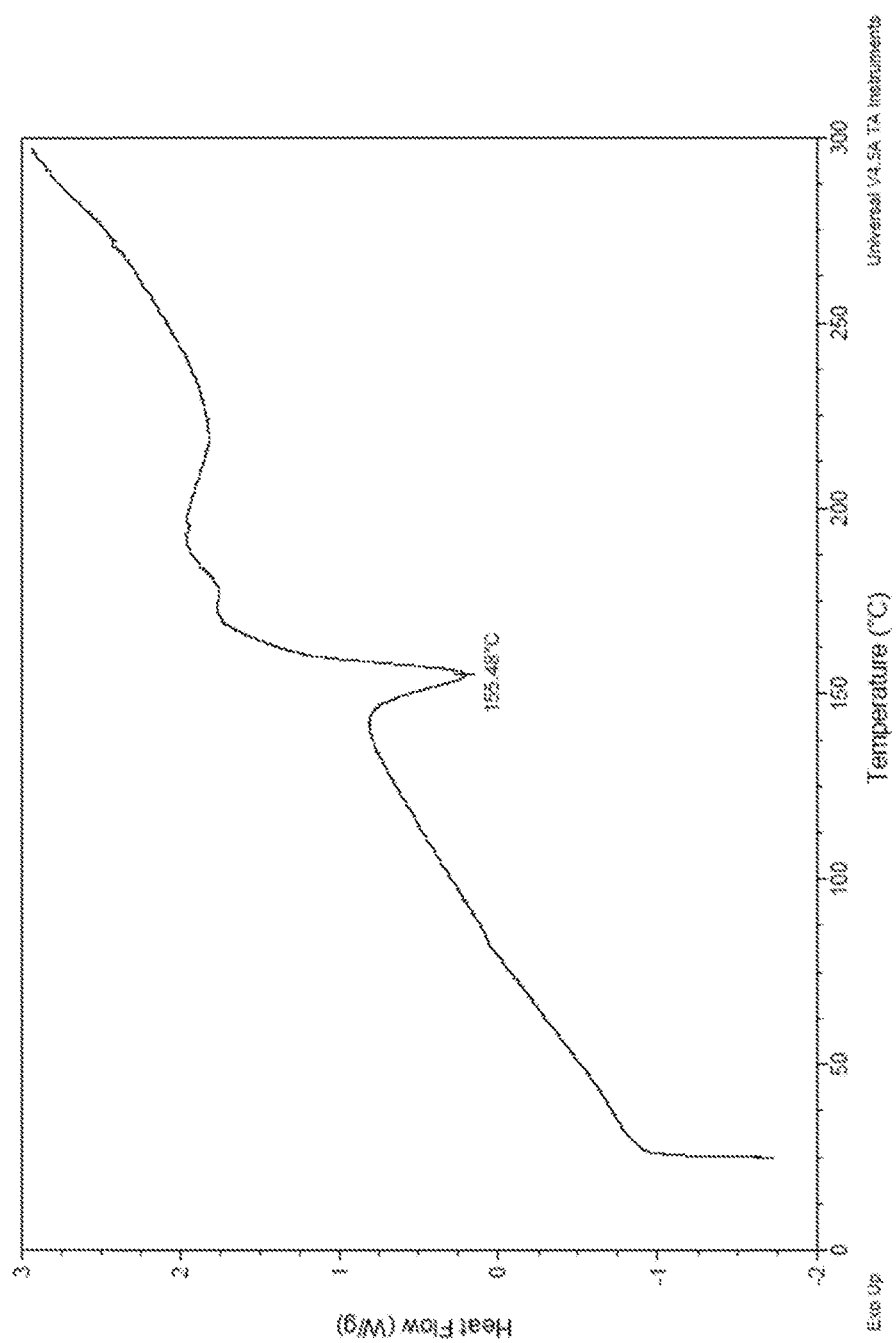
FIG. 27 provides a differential scanning calorimetry (DSC) thermogram of mesylate having crystalline form I(E) of the compound of formula (Ia).

(2) The DSC thermogram was analyzed and identified by using TA Q2000 differential scanning calorimetry (DSC) with a scan rate of 10° C./minute, experimental results are shown in FIG. 27, comprising an endothermic peak at 155.48° C. The error margin of the endothermic peaks is ±3° C.

Example 22: Preparation and Identification of Crystalline Form II of (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Mesylate 1. Preparation of Crystalline Form II of (S)-4-(((R)-6-(2-chloro-4-fluorophenyl)-5-(methoxycarbonyl)-2-(thiazol-22-yl)-1,6-dihydropyrimidin-4-yl)methyl)morpholine-3-carboxylic Acid Mesylate To a dry flask were added sequentially water (4 mL) and mesylate (0.12 g, 1.2 mmol). The mixture was stirred to uniformity at room temperature and warmed to 60° C. To the mixture was added in portions (S)-4-(((R)-6-(2-chloro-4-fluorophenyl)-5-(methoxycarbonyl)-2-(thiazol-2-yl)-3,6-dihydropyrimidin-4-yl)methyl)morpholine-3-carboxylic acid. After the solid was dissolved completely, the mixture was held still for 30 minutes, and then cooled to 25° C. Solid precipitated was remove by filtering, and then the resulting filtrate was allowed to rest for 48 hours to devitrification. The mixture was filtered and the resulting filter cake was washed with water (4 mL), then dried in vacuo at 70° C. for 12 hours to give the compound named (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic acid mesylate having crystalline form II as a yellow solid (0.1 g, productivity: 17%). The compound was characterized by the following spectroscopic data: MS (ESI, pos. ion) m/z: 495.1 [M±H]±; $^1$H NMR (400 MHz, CD$_3$OD) δ 7.97 (d, 1H), 7.82 (d, 1H), 7.47 (dd, 1H), 7.24 (dd, 1H), 7.06 (td, 1H), 6.17 (s, 1H), 4.59 (d, 1H), 4.34 (d, 1H), 4.16-4.08 (m, 2H), 3.96-3.87 (m, 2H), 3.85-3.83 (m, 1H), 3.61 (s, 3H), 3.53-3.48 (m, 1H), 2.90-2.87 (m, 1H), 2.69 (s, 1H).

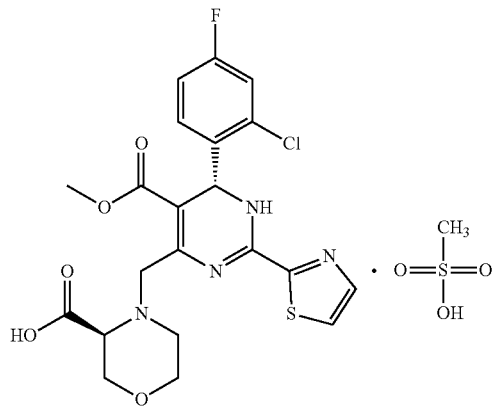

Figure 28:
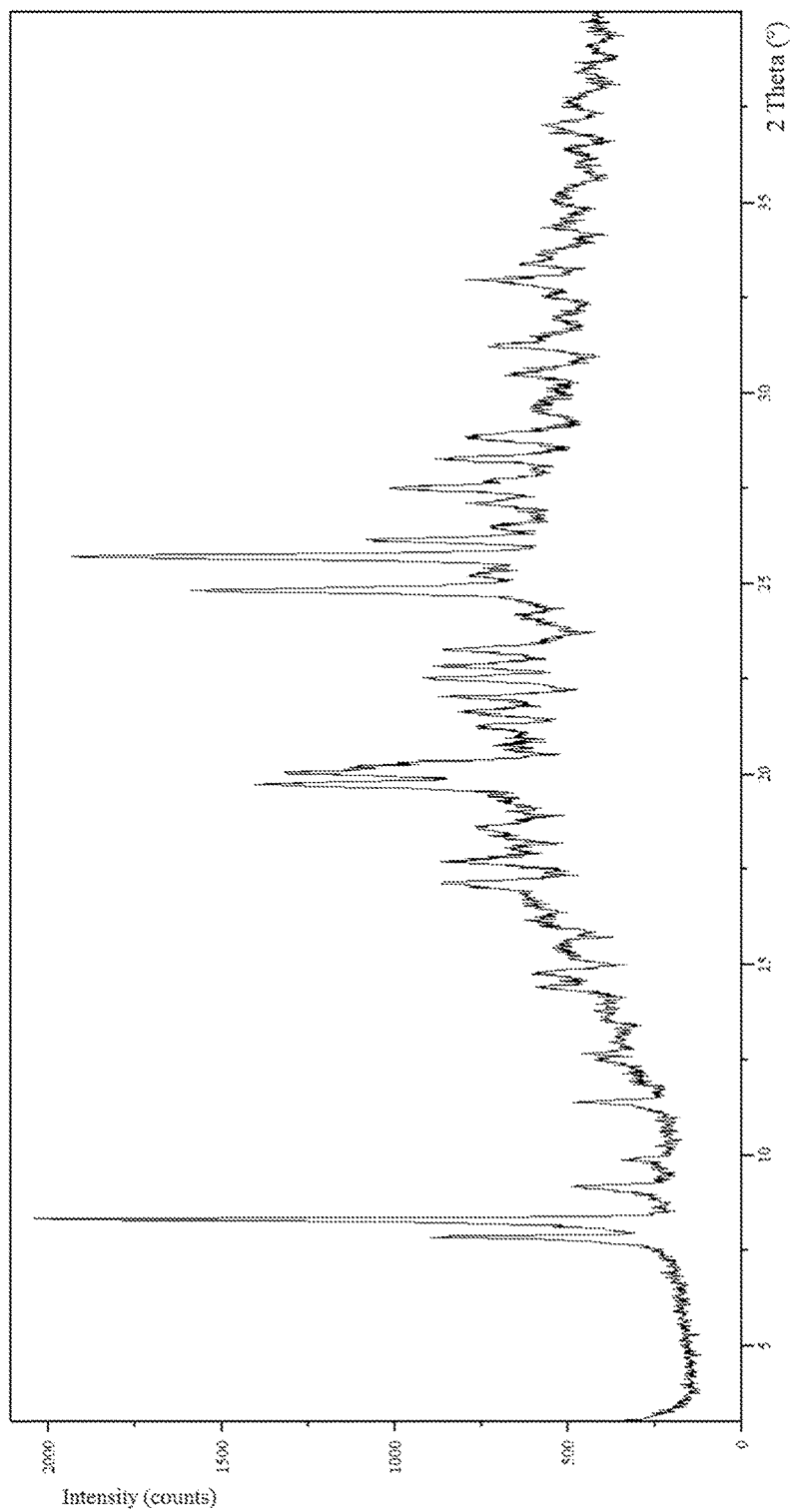
FIG. 28 provides an X-ray powder diffraction (XRPD) pattern of mesylate having crystalline form II of the compound of formula (Ia).

2. Identification of Crystalline Form II of (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic Acid Mesylate (1) The XRPD pattern was analyzed and identified by using Empyrean X-ray powder diffraction (XRPD) with Cu-Kα radiation as shown in FIG. 28, having the following characteristic peaks expressed in degrees 2θ at 7.81°, 8.28°, 9.11°, 9.85°, 11.36°, 12.56°, 14.37°, 14.72°, 15.33°, 16.480, 17.07°, 17.670, 18.51°, 19.700, 20.00°, 20.170, 21.17°, 21.600, 21.97°, 22.470, 22.80°, 23.220, 24.10°, 24.780, 25.66°, 26.100, 26.44°, 27.050, 27.48°, 28.210, 28.79°, 29.600, 30.46°, 31.22°, 32.89°, 33.37°, 33.61°, 34.39°, 35.09°, 36.32°, 36.94°, 37.59° and 38.41°. The error margin in 2θ of the characteristic peaks is ±0.2°.

Figure 29:
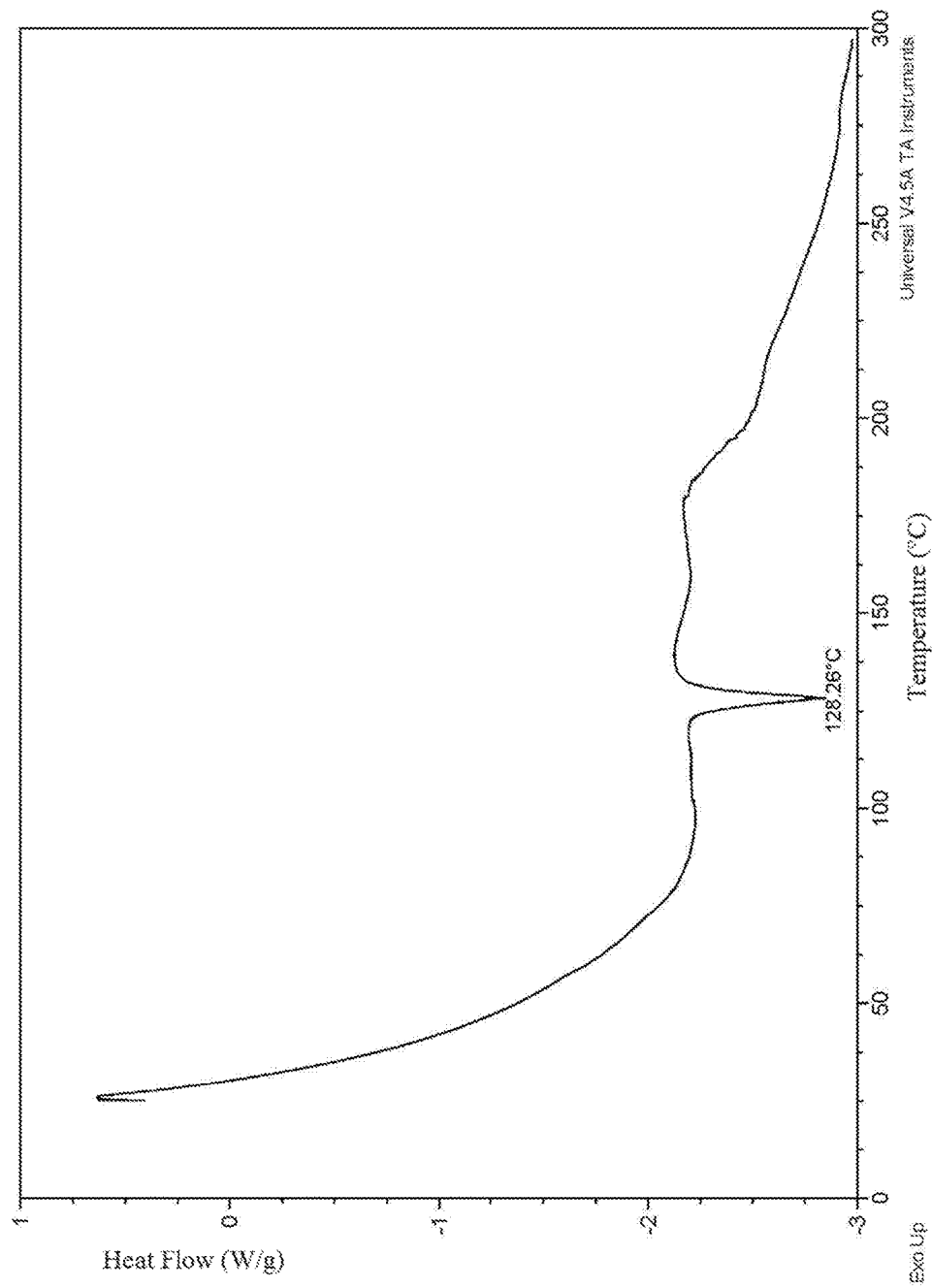
FIG. 29 provides a differential scanning calorimetry (DSC) thermogram of mesylate having crystalline form II of the compound of formula (Ia).

(2) The DSC thermogram was analyzed and identified by using TA Q2000 differential scanning calorimetry (DSC) with a scan rate of 10° C./minute, experimental results are shown in FIG. 29, comprising an endothermic peak at 128.26° C. The error margin of the endothermic peaks is ±3° C.

Example 23: Stability Studies of (S)-4-(((R)-6-(2-chloro-4-fluorophenyl)-5-(methoxycarbonyl)-2-(thiazol-2-yl)-3,6-dihydropyrimidin-4-yl)methyl)morpholine-3-carboxylic Acid, L-tartaric acid Complex of (S)-4-(((R)-6-(2-chloro-4-fluorophenyl)-5-(methoxycarbonyl)-2-(thiazol-2-yl)-3,6-dihydropyrimidin-4-yl)methyl)morpholine-3-carboxylic Acid and its Various Salt Forms Under High Temperature, High Humidity and Illumination Conditions High temperature test: an appropriate amount of sample was put in a weighing bottle in the form of a thin layer of ≤5 mm, under a temperature of 60° C. for 10 days. Appearance, impurity and purity of the samples were tested respectively at the 5th and 10th day. If the sample has changed significantly occurred at 60° C., then the changed sample needs to be retested in the same manner at 40° C. If the sample has no significant change occurred at 60° C., it is not necessary to do the experiment under the condition of 40° C.

High humidity test: an appropriate amount of sample was put in a weighing bottle in the form of a thin layer of ≤5 mm, under a temperature of 25° C. for 10 days. Appearance, impurity and purity were tested respectively at the 5th and 10th day. If the moisture-absorption weight of the sample gains more than 5%, then the sample needs to be retested in the same manner under the conditions of of 25° C. and RH75%±5%. If the moisture-absorption weight of the sample gains less than 5%, and other results meets the requirements, it is not necessary to do the experiment any more. (Note: the weighing bottle should be presaturated for one day by putting it into the humidistat (or a dryer containing a saturated solution of potassium nitrate) before high humidity test, then weighing the sample and weighing bottle together, and record the weight.)

Illumination test: an appropriate amount of sample was put in a weighing bottle in the form of a thin layer of ≤5 mm, under a temperature of 60° C. for 13 days. Appearance, impurity and purity of the samples were tested respectively at the 5th and 13th day.

Experimental results of stability study of the compound of (S)-4-(((R)-6-(2-chloro-4-fluorophenyl)-5-(methoxycarbonyl)-2-(thiazol-2-yl)-3,6-dihydropyrimidin-4-yl)methyl)morpholine-3-carboxylic acid amorphous and the complex of (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic acid and L-tartaric acid and its various salt forms under high temperature, high humidity and illumination conditions are shown in Table 4.

TABLE 4

Experimental results of stability study

| Subject sample | Condition Project | 0 days | High temperature 5 days | High temperature 10 days | High humidity 5 days | High humidity 10 days | Illumination 5 days | Illumination 13 days |
|---|---|---|---|---|---|---|---|---|
| The amorphous compound (I) prepared by Example 1 | Appearance | a yellow foamy solid | a yellow foamy solid | a yellow foamy solid | a yellow foamy solid | a yellow foamy solid | a yellow foamy solid | a yellow foamy solid |
| | Total impurity (%) | 2.46 | 3.01 | 4.35 | 2.49 | 2.58 | 6.28 | 9.44 |
| | Purity (%) | 97.54 | 96.99 | 95.65 | 97.51 | 97.42 | 93.72 | 90.56 |
| Complex having crystalline form I(A) of L-tartaric acid and the compound of (Ia) | Appearance | yellow crystalline solid | yellow crystalline solid | yellow crystalline solid | yellow crystalline solid | yellow crystalline solid | yellow crystalline solid | yellow crystalline solid |
| | Total impurity (%) | 0.15 | 0.17 | 0.16 | 0.16 | 0.18 | 0.14 | 0.16 |
| | Purity (%) | 99.85 | 99.83 | 99.84 | 99.84 | 99.82 | 99.86 | 99.84 |
| Compound hydrobromide having crystalline form I(C) | Appearance | yellow solid | yellow solid | yellow solid | yellow solid | yellow solid | yellow solid | yellow solid |
| | Total impurity (%) | 0.30 | 0.31 | 0.37 | 0.32 | 0.36 | 2.37 | 3.94 |
| | Purity (%) | 99.70 | 99.69 | 99.63 | 99.68 | 99.64 | 97.63 | 96.06 |
| Compound hydrochloride having crystalline form II | Appearance | yellow solid | yellow solid | yellow solid | yellow solid | yellow solid | yellow solid | yellow solid |
| | Total impurity (%) | 0.37 | 0.37 | 0.57 | 0.35 | 0.41 | 2.41 | 2.53 |
| | Purity (%) | 99.63 | 99.63 | 99.43 | 99.65 | 99.59 | 97.59 | 97.47 |

As seen in the data analysis of Table 4

(a) The complex having crystalline form I(A) of (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic acid and L-tartaric acid, hydrobromide having crystalline form I(C) and hydrochloride having crystalline form II have a better preparation purity than amorphous (S)-4-(((R)-6-(2-chloro-4-fluorophenyl)-5-(methoxycarbonyl)-2-(thiazol-2-yl)-3,6-dihydropyrimidin-4-yl)methyl)morpholine-3-carboxylic acid, wherein the preparation purity of crystalline form I(A) of L-tartaric acid complex is 99.85%, and the oxide impurities is less than 0.2%.

(b) The complex having crystalline form I(A) of (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic acid and L-tartaric acid, hydrobromide having crystalline form I(C) and hydrochloride having crystalline form II have a better stability than amorphous (S)-4-(((R)-6-(2-chloro-4-fluorophenyl)-5-(methoxycarbonyl)-2-(thiazol-2-yl)-3,6-dihydropyrimidin-4-yl)methyl)morpholine-3-carboxylic acid under high temperature, high humidity and illumination condition. Wherein L-tartaric acid complex having crystalline form I(A) has a best stability, the appearance and the purity was basically unchanged under high temperature, high humidity and illumination condition.

Example 24: Test Compounds' PK Assay in Beagle

1. Experimental Method

The test compounds were administered intragastrically at dosage of 10 mg/kg or 5 mg/kg, or administered at dosage of 1 mg/kg, 2 mg/kg or 10 mg/kg by tail-intravenous injection to beagle.

Blood samples of orbital vein were taken at 0.083, 0.25, 0.5, 1, 2, 4, 6, 8 and 24 hours after the administration, and collected in anticoagulation tube with EDTA-K2. The test compounds were extracted from plasma samples by liquid-liquid extraction. Then quantitative analysis was performed on a triple-quadrupole tandem mass spectrometer using multiple reaction monitoring (MRM). Pharmacokinetic parameters were calculated using WinNonlin 6.1 software with non compartment model method.

Example 25: The Experimental Study of Hygroscopicity

A dry glass weighing bottle with a plug was placed in a suitable thermostatic drier at 25° C.±1° C. (ammonium chloride and saturated solution of ammonium sulfate were placed on the bottom) on the day before the experiment, and weighed precisely. The propriate amount of the sample was plated into the weighing bottle, wherein the thickness of the sample typically is about 1 mm, and weighed precisely (m2). The weighing bottle was open and placed with the plug in the above constant temperature and humidity condition for 24 hours. The capped weighing bottle was weighed precisely (m3), and the weight gain percentage was calculated (%).

Test method: according to the Ph. Eur. <5.11>; Ch. P. 2010; II appendix XIX J;

Weighting percentage of moisture absorption (%)= $(m3-m2)/(m2-m1) \times 100\%$

Hygroscopicity characteristics: weighting percentage of moisture absorption

Judgement of Hygroscopicity Result:

(1) Air slaking: absorbing enough water to form liquid
(2) Of quite hygroscopicity: not less than 15%

(3) Of hygroscopicity: less than 15% but not less 2%

(4) Of slight hygroscopicity: less than 2% but not less than 0.2%

(5) Of no or little hygroscopicity: less than 0.2%.

Experimental results of hygroscopicity study of the compound of (S)-4-(((R)-6-(2-chloro-4-fluorophenyl)-5-(methoxycarbonyl)-2-(thiazol-2-yl)-3,6-dihydropyrimidin-4-yl)methyl)morpholine-3-carboxylic acid amorphous and the complex of (S)-4-(((R)-6-(2-chloro-4-fluorophenyl)-5-(methoxycarbonyl)-2-(thiazol-2-yl)-1,6-dihydropyrimidin-4-yl)methyl)morpholine-3-carboxylic acid and L-tartaric acid and its various salt forms under high temperature, high humidity and illumination conditions are shown in Table 5.

TABLE 5

Results of hygroscopicity study of crystalline form I(A) of compound (I) and the complex of compound (Ia) and L-tartaric acid

| Subject sample | Weight of weighing bottle (mg) | Weight of weighing bottle and sample (mg) | Weight of weighing bottle and sample moisture absorption (mg) | Weighting percentage of moisture absorption (%) |
|---|---|---|---|---|
| Compound (I) prepared by Example 1 | 2943.638 | 3044.370 | 3045.822 | 1.441% |
| Crystalline form I(A) of the complex of compound (Ia) and L-tartaric acid | 31328.320 | 32347.410 | 32347.710 | 0.029% |

As seen in the data analysis of Table 5, the weighting percentage of moisture absorption of crystalline form I(A) of the complex of compound (Ia) and L-tartaric acid is 0.029%, of no or little hygroscopicity, and the weighting percentage of moisture absorption of compound (I) is 1.441%. The hygroscopicity of crystalline form I(A) of the complex of compound (Ia) and L-tartaric acid is much smaller than that of amorphous compound (I) prepared by Example 1.

Although the present invention has been described in detail by general description, description of the embodiments and assays, it will be obvious to one skilled in the art that certain changes and modifications may be made without departing from the invention, and therefore, all such changes and modifications are within the scope of the claims.

What is claimed is:

1. A complex formed from L-tartaric acid and a compound of formula (I) or (Ia):

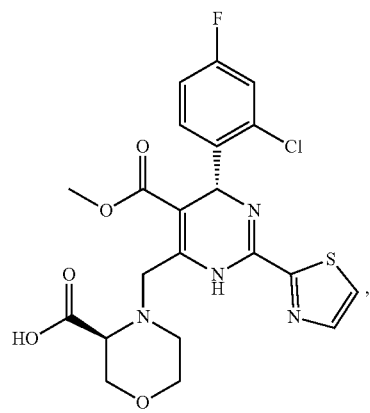

(I)

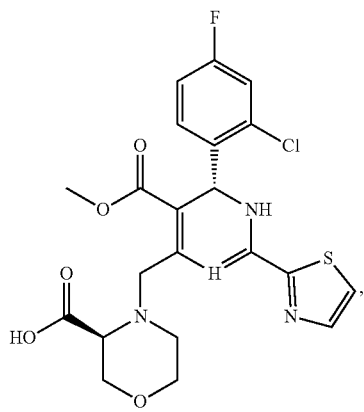

(Ia)

wherein the complex is L-tartaric acid complex having crystalline form I(A), a mole ratio of the compound of formula (I) or (Ia) to L-tartarate is 1:1 in the crystalline form I(A) of L-tartaric acid complex, and wherein the crystalline form I(A) exhibits the following characteristic X-ray powder diffraction peaks expressed in degrees 2θ at 17.82±0.2°, 19.51±0.2°, 21.61±0.2°, 22.56±0.2°, 23.36±0.2°, 23.54±0.2°, 23.79±0.2° and 31.07±0.2°.

2. The complex of claim 1, wherein the complex is L-tartaric acid complex having crystalline form I(A), and wherein the crystalline form I(A) exhibits the following characteristic X-ray powder diffraction peaks expressed in degrees 2θ at 9.29±0.2°, 17.82±0.2°, 19.51±0.2°, 20.80±0.2°, 21.61±0.2°, 22.56±0.2°, 23.36±0.2°, 23.54±0.2°, 23.79±0.2° and 31.07±0.2°.

3. The complex of claim 1, wherein the complex is L-tartaric acid complex having crystalline form I(A), and wherein the crystalline form I(A) exhibits the following characteristic X-ray powder diffraction peaks expressed in degrees 2θ at 7.300°±0.2°, 7.31°±0.2°, 7.61°±0.2°, 9.29°±0.2°, 11.60°±0.2°, 14.69°±0.2°, 15.33°±0.2°, 17.22°±0.2°, 17.82°±0.2°, 18.08°±0.2°, 18.42°±0.2°, 19.51°±0.2°, 20.51°±0.2°, 20.80°±0.2°, 21.61°±0.2°, 22.56°±0.2°, 23.05°±0.2°, 23.36°±0.2°, 23.54°±0.2°, 23.79°±0.2°, 24.39°±0.2°, 24.810°±0.2°, 25.78°±0.2°, 26.07°±0.2°, 27.34°±0.2°, 28.25°±0.2°, 28.87°±0.2°, 29.72°±0.2°, 30.22°±0.2°, 31.07°±0.2°, 31.55°±0.2°, 32.25°±0.2°, 32.85°±0.2°, 33.24°±0.2°, 34.24°±0.2°, 35.03°±0.2°, 35.22°±0.2°, 36.03°±0.2°, 36.88°±0.2°, 37.33°±0.2°, 37.86°±0.2° and 38.36°±0.2°.

4. The complex of claim 1, wherein the complex is L-tartaric acid complex having crystalline form I(A), and wherein the crystalline form I(A) has a differential scanning calorimetry thermogram comprising an endothermic peak at 186.94° C.±3° C. or 193.78° C.±3° C.; and/or a Raman spectrogram comprising the following absorption peaks at 51, 71, 115, 144, 158, 180, 196, 234, 303, 427, 688, 746, 767, 818, 837, 905, 1001, 1062, 1075, 1128, 1137, 1165, 1179, 1193, 1230, 1269, 1289, 1324, 1337, 1346, 1357, 1401, 1438, 1453, 1477, 1517, 1541, 1607 and 1679 cm$^{-1}$, and the error margin of the absorption peaks is ±2 cm$^{-1}$.

5. The complex of claim 1, wherein the complex is L-tartaric acid complex having crystalline form I(A), and wherein the crystalline form I(A) has at least one of following features:
   (1) an X-ray powder diffraction (XRPD) pattern substantially the same as shown in FIG. 1; or
   (2) a differential scanning calorimetry thermogram substantially the same as shown in FIG. 2 or FIG. 3; or
   (3) a Raman spectrogram substantially the same as shown in FIG. 4.

6. A salt of a compound of formula (I) or (Ia):

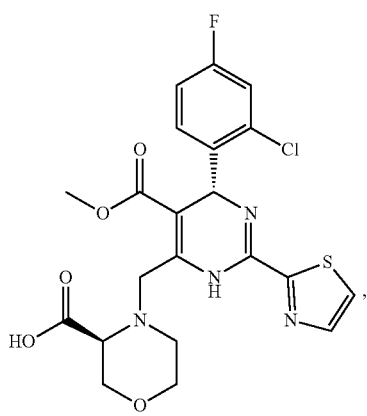

(I)

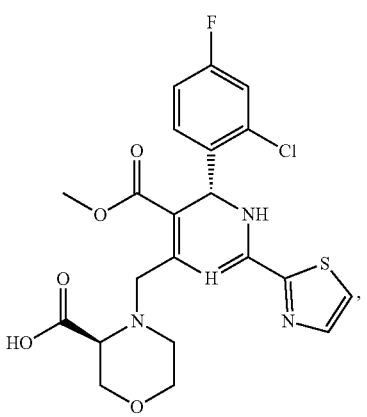

(Ia)

wherein the salt is hydrobromide having crystalline form I(C) having an X-ray powder diffraction (XRPD) pattern substantially the same as shown in FIG. 8; and/or a differential scanning calorimetry thermogram substantially the same as shown in FIG. 9; or
wherein the salt is mesylate having crystalline form II having an X-ray powder diffraction (XRPD) pattern substantially the same as shown in FIG. 28; and/or a differential scanning calorimetry thermogram substantially the same as shown in FIG. 29; or wherein the salt is amorphous hydrochloride having an X-ray powder diffraction (XRPD) pattern substantially the same as shown in FIG. 10; or wherein the salt is amorphous benzene sulfonate having an X-ray powder diffraction (XRPD) pattern substantially the same as shown in FIG. 11; or wherein the salt is amorphous tosilate having an X-ray powder diffraction (XRPD) pattern substantially the same as shown in FIG. 12; or wherein the salt is amorphous oxalate having an X-ray powder diffraction (XRPD) pattern substantially the same as shown in FIG. 13; or wherein the salt is amorphous citrate having an X-ray powder diffraction (XRPD) pattern substantially the same as shown in FIG. 14; or wherein the salt is amorphous maleate having an X-ray powder diffraction (XRPD) pattern substantially the same as shown in FIG. 15; or wherein the salt is amorphous hydrobromide having an X-ray powder diffraction (XRPD) pattern substantially the same as shown in FIG. 16; or wherein the salt is amorphous sulfate having an X-ray powder diffraction (XRPD) pattern substantially the same as shown in FIG. 17; or wherein the salt is amorphous nitrate having an X-ray powder diffraction (XRPD) pattern substantially the same as shown in FIG. 18; or wherein the salt is amorphous L-tartarate having an X-ray powder diffraction (XRPD) pattern substantially the same as shown in FIG. 19; or wherein the salt is amorphous salicylate having an X-ray powder diffraction (XRPD) pattern substantially the same as shown in FIG. 20; or wherein the salt is an amorphous sodium salt having an X-ray powder diffraction (XRPD) pattern substantially the same as shown in FIG. 23; or wherein the salt is an amorphous calcium salt having an X-ray powder diffraction (XRPD) pattern substantially the same as shown in FIG. 24; or wherein the salt is an amorphous L-lysine salt having an X-ray powder diffraction (XRPD) pattern substantially the same as shown in FIG. 25.

7. A salt of a compound of formula (I) or (Ia):

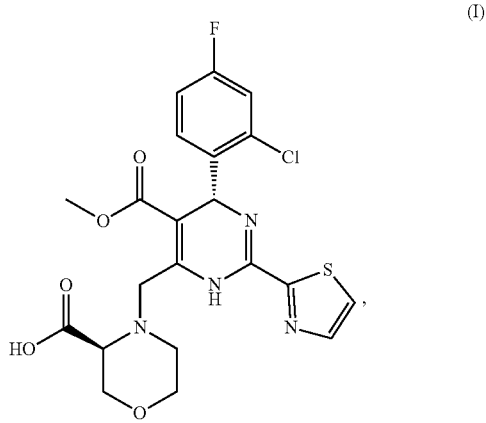

(I)

(Ia)

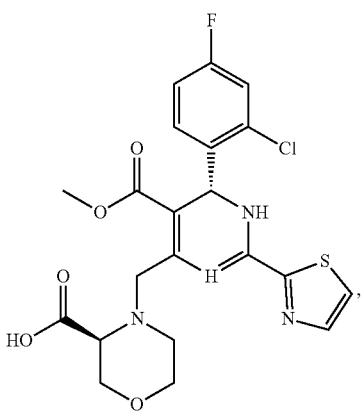

wherein the salt is hydrobromide having crystalline form I(C), and wherein the crystalline form I(C) exhibits the following characteristic X-ray powder diffraction peaks expressed in degrees 2θ at 20.69±0.2°, 21.61±0.2°, 23.18±0.2°, 24.20±0.2°, 27.09±0.2°, 28.05±0.2°, 28.59±0.2° and 33.13±0.2°; or wherein the salt is mesylate having crystalline form II, wherein a mole ratio of the compound of formula (I) or (Ia) to mesylate is 3:1 in the crystalline form II, and wherein the crystalline form II exhibits the following characteristic X-ray powder diffraction peaks expressed in degrees 2θ at 8.28°±0.2°, 19.70°±0.2°, 20.00°±0.2°, 24.78°±0.2° and 25.66°±0.2°.

8. The salt of claim 7, wherein the salt is hydrobromide having crystalline form I(C), and wherein the crystalline form I(C) exhibits the following characteristic X-ray powder diffraction peaks expressed in degrees 2θ at 14.87±0.2°, 20.69±0.2°, 21.61±0.2°, 23.18±0.2°, 24.20±0.2°, 25.38±0.2°, 27.09±0.2°, 28.05±0.2°, 28.59±0.2° and 33.13±0.2°.

9. The salt of claim 7, wherein the salt is hydrobromide having crystalline form I(C), and wherein the crystalline form I(C) exhibits the following characteristic X-ray powder diffraction peaks expressed in degrees 2θ at 6.29±0.2°, 10.04±0.2°, 10.99±0.2°, 11.83±0.2°, 14.87±0.2°, 15.44±0.2°, 16.05±0.2°, 18.41±0.2°, 18.79±0.2°, 19.12±0.2°, 20.06±0.2°, 20.69±0.2°, 21.30±0.2°, 21.61±0.2°, 22.02±0.2°, 22.93±0.2°, 23.18±0.2°, 23.67±0.2°, 24.20±0.2°, 25.38±0.2°, 26.14±0.2°, 26.73±0.2°, 27.09±0.2°, 27.83±0.2°, 28.05±0.2°, 28.59±0.2°, 29.06±0.2°, 29.92±0.2°, 31.05±0.2°, 31.63±0.2°, 32.29±0.2°, 32.76±0.2°, 33.13±0.2°, 33.63±0.2°, 34.10±0.2°, 34.55±0.2°, 35.42±0.2°, 35.99±0.2°, 36.36±0.2°, 37.02±0.2°, 37.93±0.2°, 38.49±0.2°, 38.72±0.2° and 39.10±0.2°, and/or has a differential scanning calorimetry thermogram comprising an endothermic peak at 158.95° C.±3° C.

10. The salt of claim 7, wherein the salt is mesylate having crystalline form II, and wherein the crystalline form II exhibits the following characteristic X-ray powder diffraction peaks expressed in degrees 2θ at 8.28° 0.2°, 9.11°±0.2°, 11.36°±0.2°, 17.07°±0.2°, 17.67°±0.2°, 19.70°±0.2°, 20.00°±0.2°, 24.78°±0.2°, 25.66°±0.2° and 26.10°±0.2°.

11. The salt of claim 7, wherein the salt is mesylate having crystalline form II, and wherein the crystalline form II exhibits the following characteristic X-ray powder diffraction peaks expressed in degrees 2θ at 7.81°±0.2°, 8.28°±0.2°, 9.11°±0.2°, 9.85°±0.2°, 11.36°±0.2°, 12.56°±0.2°, 14.37°±0.2°, 14.72°±0.2°, 15.33°±0.2°, 16.48°±0.2°, 17.07°±0.2°, 17.67°±0.2°, 18.51°±0.2°, 19.70°±0.2°, 20.00°±0.2°, 20.17°±0.2°, 21.17°±0.2°, 21.60°±0.2°, 21.97°±0.2°, 22.47°±0.2°, 22.80°±0.2°, 23.22°±0.2°, 24.10°±0.2°, 24.78°±0.2°, 25.66°±0.2°, 26.10°±0.2°, 26.44°±0.2°, 27.05°±0.2°, 27.48°±0.2°, 28.21°±0.2°, 28.79°±0.2°, 29.60°±0.2°, 30.46°±0.2°, 31.22°±0.2°, 32.89°±0.2°, 33.37°±0.2°, 33.61°±0.2°, 34.39°±0.2°, 35.09°±0.2°, 36.32°±0.2°, 36.94°±0.2°, 37.59°±0.2° and 38.41°±0.2°, and/or has a differential scanning calorimetry thermogram comprising an endothermic peak at 128.26° C.±3° C.

12. A pharmaceutical composition comprising the complex of claim 1, and a pharmaceutically acceptable carrier, excipient, diluent, adjuvant, vehicle or a combination thereof.

13. A method for, managing, treating or lessening an HBV disease in a patient, comprising administering to the patient with a therapeutically effective amount of the complex of claim 1.

14. The method of claim 13, wherein the HBV disease is hepatitis B infection or a disease caused by hepatitis B infection; and wherein the disease caused by hepatitis B infection is cirrhosis or hepatocellular carcinoma.

15. A pharmaceutical composition comprising the salt of claim 6, and a pharmaceutically acceptable carrier, excipient, diluent, adjuvant, vehicle or a combination thereof.

16. A method for, managing, treating or lessening an HBV disease in a patient, comprising administering to the patient with a therapeutically effective amount of the salt of claim 6.

17. The method of claim 16, wherein the HBV disease is hepatitis B infection or a disease caused by hepatitis B infection; and wherein the disease caused by hepatitis B infection is cirrhosis or hepatocellular carcinoma.

18. A method for, managing, treating or lessening an HBV disease in a patient, comprising administering to the patient with a therapeutically effective amount of the pharmaceutical composition of claim 12.

19. The method of claim 18, wherein the HBV disease is hepatitis B infection or a disease caused by hepatitis B infection; and wherein the disease caused by hepatitis B infection is cirrhosis or hepatocellular carcinoma.

20. A method for, managing, treating or lessening an HBV disease in a patient, comprising administering to the patient with a therapeutically effective amount of the pharmaceutical composition of claim 15.

21. The method of claim 20, wherein the HBV disease is hepatitis B infection or a disease caused by hepatitis B infection; and wherein the disease caused by hepatitis B infection is cirrhosis or hepatocellular carcinoma.

22. A method for managing, treating or lessening an HBV disease in a patient, comprising administering to the patient with a therapeutically effective amount of the salt of claim 7.

23. The method of claim 22, wherein the HBV disease is hepatitis B infection or a disease caused by hepatitis B infection; and wherein the disease caused by hepatitis B infection is cirrhosis or hepatocellular carcinoma.

* * * * *